(12) United States Patent
Silverman et al.

(10) Patent No.: US 11,207,283 B2
(45) Date of Patent: Dec. 28, 2021

(54) INACTIVATORS OF TOXOPLASMA GONDII ORNITHINE AMINOTRANSFERASE FOR TREATING TOXOPLASMOSIS AND MALARIA

(71) Applicant: Northwestern University, Evanston, IL (US)

(72) Inventors: Richard B. Silverman, Winnetka, IL (US); Hoang V. Le, Oxford, MS (US); Rima L. McLeod, Chicago, IL (US); Dustin D. Hawker, Evanston, IL (US)

(73) Assignees: Northwestern University, Evanston, IL (US); The University of Chicago, Chicago, IL (US)

( * ) Notice: Subject to any disclaimer, the term of this patent is extended or adjusted under 35 U.S.C. 154(b) by 0 days.

(21) Appl. No.: 16/836,870

(22) Filed: Mar. 31, 2020

(65) Prior Publication Data
US 2020/0281880 A1 Sep. 10, 2020

Related U.S. Application Data

(62) Division of application No. 15/728,714, filed on Oct. 10, 2017, now Pat. No. 10,632,088.

(60) Provisional application No. 62/406,104, filed on Oct. 10, 2016.

(51) Int. Cl.
| | | |
|---|---|---|
| *A61K 31/196* | (2006.01) | |
| *A61K 31/13* | (2006.01) | |
| *A61K 31/035* | (2006.01) | |
| *C12N 9/10* | (2006.01) | |
| *A61K 31/40* | (2006.01) | |
| *A61K 31/341* | (2006.01) | |
| *A61K 31/381* | (2006.01) | |
| *A61K 31/03* | (2006.01) | |
| *C07C 229/38* | (2006.01) | |
| *C07C 229/34* | (2006.01) | |

(52) U.S. Cl.
CPC ............ *A61K 31/196* (2013.01); *A61K 31/03* (2013.01); *A61K 31/035* (2013.01); *A61K 31/13* (2013.01); *A61K 31/341* (2013.01); *A61K 31/381* (2013.01); *A61K 31/40* (2013.01); *C07C 229/34* (2013.01); *C07C 229/38* (2013.01); *C12N 9/1096* (2013.01); *C12Y 206/01013* (2013.01); *Y02A 50/30* (2018.01)

(58) Field of Classification Search
CPC .................................................. A61K 31/196
See application file for complete search history.

(56) References Cited

U.S. PATENT DOCUMENTS

| | | | | |
|---|---|---|---|---|
| 8,252,831 B2 * | 8/2012 | Kuklish | ............... | C07D 233/88 |
| | | | | 514/398 |
| 2010/0197924 A1 * | 8/2010 | Gould | .................. | C07D 213/75 |
| | | | | 546/123 |

OTHER PUBLICATIONS

Schiffler et al., Journal of Medicinal Chemistry (2016), 59(1), 194-205.*
Huang et al., Bioorganic & Medicinal Chemistry Letters (2016), 26(4), 1156-1160.*
Newman, J.; Seabrook, S.; Surjadi, R.; Williams, C. C.; Lucent, D.; Wilding, M.; Scott, C.; Peat, T. S. PLoS One 2013, 8 (3), e58298.
Painter, J.; Merritt, E. A. Acta Crystallogr. Sect. D Biol. Crystallogr. 2006, 62 (4), 439-450.
Painter, J.; Merritt, E. A. J. Appl. Crystallogr. 2006, 39 (1), 109-111.
Pan, Y.; Qiu, J.; Silverman, R. B. J. Med. Chem. 2003, 46 (25), 5292-5293.
Petersen, E.; Liesenfeld, O. In Toxoplasma Gondii; Weiss, L. M., Kim, K., Eds.; Academic Press: London, 2007; pp. 81-100.
Plouffe, D.; Brinker, A.; McNamara, C.; Henson, K.; Kato, N.; Kuhen, K.; Nagle, A.; Adrián, F.; Matzen, J. T.; Anderson, P.; Nam, T.; Gray, N. S.; Chatterjee, A.; Janes, J.; Yan, S. F.; Trager, R.; Caldwell, J. S.; Schultz, P. G.; Zhou, Y.; Winzeler, E. A. Proc. Natl. Acad. Sci. 2008, 105 (26), 9059-9064.
Rando, R. R.; Bangerter, F. W. J. Am. Chem. Soc. 1976, 98 (21), 6762-6764.
Rosenthal, P. J. Mol. Microbiol. 2013, 89 (6), 1025-1038.
Rover Júnior, L.; Fernandes, J. C.; de Oliveira Neto, G.; Kubota, L. T.; Katekawa, E.; Serrano, S. H. Anal. Biochem. 1998, 260 (1), 50-55.
Salminen, K. A.; Leppänen, J.; Venäläinen, J. I.; Pasanen, M.; Auriola, S.; Juvonen, R. O.; Raunio, H. Drug Metab. Dispos. 2011, 39 (3), 412-418.
Seiler, N. Curr. Drug Targets 2000, 1 (2), 119-153.
Shah, S. A.; Shen, B. W.; Brünger, A. T. Structure 1997, 5 (8), 1067-1075.
Shen, B. W.; Hennig, M.; Hohenester, E.; Jansonius, J. N.; Schirmer, T. J. Mol. Biol. 1998, 277 (1), 81-102.
Silverman, R. B.; Invergo, B. J. Biochemistry 1986, 25 (22), 6817-6820.
Silverman, R. B. J. Med. Chem. 2012, 55 (2), 567-575.

(Continued)

*Primary Examiner* — Paul V Ward
(74) *Attorney, Agent, or Firm* — Quarles & Brady LLP

(57) ABSTRACT

Disclosed are methods, compounds, and compositions for treating infection by an Apicomplexan parasite that include administering a compound that selectively inactivates ornithine aminotransferase of the Apicomplexan parasite. Specifically, the methods, compounds, compounds may be utilized for treating infection by *Toxoplasma gondii* and toxoplasmosis and for treating infection by *Plasmodium falciparum* and malaria. The compounds disclosed herein are observed to selectively inactivate *Toxoplasma gondii* ornithine aminotransferase (TgOAT) relative to human OAT and relative to human γ-aminobutyric aminotransferase (GABA-AT).

11 Claims, 11 Drawing Sheets

Specification includes a Sequence Listing.

(56) References Cited

OTHER PUBLICATIONS

Sievers, F.; Wilm, A.; Dineen, D.; Gibson, T. J.; Karplus, K.; Li, W.; Lopez, R.; McWilliam, H.; Remmert, M.; Söding, J.; Thompson, J. D.; Higgins, D. G. Mol. Syst. Biol. 2011, 7 (1), 539.
Singh, J.; Petter, R. C.; Baillie, T. A.; Whitty, A. Nat. Rev. Drug Discov. 2011, 10 (4), 307-317.
Sj, Arnold; Mc, K.; Ms, M.; S, D.; Ma, S. Arch. Pathol. Lab. Med. 1997, 121 (8), 869-873.
Storici, P.; Capitani, G.; Müller, R.; Schirmer, T.; Jansonius, J. N. J. Mol. Biol. 1999, 285 (1), 297-309.
Su, C.; Khan, A.; Zhou, P.; Majumdar, D.; Ajzenberg, D.; Dardé, M.-L.; Zhu, X.-Q.; Ajioka, J. W.; Rosenthal, B. M.; Dubey, J. P.; Sibley, L. D. Proc. Natl. Acad. Sci. 2012, 109 (15), 5844-5849.
Vedadi, M.; Lew, J.; Artz, J.; Amani, M.; Zhao, Y.; Dong, A.; Wasney, G. A.; Gao, M.; Hills, T.; Brokx, S.; Qiu, W.; Sharma, S.; Diassiti, A.; Alam, Z.; Melone, M.; Mulichak, A.; Wernimont, A.; Bray, J.; Loppnau, P.; Plotnikova, O.; Newberry, K.; Sundararajan, E.; Houston, S.; Walker, J.; Tempel, W.; Bochkarev, A.; Kozieradzki, I.; Edwards, A.; Arrowsmith, C.; Roos, D.; Kain, K.; Hui, R. Mol. Biochem. Parasitol. 2007, 151 (1), 100-110.
Wang, Z.; Yuan, H.; Nikolic, D.; Van Breemen, R. B.; Silverman, R. B. Biochemistry 2006, 45 (48), 14513-14522.
Waxman, S.; Herbert, V. N. Engl. J. Med. 1969, 280 (24), 1316-1319.
Winn, M. D.; Ballard, C. C.; Cowtan, K. D.; Dodson, E. J.; Emsley, P.; Evans, P. R.; Keegan, R. M.; Krissinel, E. B.; Leslie, A. G. W.; McCoy, A.; McNicholas, S. J.; Murshudov, G. N.; Pannu, N. S.; Potterton, E. A.; Powell, H. R.; Read, R. J.; Vagin, A.; Wilson, K. S. Acta Crystallogr. D. Biol. Crystallogr. 2011, 67 (Pt 4), 235-242.
World Malaria Report, 2014; World Health Organization: Geneva, Switzerland, 2014.
Yilmaz, S. M.; Hopkins, S. H. J. Parasitol. 1972, 58 (5), 938-939.
Yuan, H.; Silverman, R. B. Bioorganic Med. Chem. 2006, 14 (5), 1331-1338.
Yuan, H.; Silverman, R. B. Bioorganic Med. Chem. Lett. 2007, 17 (6), 1651-1654.
Zigmond, E.; Ya'acov, A. Ben; Lee, H.; Lichtenstein, Y.; Shalev, Z.; Smith, Y.; Zolotarov, L.; Ziv, E.; Kalman, R.; Le, H. V.; Lu, H.; Silverman, R. B.; Ilan, Y. ACS Med. Chem. Lett. 2015, 150708125556004.
Agüero, F.; Al-Lazikani, B.; Aslett, M.; Berriman, M.; Buckner, F. S.; Campbell, R. K.; Carmona, S.; Carruthers, I. M.; Chan, A. W. E.; Chen, F.; Crowther, G. J.; Doyle, M. A.; Hertz-Fowler, C.; Hopkins, A. L.; McAllister, G.; Nwaka, S.; Overington, J. P.; Pain, A.; Paolini, G. V.; Pieper, U.; Ralph, S. A.; Riechers, A.; Roos, D. S.; Sali, A.; Shanmugam, D.; Suzuki, T.; Van Voorhis, W. C.; Verlinde, C. L. M. J. Nat. Rev. Drug Discov. 2008, 7 (11), 900-907.
Aslanidis, C.; de Jong, P. J. Nucleic Acids Res. 1990, 18 (20), 6069-6074.
Baugh, L.; Phan, I.; Begley, D. W.; Clifton, M. C.; Armour, B.; Dranow, D. M.; Taylor, B. M.; Muruthi, M. M.; Abendroth, J.; Fairman, J. W.; Fox, D.; Dieterich, S. H.; Staker, B. L.; Gardberg, A. S.; Choi, R.; Hewitt, S. N.; Napuli, A. J.; Myers, J.; Barrett, L. K.; Zhang, Y.; Ferrell, M.; Mundt, E.; Thompkins, K.; Tran, N.; Lyons-Abbott, S.; Abramov, A.; Sekar, A.; Serbzhinskiy, D.; Lorimer, D.; Buchko, G. W.; Stacy, R.; Stewart, L. J.; Edwards, T. E.; Van Voorhis, W. C.; Myler, P. J. Tuberculosis 2015, 95 (2), 142-148.
Bedell, V. M.; Westcot, S. E.; Ekker, S. C. Brief. Funct. Genomics 2011, 10 (4), 181-188.
Berman, H. M.; Westbrook, J.; Feng, Z.; Gilliland, G.; Bhat, T. N.; Weissig, H.; Shindyalov, I. N.; Bourne, P. E. Nucleic Acids Res. 2000, 28 (1), 235-242.
Burrowes, D.; Boyer, K.; Swisher, C. N.; Noble, A. G.; Sautter, M.; Heydemann, P.; Rabiah, P.; Lee, D.; McLeod, R.; the Toxoplasmosis Study Group. J. Neuroparasitology 2012, 3 (2012).
Caumes, E.; Bocquet, H.; Guermonprez, G.; Rogeaux, O.; Bricaire, F.; Katlama, C.; Gentilini, M. Clin. Infect. Dis. 1995, 21 (3), 656-658.
CDC—Toxoplasmosis.

Chen, V. B.; Arendall, W. B.; Headd, J. J.; Keedy, D. A.; Immormino, R. M.; Kapral, G. J.; Murray, L. W.; Richardson, J. S.; Richardson, D. C. Acta Crystallogr. Sect. D Biol. Crystallogr. 2010, 66 (1), 12-21.
Christen, P.; Metzler, D. E. Transaminases; Wiley: New York, 1985.
Cirak, S.; Arechavala-Gomeza, V.; Guglieri, M.; Feng, L.; Torelli, S.; Anthony, K.; Abbs, S.; Garralda, M. E.; Bourke, J.; Wells, D. J.; Dickson, G.; Wood, M. J.; Wilton, S. D.; Straub, V.; Kole, R.; Shrewsbury, S. B.; Sewry, C.; Morgan, J. E.; Bushby, K.; Muntoni, F. Lancet 2011, 378 (9791), 595-605.
Dabritz, H. A.; Miller, M. A.; Atwill, E. R.; Gardner, I. A.; Leutenegger, C. M.; Melli, A. C.; Conrad, P. A. J. Am. Vet. Med. Assoc. 2007, 231 (11), 1676-1684.
Daune, G.; Seiler, N. Neurochem. Res. 1988, 13 (1), 69-75.
Davis, I. W.; Leaver-Fay, A.; Chen, V. B.; Block, J. N.; Kapral, G. J.; Wang, X.; Murray, L. W.; Arendall, W. B.; Snoeyink, J.; Richardson, J. S.; Richardson, D. C. Nucleic Acids Res. 2007, 35 (suppl 2), W375-W383.
Dubey, J. P. J. Parasitol. 1998, 84 (4), 862-865.
Emsley, P.; Cowtan, K. Acta Crystallogr. Sect. D Biol. Crystallogr. 2004, 60 (12), 2126-2132.
Emsley, P.; Lohkamp, B.; Scott, W. G.; Cowtan, K. Acta Crystallogr. Sect. D Biol. Crystallogr. 2010, 66 (4), 486-501.
Frey, P. A.; Ables, R. H. Enzymatic Reaction Mechanisms; Oxford University Press, USA, 2006.
Gafan, C.; Wilson, J.; Berger, L. C.; Berger, B. J. Mol. Biochem. Parasitol. 2001, 118 (1), 1-10.
Hawker, D. D. Ph.D. Diss. Northwest. Univ. 2013.
Hill, D.; Dubey, J. P. Clin. Microbiol. Infect. 2002, 8 (10), 634-640.
Holm, L.; Rosenström, P. Nucleic Acids Res. 2010, 38, W545-W549.
Jk, Frenkel.; A, R.; M, C. Am. J. Trop. Med. Hyg. 1975, 24 (3), 439-443.
Johnson, J. D.; Dennull, R. A.; Gerena, L.; Lopez-Sanchez, M.; Roncal, N. E.; Waters, N. C. Antimicrob. Agents Chemother. 2007, 51 (6), 1926-1933.
Jortzik, E.; Fritz-Wolf, K.; Sturm, N.; Hipp, M.; Rahlfs, S.; Becker, K. J. Mol. Biol. 2010, 402 (2), 445-459.
Juncosa, J. I.; Lee, H.; Silverman, R. B. Anal. Biochem. 2013, 440 (2), 145-149.
Jung, M. J.; Seiler, N. J. Biol. Chem. 1978, 253 (20), 7431-7439.
Kabsch, W. Acta Crystallogr. Sect. A 1976, 32 (5), 922-923.
Kiianitsa, K.; Solinger, J. A.; Heyer, W.-D. Anal. Biochem. 2003, 321 (2), 266-271.
Lai, B.-S.; Witola, W. H.; Bissati, K. El; Zhou, Y.; Mui, E.; Fomovska, A.; McLeod, R. Proc. Natl. Acad. Sci. 2012, 201208775.
Laskowski, R. A.; MacArthur, M. W.; Moss, D. S.; Thornton, J. M. J. Appl. Crystallogr. 1993, 26 (2), 283-291.
Laskowski, R. A.; Watson, J. D.; Thornton, J. M. Nucleic Acids Res. 2005, 33 (Web Server), W89-W93.
Lee, H.; Juncosa, J. I.; Silverman, R. B. Med. Res. Rev. 2015, 35 (2), 286-305.
Liu, W.; Peterson, P. E.; Carter, R. J.; Zhou, X.; Langston, J. A.; Fisher, A. J.; Toney, M. D. Biochemistry 2004, 43 (34), 10896-10905.
Lu, H.; Silverman, R. B. J. Med. Chem. 2006, 49 (25), 7404-7412.
Madej, T.; Lanczycki, C. J.; Zhang, D.; Thiessen, P. A.; Geer, R. C.; Marchler-Bauer, A.; Bryant, S. H. Nucleic Acids Res. 2014, 42 (D1), D297-D303.
Magariños, M. P.; Carmona, S. J.; Crowther, G. J.; Ralph, S. A.; Roos, D. S.; Shanmugam, D.; Voorhis, W. C. Van; Agüero, F. Nucleic Acids Res. 2012, 40 (D1), D1118-D1127.
Markova, M.; Peneff, C.; Hewlins, M. J. E.; Schirmer, T.; John, R. A. J. Biol. Chem. 2005, 280 (43), 36409-36416.
McCoy, A. J.; Grosse-Kunstleve, R. W.; Adams, P. D.; Winn, M. D.; Storoni, L. C.; Read, R. J. J. Appl. Crystallogr. 2007, 40 (4), 658-674.
McLeod, R.; Khan, A. R.; Noble, G. A.; Latkany, P.; Jalbrzikowski, J.; Boyer, K. Pediatr. Infect. Dis. J. 2006, 25 (3), 270-272.
McLeod, R.; Lykins, J.; Noble, A. G.; Rabiah, P.; Swisher, C. N.; Heydemann, P. T.; McLone, D.; Frim, D.; Withers, S.; Clouser, F.; Boyer, K. Curr. Pediatr. Rep. 2014, 2 (3), 166-194.

(56) References Cited

OTHER PUBLICATIONS

McNicholas, S.; Potterton, E.; Wilson, K. S.; Noble, M. E. M. Acta Crystallogr. D. Biol. Crystallogr. 2011, 67 (Pt 4), 386-394.
Mehta, P. K.; Hale, T. I.; Christen, P. Eur. J. Biochem. 1993, 214 (2), 549-561.
Michaelis, L.; Menten, M. L.; Johnson, K. A.; Goody, R. S. Biochemistry 2011, 50 (39), 8264-8269.
Minor, W.; Cymborowski, M.; Otwinowski, Z.; Chruszcz, M. Acta Crystallogr. Sect. D Biol. Crystallogr. 2006, 62 (8), 859-866.
Montoya, J. G.; Liesenfeld, O. Lancet 2004, 363 (9425), 1965-1976.
Morris, R. J.; Perrakis, A.; Lamzin, V. S. In Methods in Enzymology; Elsevier, 2003; vol. 374, pp. 229-244.
Moulton, H. M.; Moulton, J. D. Biochim. Biophys. Acta—Biomembr. 2010, 1798 (12), 2296-2303.
Murshudov, G. N.; Skubák, P.; Lebedev, A. A.; Pannu, N. S.; Steiner, R. A.; Nicholls, R. A.; Winn, M. D.; Long, F.; Vagin, A. A. Acta Crystallogr. Sect. D Biol. Crystallogr. 2011, 67 (4), 355-367.
Neafsey, D. E. Nat. Genet. 2013, 45 (6), 589-590.

\* cited by examiner

INACTIVATORS OF TOXOPLASMA GONDII ORNITHINE AMINOTRANSFERASE FOR TREATING TOXOPLASMOSIS AND MALARIA

CROSS-REFERENCE TO RELATED PATENT APPLICATIONS

The present application is a divisional of U.S. Ser. No. 15/728,714, filed Oct. 10, 2017, which claims the benefit of priority under 35 U.S.C. § 119(e) to U.S. Provisional Application 62/406,104, filed on Oct. 10, 2016, the contents of which are incorporated herein by reference in their entireties.

STATEMENT REGARDING FEDERALLY SPONSORED RESEARCH OR DEVELOPMENT

This invention was made with government support under R01 DA030604 awarded by the National Institutes of Health. The government has certain rights in the invention.

BACKGROUND

The field of the invention relates to compounds that selectively inactivate and/or inhibit *Toxoplasma gondii* ornithine aminotransferase (TgOAT). In particular, the field of the invention relates to selective inactivators and/or inhibitors of TgOAT for the treatment for the treatment of infection associated with *Toxoplasma gondii* and/or *Plasmodium falciparum*.

Toxoplasmosis, the disease caused by the parasite *Toxoplasma gondii* (*T. gondii*), is the leading cause of death attributed to food-borne illness in the United States. It is estimated that this parasite infects between 30 and 50% of the world population. One potential therapeutic target in the fight against this parasite is ornithine aminotransferase (TgOAT), a pyridoxal 5'-phosphate (PLP)-dependent enzyme that plays a crucial role in preventing toxic accumulation of ornithine in the cell. A selective inhibition of OAT in *T. gondii* over human OAT is highly desired in either eliminating the growth of the parasites or preventing the shedding of long lived and persisting infectious oocysts into the environment. We have characterized a number of features of TgOAT: the gene, protein, abundance in different life cycle stages, and enzyme activity. A screening of our library of 23 GABA analogues resulted in several selective inactivators of TgOAT. Crystal structures of the native and inactivated enzymes were obtained. Two different inactivation mechanisms of two different inactivators were identified: one by gabaculine, which inactivated the enzyme by forming an aromatic ring inside the active site, which created a large energy barrier to reversal and put the product in a deep thermodynamic well, and the other by (S)-4-amino-5-fluoropentanoic acid, which inactivated the enzyme by forming a covalent adduct to the enzyme. These newly identified TgOAT inactivators and insights of the enzyme binding pocket from crystal structures lay a foundation of further studies of selective inactivation of TgOAT and drug development.

SUMMARY

Disclosed are methods, compounds, and compositions for treating infection by an Apicomplexan parasite that include administering a compound that selectively inactivates ornithine aminotransferase of the Apicomplexan parasite. Specifically, the methods, compounds, compounds may be utilized for treating infection by *Toxoplasma gondii* and toxoplasmosis and for treating infection by *Plasmodium falciparum* and malaria. The compounds disclosed herein are observed to selectively inactivate *Toxoplasma gondii* ornithine aminotransferase (TgOAT) relative to human OAT and relative to human γ-aminobutyric aminotransferase (GABA-AT).

DETAILED DESCRIPTION

Figure 1:
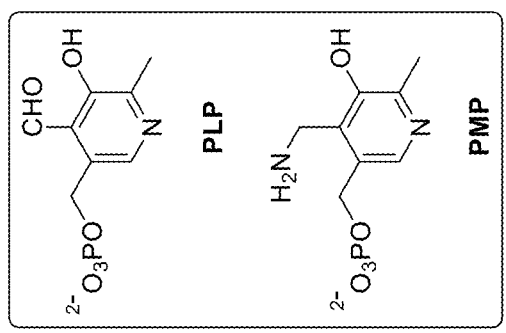
FIG. 1. The catalytic reactions of OAT.
Figure 1:
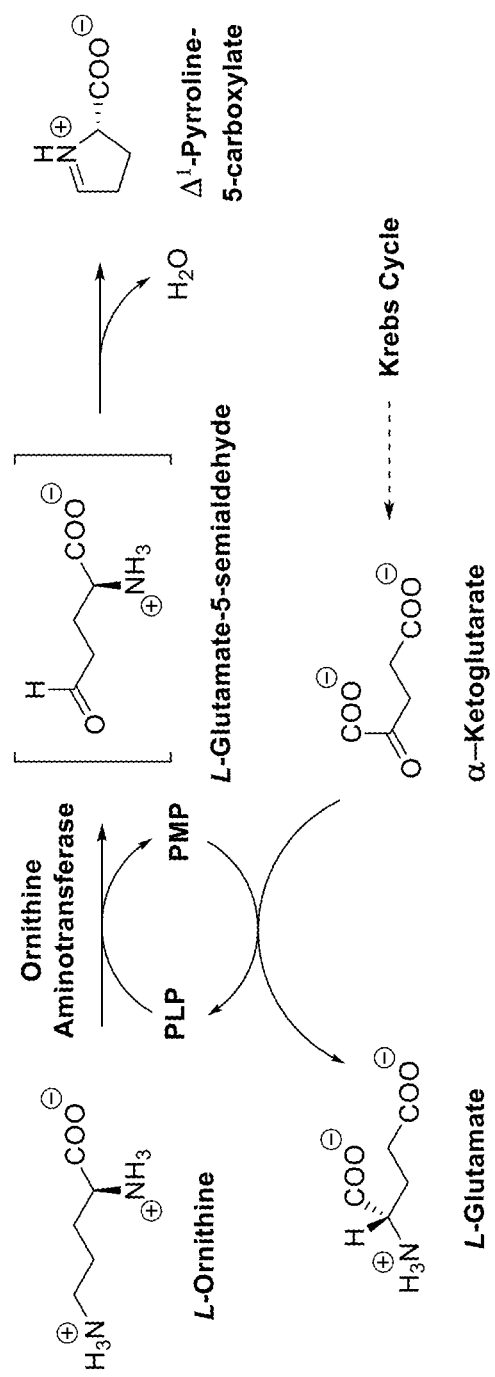

The present invention is described herein using several definitions, as set forth below and throughout the application.

Unless otherwise specified or indicated by context, the terms "a", "an", and "the" mean "one or more." For example, "a compound" should be interpreted to mean "one or more compounds."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

The term "alkyl" as contemplated herein includes a straight-chain or branched alkyl radical in all of its isomeric forms. Similarly, the term "alkoxy" refers to any alkyl radical which is attached via by an oxygen atom (i.e., a radical represented as "alkyl-O—*").

As used herein, a "patient" may be interchangeable with "subject" or "individual" and means an animal, which may be a human or non-human animal, in need of treatment.

A "patient in need of treatment" may include a patient having or at risk for developing a disease, disorder, or condition that is associated with infection by an Apicomplexan parasite. A "patient in need of treatment" may include a patient having or at risk for developing a disease, disorder, or condition that is associated with infection by *Toxoplasma gondii, Plasmodium falciparum, Hammondia hammondi*, or *Neospora caninum*. For example, a "patient in need of treatment" may include a patient having or at risk for developing toxoplasmosis and/or malaria.

The disclosed methods, compounds, and compositions may be effective in inhibiting infection by an Apicomplexan parasite. The disclosed methods, compounds, and compositions may be effective in inhibiting infection by *Toxoplasma gondii, Plasmodium falciparum, Hammondia hammondi*, and/or *Neospora caninum*. For example, the disclosed methods, compounds, and compositions may be effective in inhibiting replication, shedding, and/or transmission of *Toxoplasma gondii, Plasmodium falciparum, Hammondia hammondi*, and/or *Neospora caninum* by inactivating OAT of *Toxoplasma gondii* (i.e., TgOAT) and/or OAT of *Plasmodium falciparum* (i.e., PJOAT), and or OAT of *Hammondia hammondi* (i.e., HhOAT), and/or *Neospora caninum* (i.e., NcOAT), for example, where the disclosed compounds are observed to selectively inactivate TgOAT. The amino acid sequence of TgOAT (SEQ ID NO:1), PJOAT (SEQ ID NO:2), HhOAT (SEQ ID NO:3), and NcOAT (SEQ ID NO:4) display significant percentage sequence identity.

Inhibitors of human OAT have been disclosed in the art. (See U.S. Provisional Patent Application No. 61/787,409; Zigmond et al., "Suppression of Hepatocellular Carcinoma by Inhibition of Overexpressed Ornithine Aminotransferase," ACS Med. Chem. Lett. 2015, 6, 840-844, published on May 29, 2015); and Zigmond et al., U.S. Published Application No. 2012/0245380, published on Sep. 27, 2012; the contents of which are incorporated herein by reference in their entireties). Compounds that inhibit and/or inactivate human OAT may be modified for use in the disclosed methods (e.g., as derivative compounds that inactivate TgOAT and/or PJOAT and/or HhOat and/or NcOat). As discussed herein, OAT is a pyridoxal 5' phosphate (PLP)-dependent enzyme. Selective targeting of pyridoxal 5' phosphate (PLP)-dependent enzymes has been reported. (See Mascarenhas et al., "Selective Targeting by a Mechanism-Based Inactivator against Pyridoxal 5'-Phosphate-Dependent Enzymes: Mechanisms of Inactivation and Alternative Turnover," Biochem. 2017 Sep. 19; 56(37):4951-4961; the content of which is incorporated herein by reference in its entirety).

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

The formulae of the compounds disclosed herein should be interpreted as encompassing all possible stereoisomers, enantiomers, or epimers of the compounds unless the formulae indicates a specific stereoisomer, enantiomer, or epimer. The formulae of the compounds disclosed herein should be interpreted as encompassing salts, esters, amides, or solvates thereof of the compounds.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 µM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Selective Inactivators of Apicomplexan Ornithine Aminotransferase

The technology of this application relates to selective inactivators of apicomplexan ornithine aminotransferases and has numerous applications, including but not limited to: (i) developing treatments for toxoplasmosis and malaria; (ii) discovering new compounds for studying inactivation of *Toxoplasma gondii* ornithine aminotransferase for further drug development.

The Apicomplexan parasites *Toxoplasma gondii* and *Plasmodium falciparum* are major causes of morbidity and mortality worldwide. Toxoplasmosis, the disease caused by *T. gondii*, is the leading cause of death attributed to foodborne illness in the United States. Globally, this parasite infects between 30 and 50% of the population. This means that approximately two billion people have this parasite living within their brains, with largely unknown consequences. Comprising a public health threat, toxoplasmosis could result in a wide range of serious health problems, including blindness and neurological disease in congenital infection and severe meningoencephalitis in immunocompromised persons. The parasite *P. falciparum* also causes significant human suffering. In 2013, there were 584,000 deaths, with 78% occurring in children younger than 5 years of age. Like the cat vector for *Toxoplasma*, the malaria vector, the *Anopheles* mosquito, transmits a disease that remains a substantial threat to human health.

Current therapeutics for *T. gondii* and *P. falciparum* have limitations, including toxicity, hypersensitivity reactions, an inability to eliminate the latent, encysted bradyzoite life stage of *T. gondii*, and drug resistance of malaria. For these reasons, new therapeutic approaches are needed.

One molecular target has been identified on the basis of several characteristics, including computed druggability, phylogenetic data, assayability, and potential of structure determination: the mitochondrial matrix enzyme ornithine aminotransferase (OAT). OAT is a pyridoxal 5'-phosphate (PLP)-dependent enzyme that catalyzes the conversion of L-ornithine to L-glutamate-5-semialdehyde, which spontaneously cyclizes to form Δ1-pyrroline-5-carboxylate. One main role of OAT is to prevent toxic accumulation of ornithine in the cell. In human, a deficiency of OAT is known to cause gyrate atrophy of the choroid and retina, but high levels of the enzyme impair the detoxification of ammonia by ornithine carbamoyltransferase, through the urea cycle. A selective inhibition of *T. gondii* OAT and *P. falciparum* OAT over human OAT would potentially lead to a toxic accumulation of ornithine only in the parasites.

While human OAT has been well studied and characterized, and has demonstrated to be a high therapeutic target, our knowledge of *T. gondii* OAT and *P. falciparum* OAT is severely limited, with the current understanding being based on parallels to other species. While the kinetic and crystallographic analysis of PfOAT was characterized previously, TgOAT has not been characterized, structurally or functionally, or studied for its potential as a molecular target in this parasite. No selective inhibitors of TgOAT had been identified to target any of the parasite life cycle stages. It has been known that expression of TgOAT was ~256 times higher in sporozoites than in tachyzoites and bradyzoites; therefore, even if this molecular target was not critical for tachyzoites or bradyzoites, targeting the formation of the environmentally-resistant oocyst life cycle stage could have a significant impact on disrupting the chain of transmission and, thereby, decrease the consequent morbidity and mortality.

We have identified for the first time several selective irreversible inhibitors, a.k.a. inactivators, of TgOAT that could be used for studying selective inactivation of TgOAT for further drug development. We also characterized a number of features of TgOAT: the gene, protein, abundance in different life cycle stages, and enzyme activity We obtained the crystal structure of the native TgOAT and the crystal structures of two different types of inactivated TgOAT: one by gabaculine, which inactivated the enzyme by forming an aromatic ring inside the active site, which created a large energy barrier to reversal and put the product in a deep thermodynamic well, and the other by (S)-4-amino-5-fluoropentanoic acid, which inactivated the enzyme by forming a covalent adduct to the enzyme.

In summary, we have identified for the first time several selective irreversible inhibitors, a.k.a. inactivators, of TgOAT that could be used for studying selective inactivation of TgOAT for further drug development. We also characterized a number of features of TgOAT: the gene, protein, abundance in different life cycle stages, and enzyme activity. We obtained the crystal structure of the native TgOAT and the crystal structures of two different types of inactivated TgOAT: one by gabaculine, which inactivated the enzyme by forming an aromatic ring inside the active site, which created a large energy barrier to reversal and put the product in a deep thermodynamic well, and the other by (S)-4-amino-5-fluoropentanoic acid, which inactivated the enzyme by forming a covalent adduct to the enzyme.

ILLUSTRATIVE EMBODIMENTS

The following embodiments are illustrative and should not be interpreted to limit the claimed subject matter of this patent application.

In some embodiments, the subject matter of this application relates to methods, compounds, and compositions for treating a subject infected with an Apicomplexan parasite such as *Toxoplasma gondii* and *Plasmodium falciparum*. The disclosed methods may include administering to the subject an effective amount of a compound that selectively inactivates ornithine aminotransferase of *Toxoplasma gondii* (TgOAT) and/or *Plasmodium falciparum*.

In some embodiments of the disclosed methods, the compound has a formula:

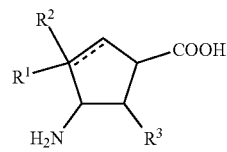

wherein:
$R^1$ and $R^2$ are hydrogen, halo, or a C1-C6 alkyl which may be straight or branched and optionally may be substituted at one or more positions with halo; or $R^1$ and $R^2$ together form a C1-C6 alkenyl group optionally substituted at one or more positions with halo or C1-C6 haloalkyl (e.g., trifluoromethyl); and
$R^3$ is hydrogen or halo.

Specifically, the compound utilized in the disclosed methods may have a formula selected from:

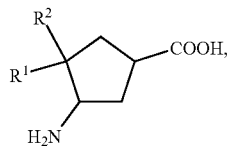

or the stereisomer

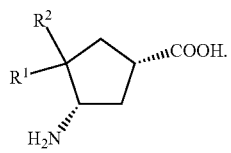

Specifically, the compound may have a formula:

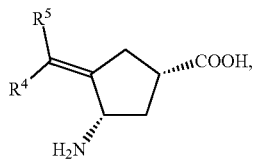

wherein $R^4$ and $R^5$ are hydrogen, halo, or C1-C6 haloalkyl (e.g., trifluoromethyl).

More specifically, the compound utilized in the disclosed methods may have a formula selected from the group consisting of:

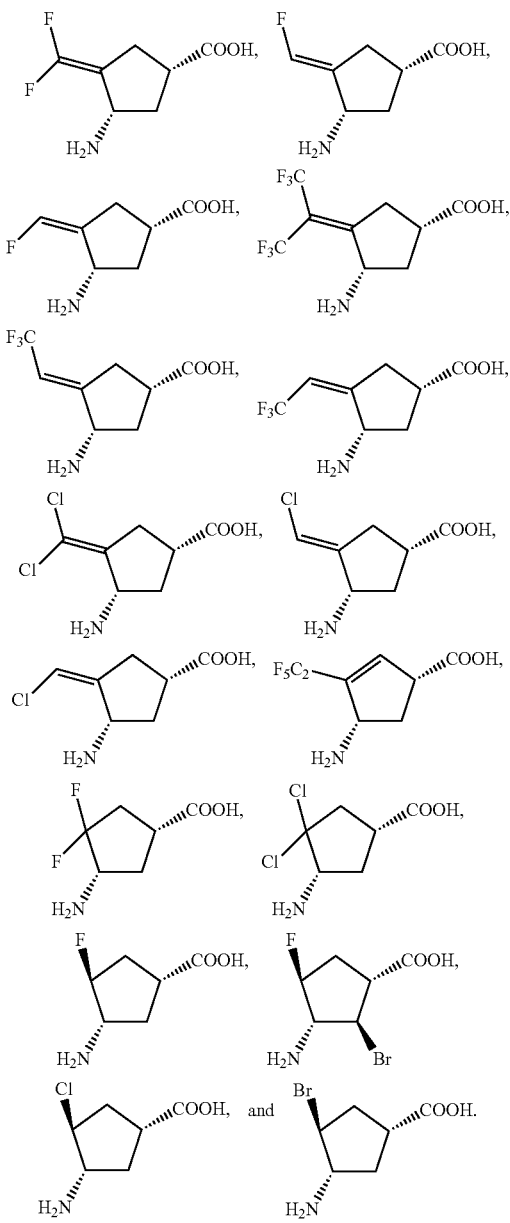

In other embodiments of the disclosed methods, the compound may have a formula:

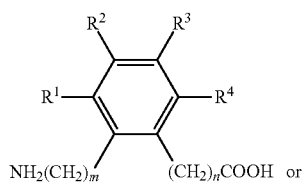

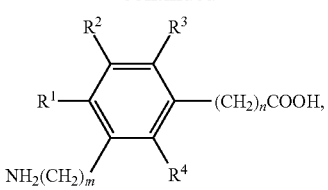

wherein:

m is 1-6;

n is 0-6; and $R^1$, $R^2$, $R^3$ and $R^4$ may be the same or different and are selected from hydrogen, halo, and C1-C6 alkyl which may be straight chain or branched and may be substituted at one or more positions with halo.

Specifically, the compound utilized in the disclosed methods may have a formula:

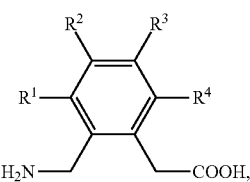

and more specifically

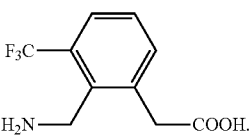

Specifically, the compound utilized in the disclosed methods may have a formula:

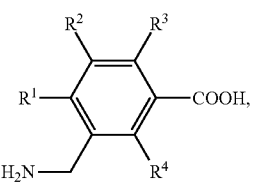

and more specifically

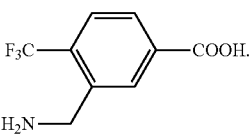 [SMILES: NCc1cc(C(=O)O)ccc1C(F)(F)F]

Specifically, the compound utilized in the disclosed methods may have a formula:

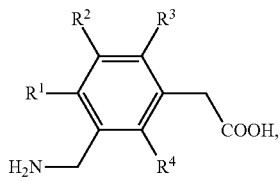

and more specifically

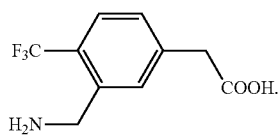

In other embodiments of the disclosed methods, the compound may have a formula:

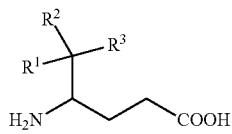

wherein:
X is O, S, or N;
$R^1$, $R^2$, and $R^3$ are the same or different and are hydrogen, halo, or C1-C6 alkyl.

Specifically, the compound utilized in the disclosed methods may have a formula selected from:

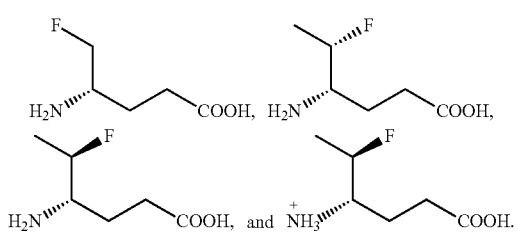

In other embodiments of the disclosed methods, the compound may have a formula:

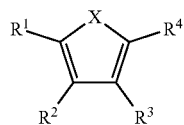

wherein:
X is O, S, or N;
$R^1$ and $R^2$ are hydrogen or C1-C6 amino alkyl; and
$R^3$ and $R^4$ are hydrogen or C1-C6 carboxyl.

Specifically, the compound utilized in the disclosed methods may have a formula selected from the group consisting of:

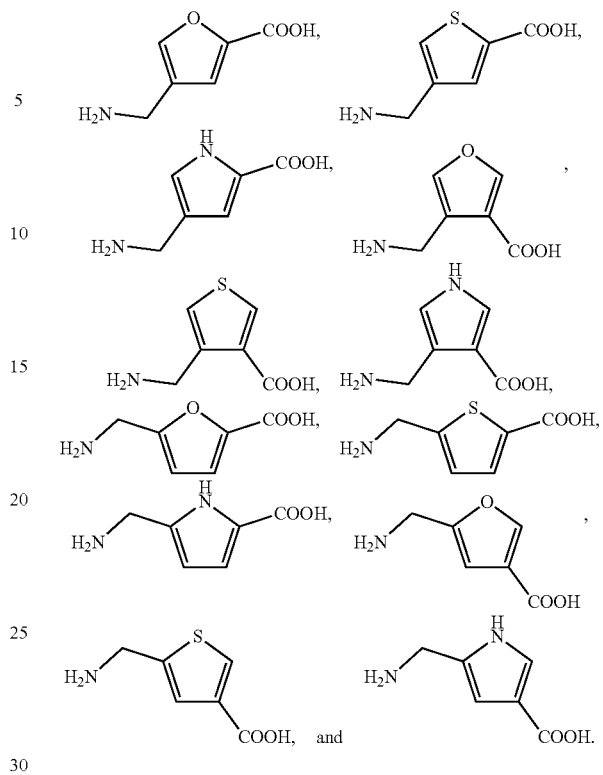

Preferably, the compound disclosed for use in the methods of treatment selectively inactivates TgOAT versus human OAT and versus human GABA-AT. In some embodiments, the compound selectively inactivates TgOAT and has a $k_{inact}/K_i$ (min$^{-1}$ mM$^{-1}$) that is greater than about 1, 2, 5, 10, 20, 50, 100, 200, 500, 1000, 2000, 5000, or greater, or has a $k_{inact}/K_i$ (min$^{-1}$ mM$^{-1}$) within a range bounded by any of these values (e.g., a $k_{inact}/K_i$ (min$^{-1}$ mM$^{-1}$) of 20-2000).

Preferably, the compound does not inactivate human OAT. If the compound does inactivate human OAT, preferably the compound inactivates human OAT and has a $k_{inact}/K_i$ (min$^{-1}$ mM$^{-1}$) that is less than about 0.5, 0.2, 0.1, 0.05, 0.02, 0.01, 0.005, 0.002, 0.001, or lower, or has a $k_{inact}/K_i$ (min$^{-1}$ mM$^{-1}$) within a range bounded by any of these values (e.g., a $k_{inact}/K_i$ (min$^{-1}$ mM$^{-1}$) of 0.05-0.005).

Preferably, the compound does not inhibit human OAT. If the compound does inhibit human OAT, preferably the compound has a $K_i$ with respect to inhibiting OAT that is greater than about 0.01 mM, 0.02 mM, 0.05 mM, 0.1 mM, 0.2 mM, 0.5 mM, 1 mM, 2 mM, 10 mM or higher, or has a $K_i$ within a range bounded by any of these values (e.g., a $K_i$ of 1-10 mM).

Preferably, the compound does not inactivate human GABA-AT. If the compound does inactivate human GABA-AT, preferably the compound has a $k_{inact}/K_i$ (min$^{-1}$ mM$^{-1}$) with respect to inactivating GABA-AT that is less than about 0.5, 0.2, 0.1, 0.05, 0.02, 0.01, 0.005, 0.002, 0.001, or lower, or has a $k_{inact}/K_i$ (min$^{-1}$ mM$^{-1}$) within a range bounded by any of these values (e.g., a $k_{inact}/K_i$ (min$^{-1}$ mM$^{-1}$) of 0.05-0.005).

Preferably, the compound does not inhibit human GABA-AT. If the compound does inhibit human GABA-AT, preferably the compound has a $K_i$ with respect to inhibiting GABA-AT that is greater than about 0.01 mM, 0.02 mM, 0.05 mM, 0.1 mM, 0.2 mM, 0.5 mM, 1 mM, 2 mM, 10 mM or higher, or has a $K_i$ within a range bounded by any of these values (e.g., a $K_i$ of 1-10 mM).

Also disclosed herein are new compounds which may be utilized to inhibit TgOAT and pharmaceutical compositions comprising the new compounds together with a suitable pharmaceutical carrier, excipient, and/or diluent. In some embodiments, the disclosed new compounds may have a formula:

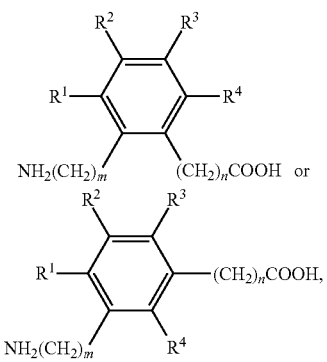

wherein:
m is 1-6;
n is 0-6; and
$R^1$, $R^2$, $R^3$ and $R^4$ may be the same or different and are selected from hydrogen, halo, and C1-C6 alkyl which may be straight chain or branched and may be substituted at one or more positions with halo.

Specifically, the new compound may have a formula:

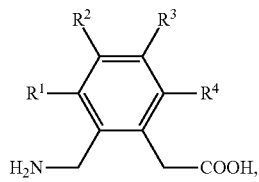

or more specifically

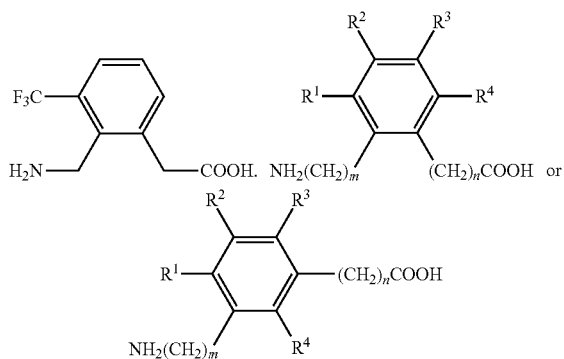

wherein:
m is 1-6;
n is 0-6; and
$R^1$, $R^2$, $R^3$ and $R^4$ may be the same or different and are selected from hydrogen, halo, and C1-C6 alkyl which may be straight chain or branched and may be substituted at one or more positions with halo.

Specifically, the new compound may have a formula:

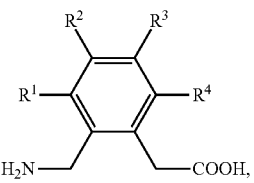

and more specifically

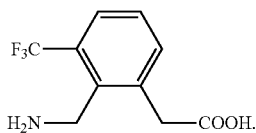

Specifically, the new compound may have a formula:

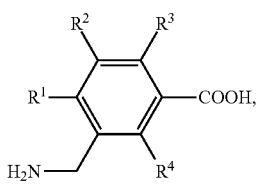

and more specifically

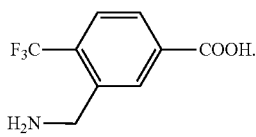

Specifically, the compound may have a formula:

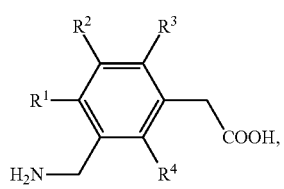

and more specifically

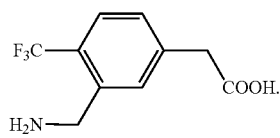

EXAMPLES

The following Examples are illustrative and are not intended to limit the scope of the claimed subject matter.

Example 1

Title: 4-Amino-5-Fluorohexanoic Acid Inhibitors of Ornithine Aminotransferase

Reference is made to U.S. Provisional Patent Application No. 61/787,409, entitled "4-Amino-Fluorohexanoic Acid Inhibitors of Ornithine Aminotransferase," filed on Mar. 15, 2013, now expired (hereinafter "the '409 Provisional Application"), which content is incorporated herein by reference in its entirety. A copy of the '409 Provisional Application was included and as Appendix I to U.S. Provisional Patent Application No. 62/406,104, filed on Oct. 10, 2016, to which the present application claims the benefit of priority under 35 U.S.C. 119(e) and which is incorporated by reference in the present application in its entirety. The '409 Provisional Application discloses inhibitors of OAT which may be used in the methods disclosed in the present application or which inhibitors of OAT may be modified for use in the methods disclosed in the present application. The '409 Provisional Application also discloses methods of synthesizing inhibitors of OAT, which methods may be used to synthesize the compounds disclosed for use in the present application or which methods for synthesizing inhibitors of OAT may be modified for use in synthesizing the compounds disclosed for use in the present application.

This example relates to compound of a formula:

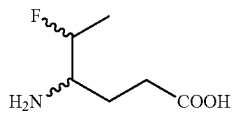

and salts, hydrates, and solvates thereof.

In certain embodiments, such a compound may be selected from:

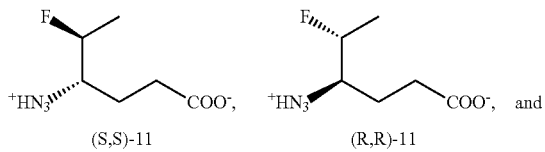

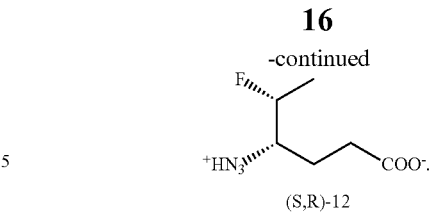

Regardless, the compounds of this example are without stereochemical limitation. As illustrated and discussed below, such compounds and/or their intermediates are available as single enantiomers, racemic mixtures from which isomers can be resolved, or diastereomers from which the corresponding enantiomers can be separated. Accordingly, any stereocenter can be (S) or (R) with respect to any other stereocenter(s). As a separate consideration, various compounds can be present as an acid salt, either partially or fully protonated. In certain such embodiments, the counterion(s) can be a conjugate base of a protic acid. Further, it will be understood by those skilled in the art that any one or more the compounds of this invention can be provided as part of a pharmaceutical composition comprising a pharmaceutically-acceptable carrier component for use in conjunction with a treatment method or medicament.

In part, the present invention can also be directed to a method inhibiting an ornithine aminotransferase. Such a method can comprise providing a compound of this invention, whether or not part of a pharmaceutical composition, and administering an effective amount of such a compound for contact with an ornithine aminotransferase, such as an ornithine aminotransferase of a Apicomplexan parasite (e.g., ornithine aminotransferase of *Toxoplasma gondii* (TgOAT) or *Plasmodium falciparum*: (PJOAT).

Inhibitors of aminotransferases are known in the art. For example, Vigabatrin 2 (i.e., 4-am inohex-5-enoic acid) is known to inhibit γ-aminobutyric acid aminotransferase (GABA-AT), which catalyzes the transformation of GABA into succinic semialdehyde. Inhibition of GABA-AT by vigabatrin has been shown to involve two distinct mechanisms (Scheme 1).

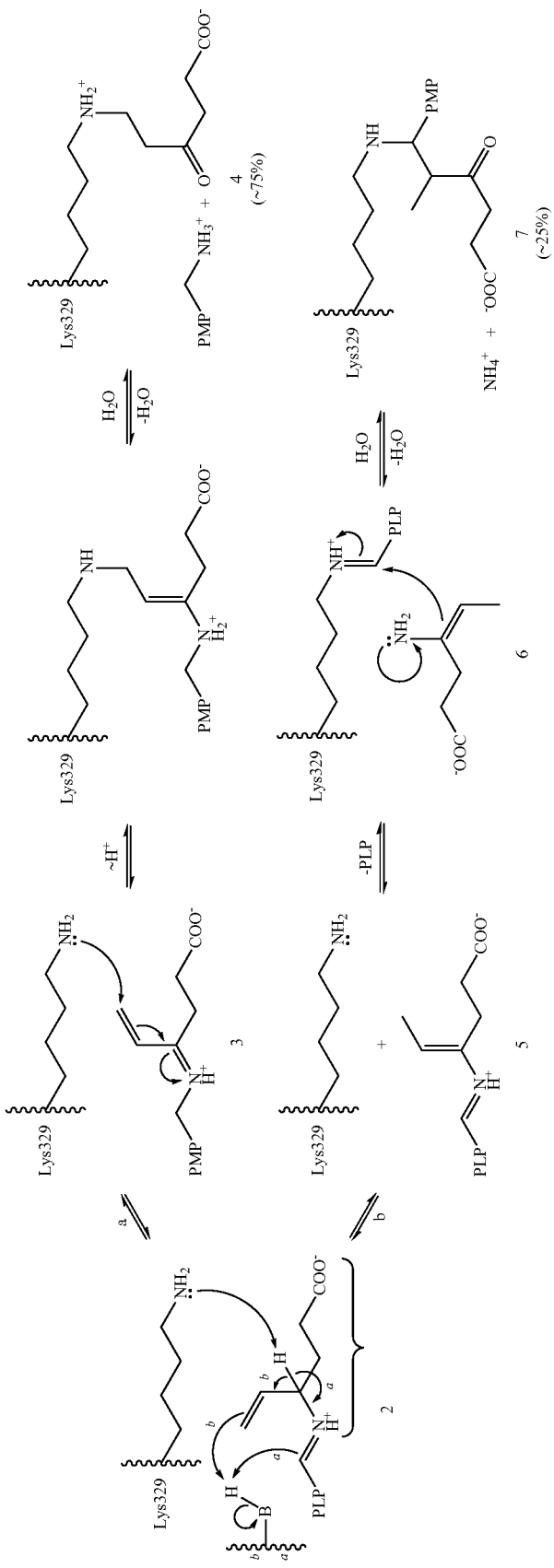
Scheme 1. Mechanisms of inactivation of GABA-AT by vigabatrin (2).

As indicated in Scheme 1, after the formation of a Schiff base between the drug and the cofactor pyridoxal phosphate (PLP), Lys329 (the previous anchor point for the aldehyde) deprotonates the γ-proton, and tautomerizes the complex in two ways (pathways a and b). Pathway "a" creates a Michael acceptor moiety in the substrate (3); Lys329 undergoes 1,4-addition to give 4. Pathway "b" involves tautomerization through the alkene, leading to enamine adduct 5, which releases enamine 6 that reattaches to the PLP to give 7. The observed products of the reaction were determined to be in the ratio of ~75% for the Michael addition pathway and ~%25 for the enamine pathway.

5-Fluoro-4-aminopentanoic acid 8 has long been known as a very efficient inactivator of GABA-AT that inhibits the enzyme exclusively through a mechanism (Scheme 2, R=H) that involves Schiff base formation with pyridoxal phosphate (PLP) followed by elimination of HF to 9 (R=H), leading only to the enamine pathway (10, R=H).

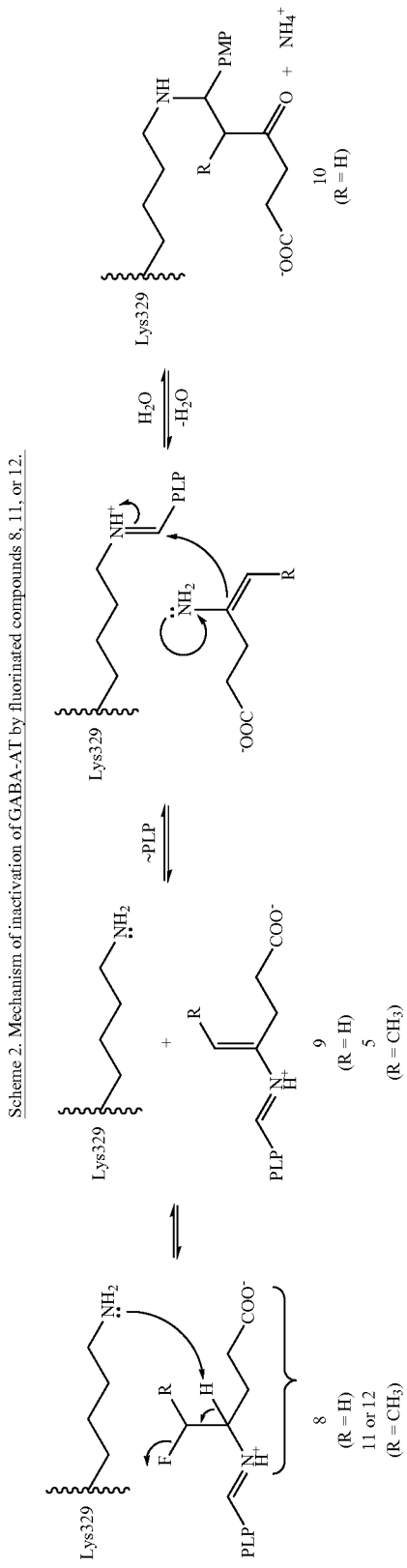

In view of this mechanism outlined in Scheme 2, 11 and 12 were synthesized, where 11 and 12 are identical to 8 except for the addition of a gem-methyl group on the carbon with the fluorine atom. However, elimination of HF from 11 or 12 would lead to an identical enamine intermediate (5, Scheme 1) found by tautomerization of 2. If so, then 11 or 12 would be a vigabatrin mimic that proceeds exclusively by vigabatrin's minor enamine pathway (pathway b, Scheme 1). This is depicted in Scheme 2, where R=CH₃ (compare 9, R=CH₃ to 5 in Scheme 1).

Off-target effects of 8 are significant, especially at glutamate decarboxylase (GAD, required for GABA synthesis) and, to a lesser extent, at aspartate aminotransferase (AspAT). Vigabatrin (2), which is based on a hexanoic acid skeleton, shows no activity at GAD and weakly affects Asp-AT. It was, therefore, thought that hexanoic acids 11 and/or 12 could be not only inactivators of GABA-AT, but also of OAT—while displaying improved enzyme selectivity when compared to their shorter chain analogue 8.

The devised synthetic route was based around the asymmetric dihydroxylation/lactonization of a hexenoate ester and involved the use of azide as a nitrogen source, as well as a benzyl ester as a carboxylate protecting group. These choices were made to simplify the isolation and purification of the zwitterion after the final hydrogenolysis; under these conditions, only simple recrystallization was required instead of ion exchange chromatography (Scheme 3).

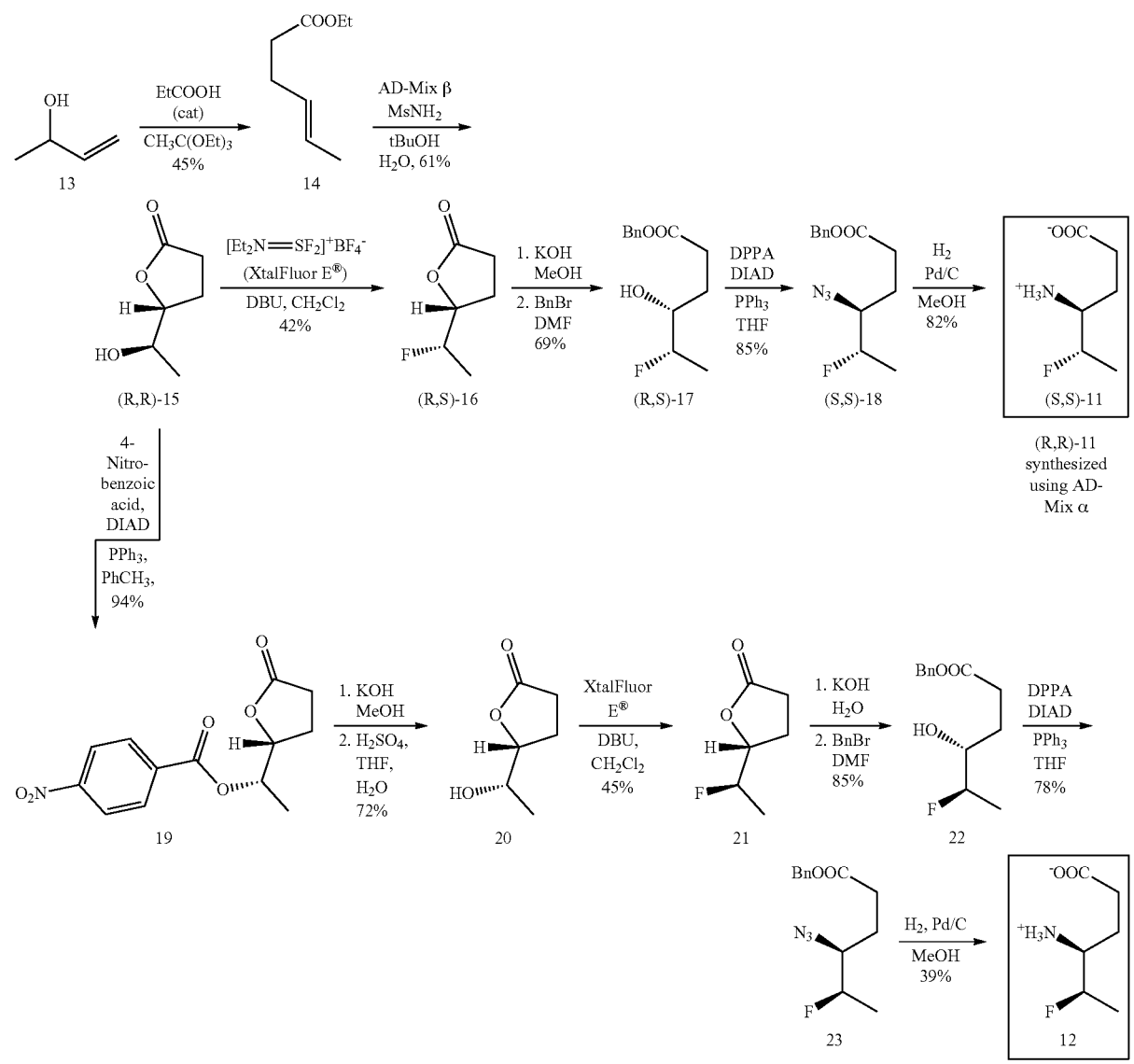

Scheme 3. Synthesis of fluorinated GABA analogues 11 and 12.

The synthesis of (S,S)-11, (R,R)-11, and 12, started with the Claisen-Johnson rearrangement of 3-buten-2-ol (13) and triethyl orthoacetate. The continuous removal of ethanol during this reaction, which was reported to result in good yields, led to the formation of product 14 along with its corresponding 3-buten-2-ol ester; however, this mixture was difficult to separate, and yields were low as a result.

Asymmetric dihydroxylation/lactonization of unsaturated ester 14 led to hydroxyethyl butenolide (R,R)-15, the key intermediate of this synthesis. Fluorination of this compound using XtalFluor E® ((diethylamino)difluorosulfonium tetrafluoroborate) and DBU (1,8-diazabicycloundec-7-ene) yielded intermediate (R,S)-16, which was hydrolyzed under basic conditions and esterified to give acyclic fluorinated alcohol (R,S)-17.

The hydroxyl group in (R,S)-17 was replaced by azide under Mitsunobu conditions using DPPA (diphenylphosphoryl azide) and DIAD (diisopropyl azodicarboxylate), and the resulting azide (S,S)-18 was hydrogenated to give final compound (S,S)-11. The chiral purity of the product was determined by derivatization as the Mosher amide, and was found to have 92% ee.

Compound (R,R)-11 was obtained in a manner similar to that of its enantiomer, but using AD-Mix a instead of its counterpart, and DAST (diethylaminosulfurtrifluoride) instead of XtalFluor E® for the fluorination step.

The synthesis of compound 12 was initially attempted through the double inversion of ent-17 to give 23. However, with prospects for a better result, efforts were shifted toward the inversion of (R,R)-15 via a Mitsunobu protocol. Although the reaction with picolinic acid was not productive, the use of 4-nitrobenzoic acid was successful.

After subjecting diester 19 to literature conditions designed to obtain butenolide 20 exclusively (free from the competing tetrahydropyrone product), only the desired product was obtained in a good yield. Fluorination of this compound led to 21, and the synthesis was completed as before (Scheme 3).

The enantiomer of 12 was not synthesized because it is known that active GABA compounds of this type have S stereo chemistry at the amine carbon. Therefore, while available through the strategy outlined above, the R isomer was not a particularly attractive synthetic target to warrant additional effort.

Materials and Methods $^1$H NMR and $_{13}$C NMR spectra were recorded on a Bruker Avance III 500 MHz spectrometer. $^{19}$F NMR spectra were obtained on an Agilent DDR2 400 MHz spectrometer. Chemical shifts for are reported as δ values in ppm relative to tetramethylsilane ($^1$H, $^{13}$C) or CFCl$_3$ ($^{19}$F), with the CHC$_3$ signal arbitrarily set as 7.27 ($^1$H) or 77.0 ($^{13}$C) ppm. Melting points were determined in a Bichi B540 melting point apparatus using open capillary tubes, and are uncorrected. Mass spectra were obtained with a Thermo Finnigan LCQ electrospray impact low resolution mass spectrometer, or an Agilent LC-TOF 6210 (accurate mass), using 1:1 dichloromethane/methanol as an eluent. Optical rotations were measured in an Optical Activity Limited AA-100 polarimeter, using a 0.5 dm, 1.3 mL cell. Column chromatography was performed with Sorbent Technologies silica gel, (60 Å pore size, 230×400 mesh) or on an Agilent 971-FP machine using pre-packed 50 silica columns (Analogix, Silicycle, or Agilent). Thin layer chromatography was carried out using Baker-Flex® plastic-backed plates coated with silica gel IB2 and fluorescent indicator. Purity was determined on an Agilent 1260 reverse phase analytical HPLC, using evaporative light scattering detection (Agilent 385 ELSD); a C18 column (Gemini® 5 m NX, 110 Å pore size, 50×4.6 mm size) was used with 5% acetonitrile in water (0.05% TFA) as the mobile phase (0.8 mL/min).

All reagents were purchased from Aldrich, and were used as received, except when noted. Solvents were dried using cartridge-filled drying trains.

NMR spectra were analyzed with the help ofMNova 7 (MestreLab Research, Santiago de Compostela, Spain, http://mestrelab.com).

Synthetic Procedures and Characterization (E)-Ethyl hex-4-enoate (14)

Neat propionic acid (126.2 µL, 125.2 mg, 1.681 mmol) was added to a mixture of 3-buten-2-ol (25.00 g, 336.3 mmol) and triethyl orthoacetate (100 mL, 86.73 g, 534.6 mmol) in a 3-necked flask fitted with a reflux condenser over a liquid addition funnel. The magnetically stirred solution was heated to 135° C. under nitrogen. Every 2 h, the funnel was closed and a sample of the condensate was analyzed by NMR. When no more starting alcohol was found in the distillate, the reaction was brought to room temperature and water (30 mL) was added. Stirring was continued for 30 min, and the low-boiling components were distilled off with minimal vacuum, using an additional 30 mL ethanol to remove residual water. Then, a higher vacuum was applied to distill the product. Column chromatography (20% dichloromethane in hexanes) led to the product (21.535 g, 151.44 mmol, 45%) as a clear, volatile liquid, and significant amounts of 3-buten-2-yl hex-4-enoate as a side product (yield not determined). (Spectral data not shown.)

(R)-5-((R)-1-Hydroxyethyl)dihydrofuran-2(3H)-one ((R,R)-15)

To a vigorously stirred mixture of AD-mix$^{15}$ β (26.61 g, Sigma-Aldrich) and methanesulfonamide (1.864 g, 19.01 mmol) in t-BuOH/H20 (1:1, 100 mL) at 4° C., was added unsaturated ester 14 (3.00 mL, 2.703 g, 19.01 mmol). Stirring was continued at that temperature for 4 days. At this point, the reaction was complete by TLC (1:1 EtOAc/hexanes) and solid NaHSO$_3$ (30 g) was added. After stirring for another 1 h, the suspension had turned white and was partitioned between water and ethyl acetate (50 mL each). The aqueous phase was then extracted with ethyl acetate (3×50 mL), and the combined organic fractions were dried (Na$_2$SO$_4$), filtered, and the solvent removed. The crude was subjected to column chromatography (20% EtOAc in hexanes and 0-5% MeOH in CH$_2$Cl$_2$), leading to the product (1.506 g, 11.57 mmol, 61%) as a clear oil. (Spectral data not shown.)

(S)-5-((S)-1-Hydroxyethyl)dihydrofuran-2(3H)-one ((S,S)-15)

This compound was synthesized similarly to (R,R)-15, but using AD-Mix a. From 5.079 g (35.71 mmol) of ester 10, 3.011 g (23.14 mmol, 65%) of product were obtained. (Spectral data not shown.)

(R)-5-((S)-1-Fluoroethyl)dihydrofuran-2(3H)-one ((R,S)-16)

Alcohol (R,R)-15 (0.4073 g, 3.130 mmol) in CH$_2$Cl$_2$ (10 mL) at −78° C. was added DBU (716 µL, 0.729 mg, 4.69 mmol), followed by XtalFluor-E® ((diethylamino)difluorosulfonium tetrafluoroborate) (1.075 g, 4.695 mmol). After 30 min, the reaction was allowed to reach room temperature, and stirring was continued for 24 h. Then, 5% aqueous NaHCO$_3$ (10 mL) was added, and after stirring another 15 min, the aqueous layer was extracted with CH$_2$Cl$_2$ (2×10 mL). The combined organic phases were dried (MgSO$_4$), filtered through a pad of silica gel with abundant CH$_2$Cl$_2$, and the solvent was removed. Column chromatography (10-30% ethyl acetate in hexanes) gave the product (0.1721 g, 1.303 mmol, 42%) as a clear oil. (Spectral data not shown.)

(S)-5-((R)-1-Fluoroethyl)dihydrofuran-2(3H)-one ((S,R)-16)

To a solution of alcohol (S,S)-15 (1.859 g, 14.29 mmol) in dichloromethane (15 mL) at 0° C., was added DAST (2.37 mL, 2.91 g, 17.1 mmol) dropwise. The reaction was allowed to reach room temperature over 16 h with magnetic stirring. Again at 0° C., saturated aqueous NaHCO$_3$ (15 mL) was added slowly, and the mixture was extracted with dichloromethane (3×15 mL). The combined organic extracts were dried (MgSO$_4$), the solvent removed, and the crude subjected to column chromatography (10-30% ethyl acetate in hexanes), giving the product (0.4959 g, 1.888 mmol, 26%) as a clear oil. (Spectral data not shown.)

(4R,5S)-Benzyl 5-fluoro-4-hydroxyhexanoate ((R,S)-17)

To a solution of lactone (R,S)-16 (0.1557 g, 1.178 mmol in MeOH (5 mL) was added solid KOH (0.0777 g, 1.25 mmol), and the reaction was stirred at room temperature for 16 h. The solvent was then evaporated under reduced pressure; then the solid was redissolved in DMF (5 mL) and treated with benzyl bromide (0.143 mL, 0.206 g, 1.18 mmol) dropwise. After another 16 h of stirring, the reaction was diluted with water (10 mL) and extracted with Et$_2$O (3×10 mL). The organic extracts were washed with water (2×5 mL), dried (Na$_2$SO$_4$), and concentrated under reduced pressure. Column chromatography (10-40% ethyl acetate in hexanes) yielded the product (0.2522 g, 1.050 mmol, 89%) as a clear oil. (Spectral data not shown.)

(4S,5R)-Benzyl 5-fluoro-4-hydroxyhexanoate ((S,R)-17)

This compound was synthesized by the same method as that for (R,S)-17 from lactone (S,R)-16 (0.4463 g, 3.378 mmol), obtaining the product (0.7403 g, 3.081 mmol, 91%) as a clear oil. (Spectral data not shown.)

(4S,5S)-Benzyl 4-azido-5-fluorohexanoate ((S,S)-18)

DIAD (0.200 mL, 0.205 g, 0.964 mmol) was slowly added to a stirred solution of alcohol (R,S)-17 (0.1931 g, 0.8037 mmol), triphenylphosphine (0.2555 g, 0.9644 mmol), and diisopropylethylamine (0.140 mL, 0.104 g, 0.804 mmol) in THF (5 mL) at 10° C., and stirring was continued for 15 min. Diphenylphosphoryl azide (0.214 mL, 0.274 g, 0.964 mmol) was then added slowly at −15° C., and the reaction was allowed to reach room temperature overnight. The solvent was removed under reduced pressure, and the crude product was directly subjected to column chromatography (dichloromethane) to give the product (0.1742 g, 0.6747 mmol, 85%) as a clear oil. (Spectral data not shown.)

(4R,5R)-Benzyl 4-azido-5-fluorohexanoate ((R,R)-18)

This compound was obtained through the procedure used for (S,S)-18, starting from (S,R)-17 (0.2008 g, 0.8357 mmol), and yielding the product (0.1898 g, 0.7155 mmol, 86%) as a clear oil. (Spectral data not shown.)

(4S,5S)-4-Ammonio-5-fluorohexanoate ((S,S)-11)

Azido ester (S,S)-18 (0.1414 g, 0.5330 mmol) was dissolved in methanol (12 mL) and 10% Pd/C (27 mg, 0.025 mmol) was added. The flask was flushed under vacuum and filled with hydrogen three times. A hydrogen-filled balloon was fitted to the sealed flask through a needle, and stirring was continued for 24 hat room temperature. At that time, the suspension was filtered through a pad of Celite with additional methanol (50 mL). Solvent and volatiles were removed from the filtrate under high vacuum. The crude product was recrystallized from methanol and diethyl ether to give the product (64.9 mg, 0.435 mmol, 82%) as a white solid, mp. 135-137° C., $[\alpha]^{25}$+41° (c=0.36, MeOH); HRMS (ESI) (m/z): 150.0927 (calc, for C$_6$H1$_3$FNO$_2$+: 150.0925, [M+H]$^+$); ee=92% (from Mosher amide de); HPLC purity (retention time): 95% (0.784 min). (NMR data not shown).

(4S,5S)-5-Fluoro-4-((S)-3,3,3-trifluoro-2-methoxy-2-phenylpropanamido) hexanoic acid (R)-(−)-a-Methoxy-α-(trifluoromethyl)phenylacetyl chloride (7.4 µL, 9.9 mg, 39 µmol) was added to a magnetically stirred solution of amine (S,S)-11 (5 0.8 mg, 39 mol) and NaHCO$_3$ (98 mg, 1.2 mmol) in water and acetone (1.5 mL each). After stirring overnight at room temperature, the mixture was evaporated under reduced pressure, and 3M aqueous HCl (3 mL) was added. Extraction with CH$_2$Cl$_2$ (2×3 mL) and CHCl$_3$ (3 mL), followed by drying (Na2S04), filtration, and evaporation gave the product (14.2 mg, 38.9 µmol, 100%) as a clear oil. (Spectral data not shown.)

(4R,5R)-4-Ammonio-5-fluorohexanoate ((R,R)-11)

Using the same procedure as that for (S,S)-11, azide (R,R)-18 (0.1658 g, 0.6250 mmol) yielded the product (78.3 mg, 0.5249 mmol, 84%) as a white powder, mp. 131-132° C., $[\alpha]^{25}$−44° (c=0.22, CD$_3$OD); HRMS (ESI) (m/z): 150.0926 (calc, for C$_6$H1$_3$FNO$_2$+: 150.0925, [M+H]$^+$); ee=84% (from Mosher amide de); HPLC purity (retention time): 94% (0.790 min). (Other spectral data not shown.)

(4R,5R)-5-Fluoro-4-((S)-3,3,3-trifluoro-2-methoxy-2-phenylpropanamido) hexanoic acid This compound was prepared exactly as the derivative of product (S,S)-11, but using amine (R,R)-7 (5.6 mg, 38 µmol) and giving the product (13.2 mg, 36.1 µmol, 96%) as a clear oil, contaminated with (S)-Mosher's acid (3 0.1 mg, 13 0.2 µmol). (Spectral data not shown.)

(S)-1-((R)-5-Oxotetrahydrofuran-2-yl)ethyl 4-nitrobenzoate (19)

A magnetically-stirred suspension of alcohol (R,R)-15 (0.4981 g, 3.827 µmmol), triphenylphosphine (1.318 g, 4.976 mmol), and 4-nitrobenzoic acid (0.8485 g, 4.976 mmol) in toluene (10 mL) at 0° C. and under nitrogen, was treated dropwise with neat diisopropyl azodicarboxylate (1.1 mL, 1.1 g, 5.0 mmol). The reaction was allowed to reach room temperature overnight, and the solids were removed using a plug of cotton, washing with an additional 10 mL of toluene. The crystalline product was redissolved with ethyl acetate (10 mL) and the solvent was removed. The toluene solution was also evaporated under reduced pressure, and the resulting crude product was subjected to column chromatography (20-50% ethyl acetate in hexanes), giving the product as a white solid (total yield: 1.005 g, 3.599 mmol, 94%), mp: 136-138° C. (Spectral data not shown.)

(R)-5-((S)-1-Hydroxyethyl)dihydrofuran-2(3H)-one (20)

Diester 19 (0.9751 g, 3.492 mmol) was dissolved in EtOH (15 mL) at room temperature, and KOH (1.350 g, 21.65 mmol) was added. The reaction was stirred at 60° C. for 2 h, and, after cooling back to room temperature, the solvent was removed under reduced pressure. The residue was redissolved in THF and H$_2$O (25 mL each), and H$_2$SO$_4$ (2.3 mL, 4.2 g, 43 mmol) was added slowly. After stirring at room temperature for 24 h, the reaction was extracted with ethyl acetate (3×50 mL), and the combined extracts were dried (Na$_2$SO$_4$) and the solvent was removed. Column chromatography (30-50% ethyl acetate in hexanes) gave the product (0.3272 g, 2.514 mmol, 72%) as a clear oil. (Spectral data not shown.)

(R)-5-((R)-1-Fluoroethyl)dihydrofuran-2(3H)-one (21)

This compound was prepared as detailed for (R,S)-16, from lactone 20 (0.3167 g, 2.434 mmol), yielding the product (0.1162 g, 0.8794 mmol, 45%) as a clear oil. (Spectral data not shown.)

(4R,5R)-Benzyl 5-fluoro-4-hydroxyhexanoate (22)

This compound was obtained similarly to (R,S)-17, from lactone 21 (0.1032 g, 0.7810 mmol), giving the desired ester (0.1597 g, 0.6647 mmol, 85%) as a clear oil. (Spectral data not shown.)

(4S,5R)-Benzyl 4-azido-5-fluorohexanoate (23)

This compound was obtained similarly to (S,S)-18, starting from alcohol 22 (0.1425 g, 0.5931 mmol), giving the product (0.1228 g, 0.4629 mmol, 78%) as a clear oil. (Spectral data available, but not shown.)

(4S,5R)-4-Ammonio-5-fluorohexanoate (12)

This compound was synthesized by the same route as for compound (S,S)-11, using azido ester 23 (0.1063 g, 0.4007 mmol), and obtaining the product (23.2 mg, 0.156 mmol, 39%) as a white solid, mp 158-159° C., $[\alpha]^{25}$+15° (c=0.24, CD$_3$OD); HRMS (ESI) (m/z): 150.0925 (calcd for C$_6$H$_{13}$FNO$_2$+: 150.0925, [M+H]$^+$); ee=93% (from Mosher amide de); HPLC purity (retention time): 94% (0.794 min). (NMR data not shown.)

(4R,5R)-5-Fluoro-4-((S)-3,3,3-trifluoro-2-methoxy-2-phenylpropanamido) hexanoic acid This compound was prepared exactly as the derivative of product (S,S)-11, but using amine 12 (6.1 mg, 41 μmol) and giving the product (13.6 mg, 37.3 μmol, 91%) as a clear oil, contaminated with (S)-Mosher's acid (2.7 mg, 11.3 μmol). (Spectral data not shown.)

Example 2

Reference is made to Zigmond et al., "Suppression of Hepatocellular Carcinoma by Inhibition of Overexpressed Ornithine Aminotransferase," ACS Med. Chem. Lett. 2015, 6, 840-844, published on May 29, 2015 (hereinafter "Zigmond 2015"), the content of which is incorporated herein by reference in its entirety. Reference also is made to U.S. Published Application No. 2012/0245380, published on Sep. 27, 2012, (hereinafter Zigmond 2012), the content of which is incorporated herein by reference in its entirety. Zigmond 2015 and Zigmond 2012 disclose the synthesis of inhibitors of OAT which may be used in the methods disclosed in the present application or which may be modified for use in the methods disclosed in the present application.

Example 3

Title: Synthesis of Haloalkyl-, Aminoalkyl-, Carboxylalkyl-, and/or Carboxyl-Substituted Benzene Compounds Compounds for use in the methods disclosed herein may include substituted benzene compounds, such as of haloalkyl-, aminoalkyl-, carboxylalkyl-, and/or carboxyl-substituted benzene compounds. In particular, compounds for use in the methods disclosed herein may include substituted benzene compounds, such as

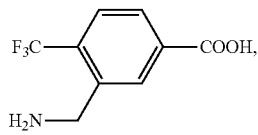 [SMILES: NCc1cc(C(=O)O)ccc1C(F)(F)F]

IV-10

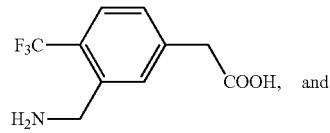

IV-11

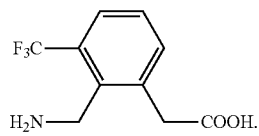

IV-12

Synthesis Schemes.

Synthesis of IV-10 (Scheme 4) began with commercially available 3-nitro-4-(trifluoromethyl)benzoic acid (IV-23). Esterification followed by catalytic hydrogenation provided methyl aminobenzoate IV-24. Installation of the nitrile was achieved via Sandmeyer reaction; however, obtaining an adequate and reproducible yield was difficult. A number of different reagents and conditions for this reaction were explored; most employing some form of copper (I), typically copper (I) cyanide. It was ultimately found, however, that a moderate yield could be reliably obtained by using copper (II) sulfate and potassium cyanide. The synthesis then proceeded with reduction and Boc protection of the nitrile to yield IV-26. Saponification of the ester followed by Boc deprotection of IV-27 gave the desired amino acid product (IV-10) as the hydrochloride salt.

Scheme 4. Synthesis of trifluoromethylbenzene amino acid IV-10.

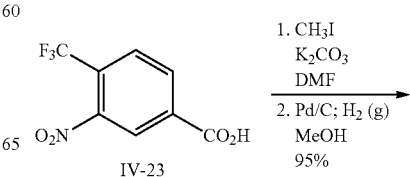

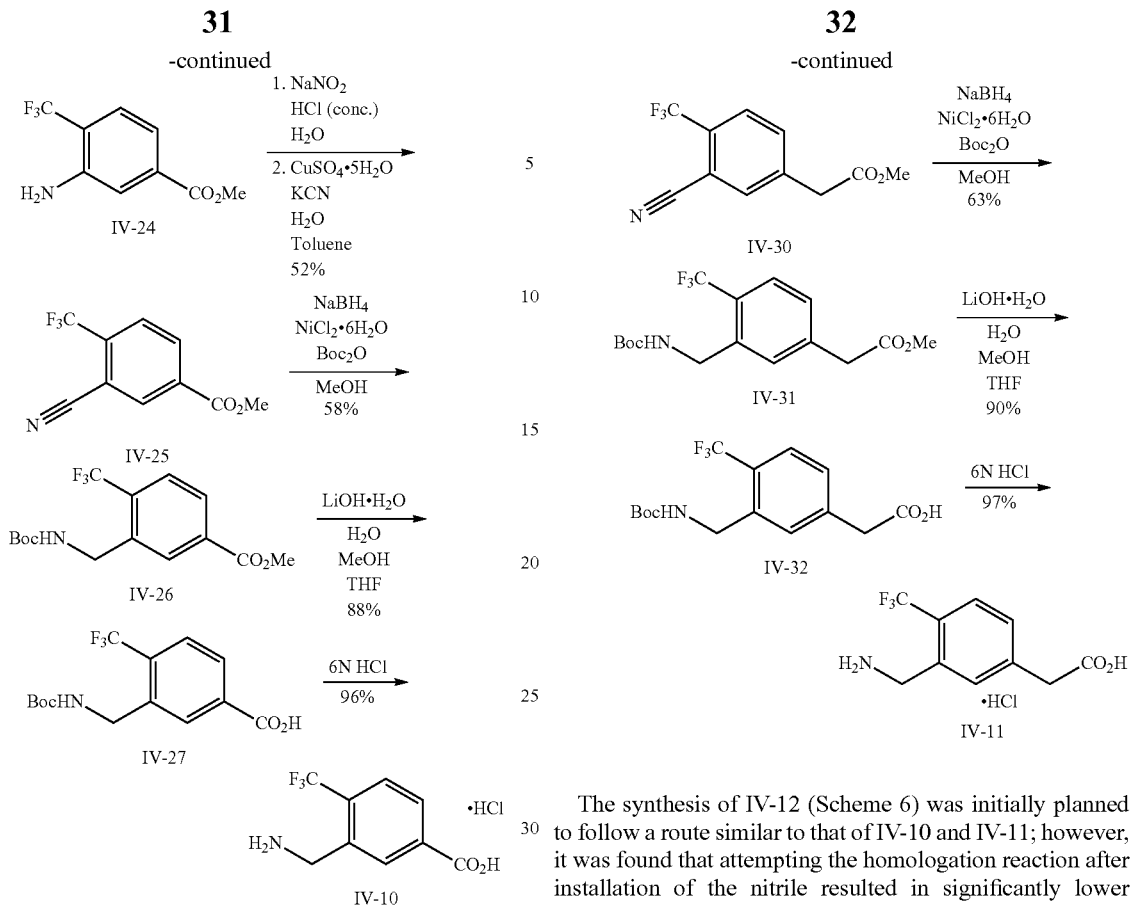

The synthesis of IV-11 also started with IV-23 and is shown in Scheme 5. After first performing an Arndt-Eistert homologation, the synthesis followed a route similar to the one used to generate IV-10. An effort was made to improve the yield of the homologation; however, yields remained consistently around 50%. Both TMSCHN$_2$ and freshly generated and distilled CH$_2$N$_2$ were evaluated, in addition to various reactions times, temperatures, and silver catalyst sources, but no significant improvement was observed.

Scheme 5. Synthesis of trifluoromethylbenzene amino acid IV-12.

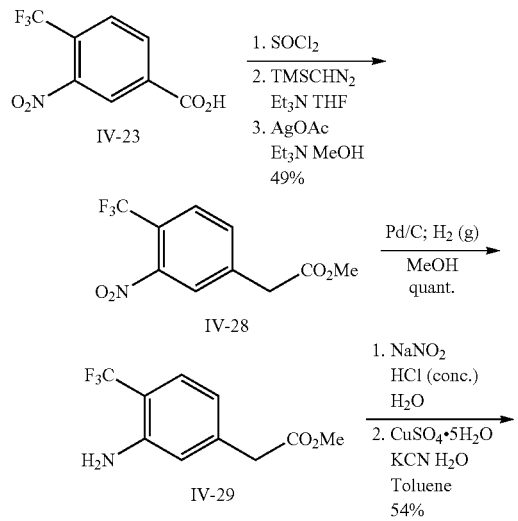

The synthesis of IV-12 (Scheme 6) was initially planned to follow a route similar to that of IV-10 and IV-11; however, it was found that attempting the homologation reaction after installation of the nitrile resulted in significantly lower yields, many side products, and loss of starting material. It is believed that the nitrile is labile under the acidic reaction conditions generated during formation of the acyl chloride intermediate. To circumvent this problem, amine IV-34 was substituted first with a bromide rather than a nitrile, then carried through the homologation to generate ester IV-37. Microwave assisted cyanation provided the desired nitrile (IV-38), which was then reduced and Boc protected to give IV-39. After ester hydrolysis, deprotection of the Boc group using 6 N HCl was attempted; however, formation of the lactam over the amino acid salt appeared to be more favorable under these conditions and was difficult to separate from the desired product. Trifluoroacetic acid (TFA) was instead used for the deprotection resulting in the desired product (IV-12) as the TFA salt.

Scheme 6. Synthesis of trifluoromethylbenzene amino acid IV-13.

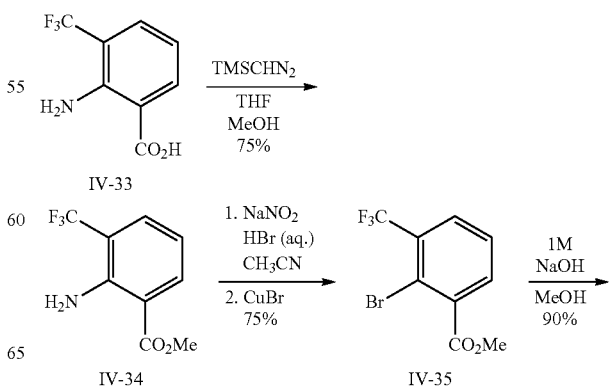

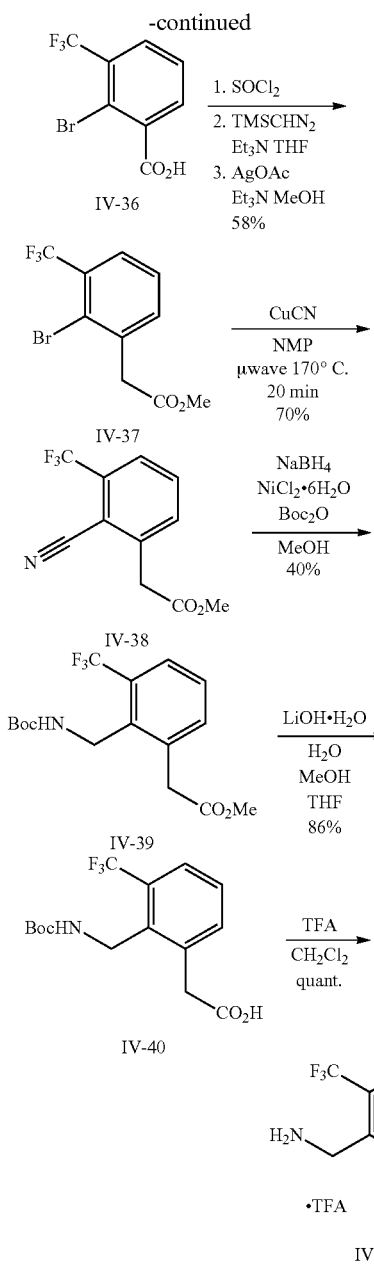

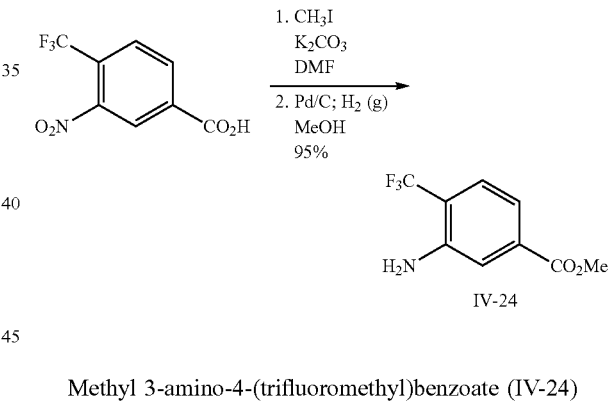

Methyl 3-amino-4-(trifluoromethyl)benzoate (IV-24)

General Methods.

Compounds IV-23 and IV-33 were purchased from Matrix Scientific. All other reagents were purchased from Sigma-Aldrich Company. All reagents were used as received. All syntheses were conducted under anhydrous conditions in an atmosphere of argon, using flame-dried apparatus and employing standard techniques in handling air-sensitive materials, unless otherwise noted. All solvents were distilled and stored under an argon or nitrogen atmosphere before use. Analytical thin layer chromatography was visualized by ultraviolet light. Flash column chromatography was carried out under a positive pressure of nitrogen. Reactions utilizing microwave irradiation were performed using a Biotage Initiator Microwave Synthesizer. $^1$H NMR and $^{13}$C NMR spectra were obtained with a Bruker AVANCE III 500 spectrometer. $^{19}$F NMR spectra were obtained with an Agilent DDR2 400 MHz spectrometer. $^1$H NMR spectra were recorded at 500 MHz and are presented as follows: chemical shift (in ppm on the δ scale relative to (=7.26 or 3.31 ppm for the solvent residual peaks in CDCl$_3$ or MeOD, respectively), integration, multiplicity (s=singlet, d=doublet, t=triplet, q=quartet, m=multiplet, br=broad), coupling constant (J/Hz). Coupling constants were taken directly from the spectra and are uncorrected. $^{13}$C NMR spectra were recorded at 126 MHz, and are presented as follows: chemical shift (in ppm on the δ scale relative to δ=77.16 or 49.00 ppm for the solvent residual peaks in CDCl$_3$ or MeOD, respectively), multiplicity, coupling constant (J/Hz). $^{19}$F NMR spectra were recorded at 376 MHz, and are presented as follows: chemical shift (in ppm on the δ scale relative to δ=0.00 ppm for the external standard peak of CFCl$_3$), multiplicity, coupling constant (J/Hz). High resolution mass spectra (HRMS) were measured with an Agilent 6210 LC-TOF (ESI, APCI, APPI) mass spectrometer. The purity of the synthesized final compounds was determined by HPLC analysis to be >95%. The column used was a Phenomenex Luna 5 am 200 Å, 4.6×250 mm. The column was thoroughly equilibrated at 100% solvent A, minimum 5 volumes. The compounds were eluted with a gradient from solvent A (90:10, CH$_3$CN:50 mM NH$_4$OAc pH 5.8) to solvent B (50:50, CH$_3$CN:10 mM NH$_4$OAc pH 5.8), 0-2.5 min, 0% B isocratic; 2.5-10 min, 0-100% B; 10-20 min, 100% B isocratic. Biochemical assays were performed using a Biotek Synergy H1 microplate reader. Prior to their evaluation, initial experiments were performed to confirm the synthesized analogues do not inhibit the coupling enzymes utilized in the substrate and inhibition assays.

Preparation and Characterization of New Compounds.

To a stirred solution of 3-amino-4-(trifluoromethyl)benzoic acid (IV-23, 2 g, 8.5 mmol) and K$_2$CO$_3$ (3.5 g, 25.5 mmol) in anhydrous DMF (10 mL) was added dropwise CH$_3$I (800 μL, 12.8 mmol). The reaction was stirred for 1 h then partitioned between EtOAc (100 mL) and water (100 mL). The organic phase was washed with water (3×50 mL), saturated aqueous NaHCO$_3$ (50 mL), dried (Na$_2$SO$_4$), and concentrated to dryness under reduced pressure. The crude product was dissolved in MeOH (20 mL) in the presence of 10% Pd/C (40 mg), placed under H$_2$ atmosphere and vigorously stirred overnight at room temp. The reaction mixture was then filtered through a Celite pad, concentrated in vacuo, and chromatographed (ethyl acetate/hexanes, 1:9) to yield the desired product as a clear oil (1.77 g, 95%). $^1$H NMR (500 MHz, CDCl$_3$) δ 7.48 (d, J=8.2 Hz, 1H), 7.42 (s, 1H), 7.39 (d, J=8.4 Hz, 1H), 4.30 (br s, 2H), 3.91 (s, 3H). $^{13}$C NMR (126 MHz, CDCl$_3$) δ 166.33 (s), 144.63 (s), 134.35 (s), 126.96 (q, J=5.1 Hz), 124.58 (q, J=272.6 Hz), 118.28 (s), 118.25 (s), 117.19 (q, J=30.2 Hz), 52.57 (s). $^{19}$F NMR (376 MHz, CDCl$_3$) δ−60.76 (s, 3F). HRMS [M-F]$^+$ Calcd for C$_9$H$_8$F$_3$NO$_2$ 200.0518; found 200.0527.

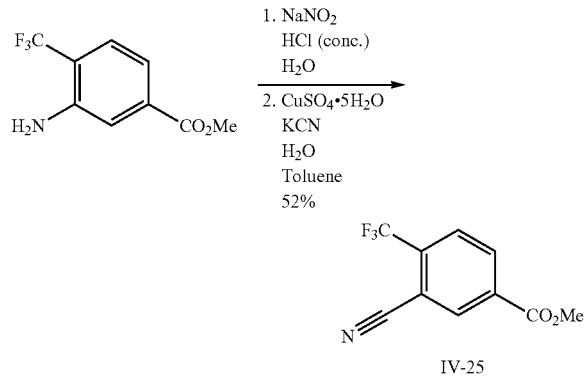

Methyl 3-cyano-4-(trifluoromethyl)benzoate (IV-25)

To a suspension of IV-24 (272 mg, 1.24 mmol) in conc. HCl (770 μL) cooled to 0° C. with stirring was added dropwise a solution of sodium nitrite (86 mg, 1.24 mmol) in water (700 μL) at such a rate to maintain a temperature below 5° C. After addition the reaction was stirred for 40 min then neutralized to pH 6 by the addition of Na$_2$CO$_3$ while still maintaining a temperature below 5° C. In a separate flask, a solution of potassium cyanide (372 mg, 5.70 mmol) in water (2 mL) was added portionwise to a stirred biphasic solution of copper (II) sulfate pentahydrate (372 mg, 1.49 mmol) in water (2 mL) and toluene (2 mL) at 0° C. then heated to 70° C. To this was added the diazonium salt solution dropwise while maintaining its temp at 0° C. After addition, the reaction was stirred at 70° C. for 1 h, cooled to room temp, and then separated between EtOAc (30 mL) and water (30 mL). The organic layer was washed with brine (10 mL), dried (Na$_2$SO$_4$), and concentrated to afford a crude dark brown oil that was purified by chromatography (ethyl acetate/hexanes, 1:9) to yield the desired product as a yellow oil (153 mg, 54%). $^1$H NMR (500 MHz, CDCl$_3$) δ 8.48 (s, 1H), 8.37 (d, J=7.5 Hz, 1H), 7.90 (d, J=8.2 Hz, 1H), 4.00 (s, 3H). $^{13}$C NMR (126 MHz, CDCl$_3$) δ 164.01 (s), 137.00-135.32 (m), 135.72 (s), 134.29 (s), 133.88 (s), 127.26 (q, J=4.6 Hz), 122.04 (q, J=274.3 Hz), 114.73 (s), 110.90 (s), 53.31 (s). 19F NMR (376 MHz, CDCl$_3$) δ−62.74 (s, 3F). HRMS [M+H]$^+$ Calcd for C$_{10}$H$_6$F$_3$NO$_2$ 230.0429; found 230.0424.

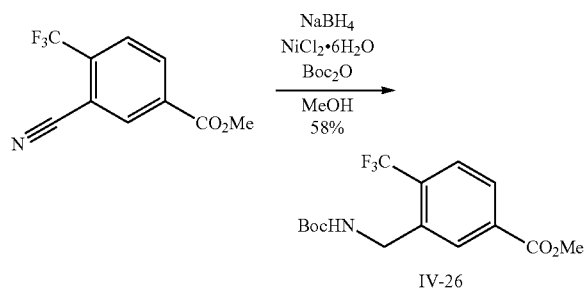

Methyl 3-(((tert-butoxycarbonyl)amino)methyl)-4-(trifluoromethyl)benzoate (IV-26)

Methyl 3-cyano-4-(trifluoromethyl)benzoate (IV-25, 142 mg, 0.62 mmol), Boc$_2$O (271 mg, 1.24 mmol), and NiCl$_2$.6H$_2$O (15 mg, 0.06 mmol) were dissolved in methanol and cooled to 0° C. with stirring. Sodium borohydride (164 mg, 4.32 mmol) was then added in portions over 30 min. After addition of sodium borohydride, the reaction was allowed to warm to room temp and stir for an additional hour. Diethylenetriamine (67 V L, 0.62 mmol) was added, and the mixture was allowed to stir for an additional 30 min before solvent evaporation. The crude residue was dissolved in EtOAc (20 mL) and washed with saturated aqueous NaHCO$_3$ (2×10 mL), dried (Na$_2$SO$_4$), concentrated under reduced pressure, and chromatographed (ethyl acetate/hexanes, 1:4) to afford the desired product as a yellow oil (130 mg, 63%). $^1$H NMR (500 MHz, CDCl$_3$) δ 8.18 (s, 1H), 8.00 (d, J=8.1 Hz, 1H), 7.70 (d, J=8.1 Hz, 1H), 5.12-4.93 (m, 1H), 4.54 (d, J=6.4 Hz, 2H), 3.93 (s, 3H), 1.46 (s, 9H). $^{13}$C NMR (126 MHz, CDCl$_3$) δ 165.93, 155.95, 138.28, 133.76, 131.66 (q, J=30.7 Hz), 130.33, 128.51, 126.37 (q, J=5.7 Hz), 123.99 (q, J=274.3 Hz), 80.16, 52.67, 41.07, 28.46. $^{19}$F NMR (376 MHz, CDCl$_3$) δ−60.91 (s, 3F). HRMS [M+Na]$^+$ Calcd for C$_{15}$H$_{18}$F$_3$NO$_4$ 356.1080; found 356.1084.

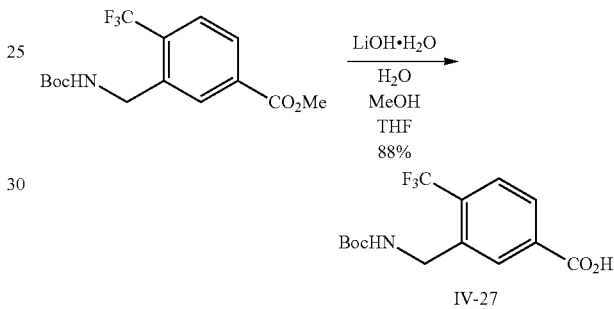

3-(((tert-Butoxycarbonyl)amino)methyl)-4-(trifluoromethyl)benzoic acid (IV-27)

To a solution of methyl 3-(((tert-butoxycarbonyl)amino)methyl)-4-(trifluoromethyl)benzoate (IV-26, 97 mg, 0.29 mmol) in MeOH (1 mL), THF (1 mL), and water (3 mL) was added LiOH*H$_2$O (24 mg, 0.58 mmol) and allowed to stir overnight. The reaction mixture was diluted in water (10 mL) and extracted with ether (2×10 mL), which was discarded. The aqueous phase was adjusted to pH 1 with 2 N HCl (aq.), and the resulting suspension was extracted with EtOAc (3×10 mL). The combined organics were washed with brine (10 mL), dried (Na$_2$SO$_4$), and evaporated under reduced pressure to yield the desired product as a white solid (83 mg, 90%). $^1$H NMR (500 MHz, CD$_3$OD) δ 8.19 (s, 1H), 8.03 (d, J=8.1 Hz, 1H), 7.78 (d, J=8.2 Hz, 1H), 4.48 (s, 2H), 1.48 (s, 9H). $^{13}$C NMR (126 MHz, CD$_3$OD) δ 168.39, 158.55, 139.97, 135.65, 131.97 (q, J=30.9 Hz), 130.11, 129.36, 127.27 (q, J=5.8 Hz), 125.46 (q, J=273.7 Hz), 80.74, 41.39 (d, J=3.7 Hz), 28.73. $^{19}$F NMR (376 MHz, CD$_3$OD) δ−60.54 (s, 3F). HRMS [M+Na]$^+$ Calcd for C$_{14}$H$_{16}$F$_3$NO$_4$ 342.0924; found 342.0929.

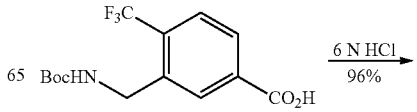

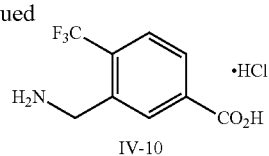

3-(Aminomethyl)-4-(trifluoromethyl)benzoic acid hydrochloride (IV-10)

To 3-(((tert-butoxycarbonyl)amino)methyl)-4-(trifluoromethyl)benzoic acid (IV-27, 48 mg, 0.15 mmol) was added 6 N HCl (8 mL). The solution was allowed to stir at room temp for 6 h. The reaction mixture was then washed with $CH_2Cl_2$ (2×4 mL), followed by evaporation of the solvent to yield the desired product as a white solid (37 mg, 97%). $^1$H NMR (500 MHz, $CD_3OD$) δ 8.42 (s, 1H), 8.22 (d, J=8.2 Hz, 1H), 7.94 (d, J=8.2 Hz, 1H), 4.41 (s, 2H). $^{13}$C NMR (126 MHz, $CD_3OD$) δ 167.53, 136.43, 133.63–132.74 (m), 132.99, 128.09 (q, J=5.5 Hz), 125.05 (q, J=273.6 Hz), 40.39. $^{19}$F NMR (376 MHz, $CD_3OD$) δ −59.46 (s, 3F).

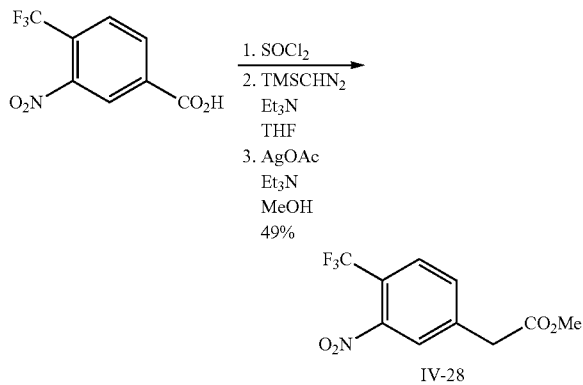

Methyl 2-(3-nitro-4-(trifluoromethyl)phenyl)acetate (IV-28)

A solution of 3-nitro-4-(trifluoromethyl)benzoic acid IV-23 (1.4 g, 5.95 mmol) in thionyl chloride (10 mL) was heated to reflux with stirring for 6 h. The yellow solution was concentrated to give an oil, which was diluted in anhydrous THF (10 mL) and cooled to 0° C. with stirring. This solution was added dropwise to a stirred solution of triethylamine (1.91 mL, 13.7 mmol) and $TMSCHN_2$ (2 M in hexanes, 3.6 mL, 7.2 mmol) in THF at 0° C. The mixture was stirred at 0° C. for 16 h, filtered with the aid of additional ether, then concentrated to give an orange oil that was diluted in MeOH (20 mL). To this solution was added triethylamine (913 μL, 6.55 mmol) followed by silver (I) acetate (596 mg, 3.57 mmol) then heated at 50° C. for 4 h before it was concentrated. The crude residue was diluted in ethyl acetate and filtered through a Celite pad. The filtrate was washed successively with saturated sodium bicarbonate (2×30 mL), water (30 mL), saturated ammonium chloride (2×30 mL), and brine (30 mL), then dried ($Na_2SO_4$), concentrated under reduced pressure, and chromatographed (ethyl acetate/hexanes, 1:9) to yield the desired product as an orange oil (764 mg, 49%). $^1$H NMR (500 MHz, $CDCl_3$) δ 7.83 (s, 1H), 7.78 (d, J=8.1 Hz, 1H), 7.65 (d, J=7.9 Hz, 1H), 3.77 (s, 2H), 3.73 (s, 4H). $^{13}$C NMR (126 MHz, $CDCl_3$) δ 170.07 (s), 148.17 (s), 140.26 (s), 133.70 (s), 128.22 (q, J=5.2 Hz), 122.56 (q, J=34.3 Hz), 122.04 (q, J=273.2 Hz), 52.69 (s), 40.19 (s). 19F NMR (376 MHz, $CDCl_3$) δ −60.41 (3F, s). HRMS [M-F]$^+$ Calcd for $C_{10}H_8F_3NO_4$ 244.0416; found 244.0410.

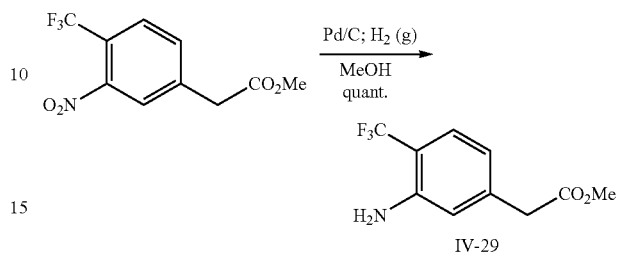

Methyl 2-(3-amino-4-(trifluoromethyl)phenyl)acetate (IV-29)

To a solution of methyl 2-(3-nitro-4-(trifluoromethyl)phenyl)acetate (IV-28, 750 mg, 2.85 mmol) in methanol (15 mL) was added Pd/C (10 wt %, 75 mg). The reaction mixture was placed under $H_2$ atmosphere, vigorously stirred overnight, then filtered through a Celite pad with the aid of additional methanol. The filtrate was concentrated to dryness under reduced pressure to yield the desired product as a clear oil without further purification. $^1$H NMR (500 MHz, $CDCl_3$) δ 7.34 (m, 1H), 6.65 (m, 2H), 4.23 (s, 2H), 3.68 (s, 3H), 3.53 (s, 2H). $^{13}$C NMR (126 MHz, $CDCl_3$) δ 171.54 (s), 144.81 (s), 139.02 (s), 126.81 (q, J=5.1 Hz), 125.00 (q, J=271.9 Hz), 118.38 (s), 117.73 (s), 112.50 (q, J=30.1 Hz), 52.14 (s), 40.80 (s). $^{19}$F NMR (376 MHz, $CDCl_3$) δ −63.00 (s, 3F). HRMS [M-F]$^+$ Calcd for $C_{10}H_{10}F_3NO_2$ 214.0680; found 214.0678.

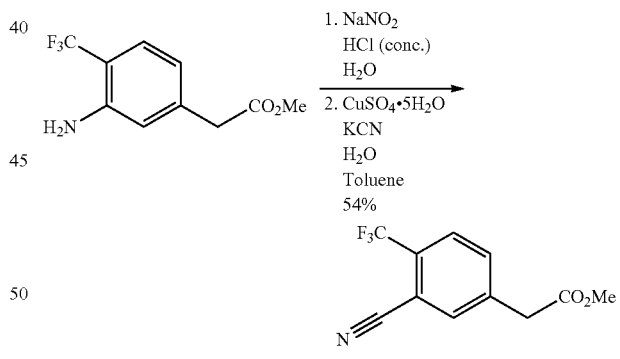

Methyl 2-(3-cyano-4-(trifluoromethyl)phenyl)acetate (IV-30)

Compound IV-30 was synthesized using a similar procedure to that of IV-35 (54%). $^1$H NMR (500 MHz, $CDCl_3$) δ 7.78 (s, 1H), 7.76 (d, J=8.2 Hz, 1H), 7.65 (d, J=8.2 Hz, 1H), 3.74 (m, 5H). $^{13}$C NMR (126 MHz, $CDCl_3$) δ 170.20 (s), 139.12 (s), 135.69 (s), 134.04 (s), 131.78 (q, J=33.4 Hz), 127.10 (q, J=4.5 Hz), 122.45 (q, J=273.6 Hz), 115.38 (s), 110.58 (s), 52.75 (s), 40.28 (s). $^{19}$F NMR (376 MHz, $CDCl_3$) δ −62.30 (s, 3F). HRMS [M+H]$^+$ Calcd for $C_{11}H_8F_3NO_2$ 244.0580; found 244.0588.

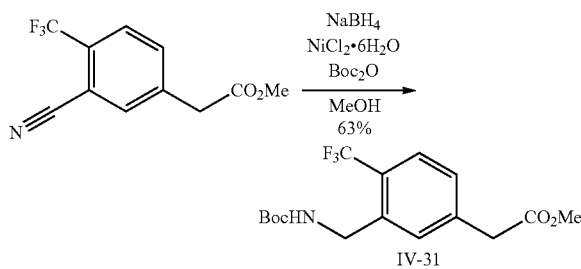

Methyl 2-(3-(((tert-butoxycarbonyl)amino)methyl)-4-(trifluoromethyl)phenyl)acetate (IV-31)

Compound IV-31 was synthesized using a similar procedure to that of IV-26 (63%). $^1$H NMR (500 MHz, CDCl$_3$) δ 7.60 (d, J=8.0 Hz, 1H), 7.47 (s, 1H), 7.30 (d, J=8.5 Hz, 1H), 5.02 (t, J=6.4 Hz, 1H), 4.49 (d, J=6.3 Hz, 2H), 3.70 (s, 3H), 3.68 (s, 2H), 1.47 (s, 9H). $^{13}$C NMR (126 MHz, CDCl$_3$) δ 171.25 (s), 155.91 (s), 138.48 (s), 137.92 (s), 130.88 (s), 128.35 (s), 126.88 (q, J=30.8 Hz), 126.38 (q, J=5.5 Hz), 124.44 (q, J=273.6 Hz), 79.87 (s), 52.31 (s), 40.88 (s), 28.44 (s). $^{19}$F NMR (376 MHz, CDCl$_3$) δ−60.05 (s, 3F). HRMS [M+Na]$^+$ Calcd for C$_{16}$H$_{20}$F$_3$NO$_4$ 370.1237; found 370.1241.

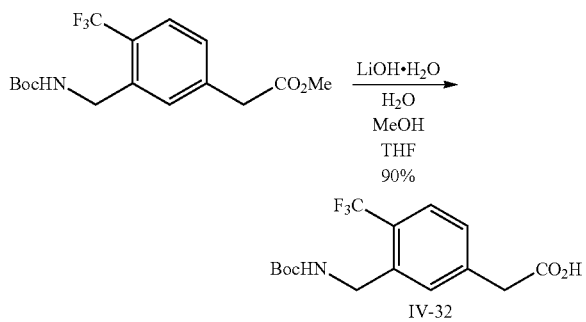

2-(3-(((tert-Butoxycarbonyl)amino)methyl)-4-(trifluoromethyl)phenyl)acetic acid (IV-32)

Compound IV-32 was synthesized using a similar procedure to that of IV-27 (90%). $^1$H NMR (500 MHz, CD$_3$OD) δ 7.62 (d, J=8.0 Hz, 1H), 7.47 (s, 1H), 7.34 (d, J=8.1 Hz, 1H), 4.44 (s, 2H), 3.69 (s, 2H), 1.47 (s, 9H). $^{13}$C NMR (126 MHz, CD$_3$OD) δ 174.49, 158.44, 140.85, 139.36, 130.45, 129.28, 127.11 (q, J=30.6 Hz), 127.07 (q, J=5.8 Hz), 127.06 (q, J=272.9 Hz), 80.51, 41.70, 41.53, 28.76. $^{19}$F NMR (376 MHz, CD$_3$OD) δ−59.75 (s, 3F). HRMS [M+Na]$^+$ Calcd for C$_{15}$H$_{18}$F$_3$NO$_4$ 356.1080; found 356.1081.

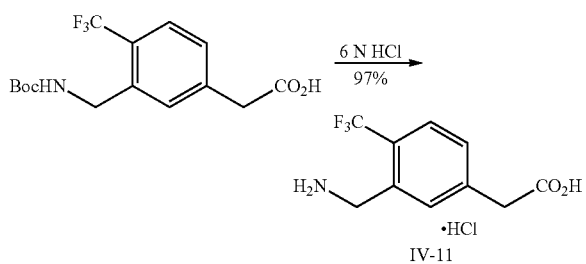

2-(3-(Aminomethyl)-4-(trifluoromethyl)phenyl)acetic Acid Hydrochloride (IV-11)

Compound IV-11 was synthesized using a similar procedure to that of IV-27 (97%). $^1$H NMR (500 MHz, CD$_3$OD) δ 7.78 (d, J=8.1 Hz, 1H), 7.66 (s, 1H), 7.56 (d, J=8.1 Hz, 1H), 4.32 (s, 2H), 3.80 (s, 2H). $^{13}$C NMR (126 MHz, CD$_3$OD) δ 174.20, 141.94, 133.52, 132.50, 131.91, 128.42 (q, J=30.6 Hz), 127.78 (q, J=5.6 Hz), 125.60 (q, J=272.7 Hz), 41.17, 40.59. $^{19}$F NMR (376 MHz, CD$_3$OD) δ−58.77 (s, 3F). HRMS [M+H]$^+$ Calcd for C$_{10}$H$_{10}$F$_3$NO$_2$ 234.0736; found 234.0720.

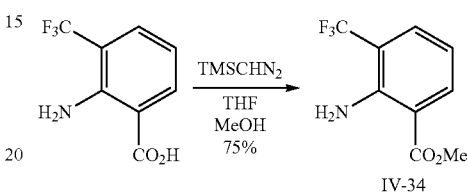

Methyl 2-amino-3-(trifluoromethyl)benzoate (IV-34)

To a stirred solution of 2-amino-3-(trifluoromethyl)benzoic acid (IV-33, 5.0 g, 24.4 mmol) in anhydrous THF (85 mL) and methanol (20 mL) was added dropwise TMSCHN$_2$ (2 M in hexanes, 17.1 mL, 34.1 mmol). Upon cessation of nitrogen gas evolution, the reaction is stirred for an additional 30 min at room temp, then quenched with acetic acid (1 mL) and concentrated. The crude product was purified by chromatography (ethyl acetate/hexanes, 1:9) to afford the desired product as a clear oil (4.0 g, 75%). $^1$H NMR (500 MHz, CDCl$_3$) δ 8.05 (d, J=7.9 Hz, 1H), 7.58 (d, J=7.6 Hz, 1H), 6.65 (t, J=7.8 Hz, 1H), 6.47 (br s, 2H), 3.88 (s, 3H). $^{13}$C NMR (126 MHz, CDCl$_3$) δ 168.14 (s), 148.22 (s), 135.59 (s), 131.95 (q, J=5.3 Hz), 124.75 (q, J=272.4 Hz), 114.77 (s), 114.70 (q, J=29.8 Hz), 112.23 (s), 51.99 (s). $^{19}$F NMR (376 MHz, CDCl$_3$) δ−63.89 (s, 3F). HRMS [M-F]$^+$ Calcd for C$_9$HsF$_3$NO$_2$ 200.0518; found 200.0526.

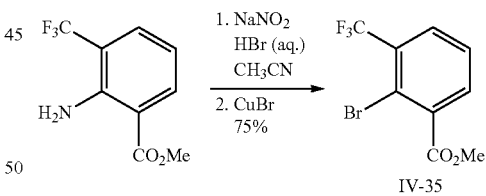

Methyl 2-bromo-3-(trifluoromethyl)benzoate (IV-35)

To a stirred solution of methyl 2-amino-3-(trifluoromethyl)benzoate (IV-34, 3.6 g, 16.4 mmol) in CH$_3$CN (22 mL) was added HBr (48% (aq), 20.3 mL) dropwise at 0° C. over 10 min. Then, NaNO$_2$ (1.25 g, 18.1 mmol) in water (5 mL) was added dropwise over 1 h at 0° C. with vigorous stirring. After addition, the solution was stirred for 5 min at 0° C. followed by the addition of CuBr (2.71 g, 18.9 mmol) in portions over 30 min. The mixture was heated at 70° C. for 1 h then cooled again to 0° C. before being diluted with water (40 mL) and extraction with EtOAc (3×50 mL). The combined organic layers were washed with water (50 mL)

and brine (50 mL), dried (Na₂SO₄), concentrated to dryness under reduced pressure, and chromatographed (ethyl acetate/hexanes, 1:9) to afford a clear oil (3.47 g, 75%). ¹H NMR (500 MHz, CDCl₃) δ 7.74 (dd, J=8.0, 1.7 Hz, 1H), 7.69 (dd, J=7.7, 1.7 Hz, 1H), 7.43 (t, J=7.8 Hz, 1H), 3.92 (s, 3H). ¹³C NMR (126 MHz, CDCl₃) δ 166.77, 136.82, 133.04, 131.53 (q, J=31.0 Hz), 129.78 (q, J=5.6 Hz), 127.38, 122.77 (q, J=273.8 Hz), 118.56, 52.93. ¹⁹F NMR (376 MHz, CDCl₃) δ−62.78 (s, 3F). HRMS [M+H]⁺ Calcd for C₉H₆BrF₃O₂ 282.9576; found 282.9575.

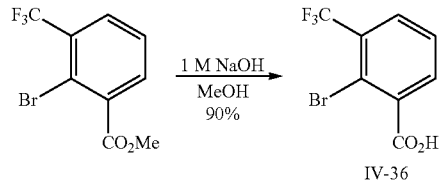

2-Bromo-3-(trifluoromethyl)benzoic acid (IV-36)

To a solution of methyl 2-bromo-3-(trifluoromethyl)benzoate (IV-35, 3.0 g, 10.6 mmol) in methanol (50 mL) was added 1 M NaOH (53 mL) and allowed to stir at room temp for 5 h. After removal of bulk solvent, the reaction mixture was partitioned between ether (50 mL) and water (50 mL). The aqueous phase was extracted with ether (3×30 mL), and the combined organic layers were discarded. The aqueous phase was adjusted to pH 1 with 2 N HCl and extracted with EtOAc (3×30 mL). The combined organics were washed with brine (30 mL), dried (Na₂SO₄), and concentrated to dryness under reduced pressure to yield the desired product as white crystals (2.57 g, 90%). ¹H NMR (500 MHz, CD₃OD) δ 7.88 (d, J=7.7 Hz, 1H), 7.83 (d, J=7.5 Hz, 1H), 7.61 (t, J=7.7 Hz, 1H). ¹³C NMR (126 MHz, CD₃OD) δ 169.52, 139.80, 134.02, 132.26 (q, J=30.7 Hz), 130.50 (q, J=5.8 Hz), 129.04, 124.38 (q, J=272.8 Hz), 118.42. ¹⁹F NMR (376 MHz, CD₃OD) δ−61.98 (s, 3F). HRMS [M−H]⁻ Calcd for C₈H₄BrF₃O₂ 266.9274; found 266.9281.

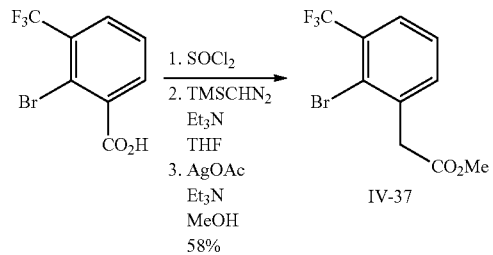 [SMILES: O=C(O)c1cccc(C(F)(F)F)c1Br ; COC(=O)Cc1cccc(C(F)(F)F)c1Br ; "IV-37"]

Methyl 2-(2-bromo-3-(trifluoromethyl)phenyl)acetate (IV-37)

Compound IV-37 was synthesized using a similar procedure to that of IV-28 (58%). ¹H NMR (500 MHz, CDCl₃) δ 7.63 (d, J=7.8 Hz, 1H), 7.47 (d, J=7.5 Hz, 1H), 7.39 (t, J=7.7 Hz, 1H), 3.89 (s, 2H), 3.72 (s, 3H). ¹³C NMR (126 MHz, CDCl₃) δ 170.51, 137.18, 134.92, 131.09 (q, J=30.8 Hz), 127.43, 127.05 (q, J=5.7 Hz), 123.09 (q, J=273.5 Hz), 122.87 (q, J=3.1 Hz), 52.46, 42.15. ¹⁹F NMR (376 MHz, CDCl₃) δ−62.87 (s, 3F). HRMS [M+H]⁺ Calcd for C₁₀H₈BrF₃O₂ 296.9733; found 296.9730.

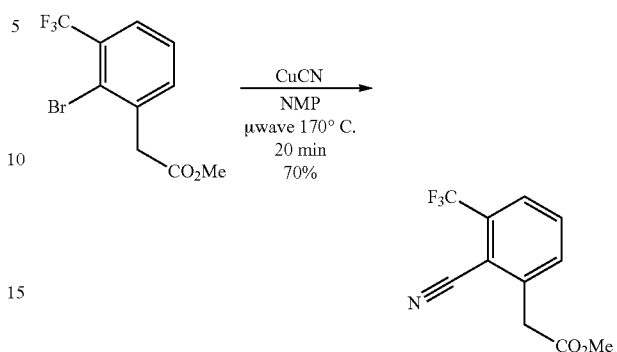

Methyl 2-(2-cyano-3-(trifluoromethyl)phenyl)acetate (IV-38)

A mixture of methyl 2-(2-bromo-3-(trifluoromethyl)phenyl)acetate (IV-37, 1.9 g, 6.4 mmol) and CuCN (1.14 g, 12.8 mmol) in N-methyl-2-pyrrolidone (5 mL) was irradiated in a microwave apparatus at 175° C. for 20 min. After cooling to room temp, the reaction mixture was diluted with EtOAc (10 mL) then filtered through a Celite pad. The filtrate was further diluted with EtOAc (40 mL), washed with water (3×20 mL) and brine (20 mL), dried (Na₂SO₄), concentrated to dryness under reduced pressure, and chromatographed (ethyl acetate/hexanes, 1:9) to afford a yellow oil (2.87 g, 70%). ¹H NMR (500 MHz, CDCl₃) δ 7.73 (dd, J=7.9, 1.7 Hz, 1H), 7.70 (t, J=7.7 Hz, 1H), 7.65 (dd, J=7.5, 1.7 Hz, 1H), 3.98 (s, 2H), 3.74 (s, 3H). ¹³C NMR (126 MHz, CDCl₃) δ 169.68, 140.48, 134.17, 133.46 (q, J=32.4 Hz), 132.80, 125.57 (q, J=4.8 Hz), 122.45 (q, J=273.9 Hz), 114.16, 111.02, 52.71, 39.46. ¹⁹F NMR (376 MHz, CDCl₃) δ−62.41 (s, 3F). HRMS (GC-EI-TOF) Calcd for C₁₁H₈F₃NO₂ [M]·⁺ 243.0507; found 243.0356.

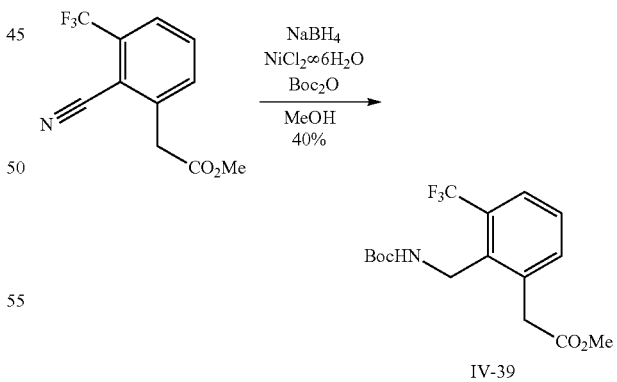

Methyl 2-(2-(((tert-butoxycarbonyl)amino)methyl)-3-(trifluoromethyl)phenyl)acetate (IV-39)

Compound IV-39 was synthesized using a similar procedure to that of IV-31 (40%). ¹H NMR (500 MHz, CDCl₃) δ 7.60 (d, J=7.8 Hz, 1H), 7.46 (d, J=7.7 Hz, 1H), 7.38 (t, J=7.8 Hz, 1H), 4.82-4.68 (m, 1H), 4.52 (d, J=5.8 Hz, 2H), 3.90 (s, 2H), 3.70 (s, 3H), 1.43 (s, 9H). $^{13}$C NMR (126 MHz, CDCl$_3$) δ 171.87, 155.40, 136.54, 135.34, 135.08, 130.16 (q, J=29.5 Hz), 128.18, 125.47 (q, J=5.9 Hz), 124.49 (q, J=273.7 Hz), 79.84, 52.45, 38.18, 37.96, 28.45. $^{19}$F NMR (376 MHz, CDCl$_3$) δ−58.72 (s, 3F). HRMS [M+Na]$^+$ Calcd for C$_{16}$H$_{20}$F$_3$NO$_4$ 370.1237; found 370.1242.

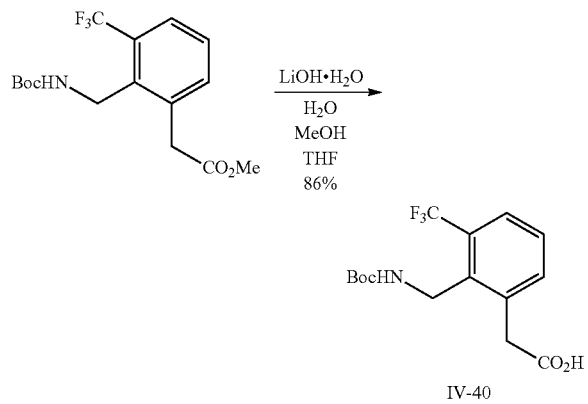

IV-40

2-(2-(((tert-Butoxycarbonyl)amino)methyl)-3-(trifluoromethyl)phenyl)acetic acid (IV-40)

Compound IV-40 was synthesized using a similar procedure to that of IV-27 (86%). $^1$H NMR (500 MHz, CD$_3$OD) δ 7.65 (d, J=7.8 Hz, 1H), 7.55 (d, J=7.6 Hz, 1H), 7.45 (t, J=7.8 Hz, 1H), 4.43 (s, 2H), 3.84 (s, 2H), 1.45 (s, 6H). $^{13}$C NMR (126 MHz, CD$_3$OD) δ 174.82, 157.62, 138.73, 136.38, 131.01 (q, J=29.6 Hz), 129.18, 126.08 (q, J=6.0 Hz), 125.84 (q, J=273.4 Hz), 80.43, 49.85, 39.29, 38.73, 28.74. $^{19}$F NMR (376 MHz, CD$_3$OD) δ−58.18 (s, 3F). HRMS [M+Na]$^+$ Calcd for C$_{15}$H$_{18}$F$_3$NO$_4$ 356.1080; found 356.1084.

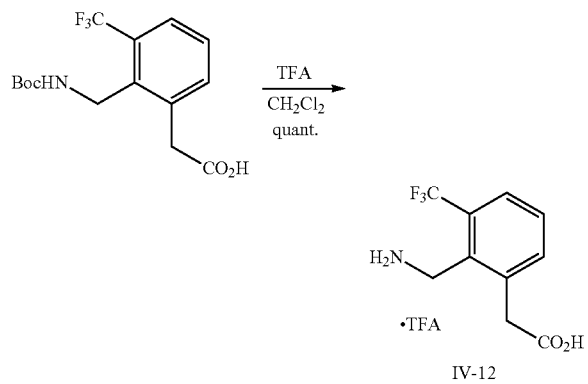

IV-12

2-(2-(Aminomethyl)-3-(trifluoromethyl)phenyl)acetic Acid Hydrochloride (IV-12)

To a stirred solution of 2-(2-(((tert-butoxycarbonyl)amino)methyl)-3-(trifluoromethyl)phenyl)acetic acid (IV-40, 180 mg, 0.54 mmol) in CH$_2$Cl$_2$ (6 mL) at 0° C. was added dropwise TFA (3 mL). The reaction was allowed to slowly warm to room temp over 3 h before removal of solvent under reduced pressure to yield the desired product as white crystals (178 mg, 100%). $^1$H NMR (500 MHz, CD$_3$OD) δ 7.80 (d, J=7.6 Hz, 1H), 7.70 (d, J=7.6 Hz, 1H), 7.62 (t, J=7.8 Hz, 1H), 4.42 (s, 2H), 3.98 (s, 2H). $^{13}$C NMR (126 MHz, CD$_3$OD) δ 175.36, 161.36 (q, J=37.7 Hz), 139.44, 137.04, 131.76 (q, J=29.4 Hz), 131.42, 131.36, 127.14 (q, J=5.8 Hz), 125.67 (q, J=273.2 Hz), 117.38 (q, J=288.5 Hz), 39.40, 37.58. $^{19}$F NMR (376 MHz, CD$_3$OD) δ−59.28 (s, 3F). HRMS [M+H]$^+$ Calcd for C$_{10}$H$_{10}$F$_3$NO$_2$ 233.0664; found 233.0668.

Example 4

Title: Apicomplexan Ornithine Aminotransferases
Abstract

Toxoplasmosis, the disease caused by the parasite *Toxoplasma gondii* (*T. gondii*), is the leading cause of death attributed to food-borne illness in the United States. It is estimated that this parasite infects between 30 and 50% of the world population. One potential therapeutic target in the fight against this parasite is ornithine aminotransferase (TgOAT), a pyridoxal 5'-phosphate (PLP)-dependent enzyme that plays a crucial role in preventing toxic accumulation of ornithine in the cell. A selective inhibition of OAT in *T. gondii* over human OAT is highly desired in either eliminating the growth of the parasites or preventing the shedding of infectious oocysts into the environment. We have characterized a number of features of TgOAT: the gene, protein, abundance in different life cycle stages, and enzyme activity. A screening of our library of 23 GABA analogues resulted in several selective inactivators of TgOAT. Crystal structures of the native and inactivated enzymes were obtained. Two different inactivation mechanisms of two different inactivators were identified: one by gabaculine, which inactivated the enzyme by forming an aromatic ring inside the active site, which created a large energy barrier to reversal and put the product in a deep thermodynamic well, and the other by (S)-4-amino-5-fluoropentanoic acid, which inactivated the enzyme by forming a covalent adduct to the enzyme. These newly identified TgOAT inactivators and insights of the enzyme binding pocket from crystal structures lay a foundation of further studies of selective inactivation of TgOAT and drug development.

Introduction

The Apicomplexan parasites *Toxoplasma gondii* and *Plasmodium falciparum* are major causes of morbidity and mortality worldwide.[1] Toxoplasmosis, the disease caused by *T. gondii*, is the leading cause of death attributed to food-borne illness in the United States.[1] Globally, this parasite infects between 30 and 50% of the population.[2] This means that approximately two billion people have this parasite living within their brains, with largely unknown consequences. There are three life cycle stages of *T. gondii*: tachyzoites are the active form that destroy tissues during acute infections; bradyzoites are the dormant form that encyst and remain a source of recrudescent infection; and sporozoites, formed in the cat intestine, are widely disseminated in nature. Infection with *T. gondii* typically occurs via inadvertent ingestion of infectious oocysts in food or water contaminated by cat excrement.[3] Indeed, it has been estimated that the number of infectious oocysts per square foot of soil in the U.S. ranges from 9 to 434.[4] The ingestion of a single oocyst is capable of inducing infection and they persist in warm, moist soil or water for up to a year.5-[7] Comprising a public health threat, toxoplasmosis results in a wide range of serious health problems, including blindness and neurological disease in congenital infection and severe meningoencephalitis in immunocompromised persons. The parasite *P. falciparum* also causes significant human suffering. In 2013, there were 584,000 deaths, with 78% occurring in children younger than 5 years of age.[12] Like the cat vector for *Toxoplasma*, the malaria vector, the *Anopheles* mosquito, transmits a disease that remains a substantial threat to human health. Current therapeutics for *T. gondii* and *P. falciparum* have limitations, including toxicity, hypersensitivity reactions, an inability to eliminate the latent, encysted bradyzoite life stage of *T. gondii*, and drug resistance of malaria.[13-17] For these reasons, new therapeutic approaches are needed.

To address this important issue, a variety of molecular targets have been identified on the basis of several characteristics, including computed druggability, phylogenetic data, assayability, and potential of structure determination.[18,19] One such target was chosen for its role in the metabolism of arginine and ornithine, as well as in amino acid biosynthesis; this is the mitochondrial matrix enzyme ornithine aminotransferase (OAT). OAT is a pyridoxal 5'-phosphate (PLP)-dependent enzyme that catalyzes the conversion of L-ornithine to L-glutamate-5-semialdehyde, which spontaneously cyclizes to form $\Delta^1$-pyrroline-5-carboxylate (FIG. 1).[20] In this first half of the catalytic cycle, the cofactor PLP is converted to pyridoxamine 5'-phosphate (PMP). In the second half of its catalytic cycle, OAT also converts α-ketoglutarate from the Krebs cycle to L-glutamate and returns PMP to PLP. One main role of OAT is to prevent toxic accumulation of ornithine in the cell. In human, a deficiency of OAT is known to cause gyrate atrophy of the choroid and retina, but high levels of the enzyme impair the detoxification of ammonia by ornithine carbamoyltransferase, through the urea cycle.[20] A selective inhibition of TgOAT and PfOAT over human OAT would potentially lead to a toxic accumulation of ornithine only in the parasites.

While human OAT has been well studied and characterized, and has demonstrated to be a high therapeutic target,[20-22] our knowledge of *T. gondii* OAT and *P. falciparum* OAT is severely limited, with the current understanding being based on parallels to other species. While the kinetic and crystallographic analysis of PfOAT was characterized previously,[23,24] TgOAT has not been characterized, structurally or functionally, or studied for its potential as a molecular target in this parasite. No selective inhibitors of TgOAT had been identified to target any of the parasite life cycle stages. It has been known that expression of TgOAT was ~256 times higher in sporozoites than in tachyzoites and bradyzoites; therefore, even if this molecular target was not critical for tachyzoites or bradyzoites, targeting the formation of the environmentally-resistant oocyst life cycle stage could have a significant impact on disrupting the chain of transmission and, thereby, decrease the consequent morbidity and mortality. We have identified for the first time several selective irreversible inhibitors, a.k.a. inactivators, of TgOAT that could be used for studying selective inactivation of TgOAT for further drug development. We also characterized a number of features of TgOAT: the gene, protein, abundance in different life cycle stages, and enzyme activity. We obtained the crystal structure of the native TgOAT and the crystal structures of two different types of inactivated TgOAT: one by gabaculine, which inactivated the enzyme by forming an aromatic ring inside the active site, which created a large energy barrier to reversal and put the product in a deep thermodynamic well, and the other by (S)-4-amino-5-fluoropentanoic acid, 18 (FIG. 3), which inactivated the enzyme by forming a covalent adduct to the enzyme.

Materials and Methods

Target Selection.

Ornithine aminotransferase was initially deposited into and selected from the Tropical Disease Resource (TDR) Targets Database, by Agilero and colleagues in 2008.[18,19] It was selected by the Center for Structural Genomics of Infectious Disease at Northwestern University for further study on the basis of its documented importance to several key metabolic pathways, including the molecular processing of ornithine in the urea cycle and the role of ornithine in the polyamine pathway, and the predicted feasibility of solution of its secondary structure.

Multi-Sequence Alignment of Ornithine Aminotransferase. An amino acid sequence alignment performed with Clustal Omega was used to determine degree of conservation of OAT across species.[25] TgOAT was compared with homologues from close evolutionary relatives like *Hammondia hammondi* and *Neospora caninum*, another Apicomplexan parasite, *P. falciparum*, and the vertebrates, *Felis catus*, and *Homo sapiens*. Accession numbers include *T. gondii* (XP_002365604.1), *H. hammondi* (XP_008882303.1), *N. caninum* (XP_003883978.1), *P. falciparum* (CAG25330.1), *F. catus* (XP_003994548.1), and *H. sapiens* (AAA59957.1). Structures of *H. sapiens* (PDB Accession Number—1OAT) and *P. falciparum* OAT (PDB Accession Number—3NTJ) have been reported previously.[26,27] More detailed sequence alignments were performed in Consurf with 300 sequence identified with a sequence identity between 25-90%.

Single Nucleotide Polymorphism (SNP) Analysis and Phylogeny Construction.

Nucleic acid sequences for *Toxoplasma gondii* ornithine aminotransferase were extracted from the toxodb website (http://toxodb.org/) for all available isolates. Sequences were formatted and exported as a FASTA file for analysis. Using PHYLIP (PHYLogeny Inference Package, v3.696) programs included in the Seaview phylogeny interface (http://doua.prabi.fr/software/seaview), 1000 pseudoreplicate data sets were created and an unrooted bootstrap consensus tree was constructed by parsimony analysis.

Cloning, Expression and Purification.

Gene (GI: 237832613) of a putative OAT from *T. gondii* ME49 (OAT; truncated construct (residues 17-441); TgOAT (17-441)) was PCR-amplified and cloned into the IPTG (isopropyl β-D-1-thiogalactopyranoside)-inducible pMCSG28 vector by the ligation-independent-cloning.[28] The pMCSG28 vector possesses the C-terminal 6×His affinity tag and Tobacco Etch Virus (TEV) protease cleavage site. *Escherichia coli* BL21(DE3)/pMagic cells harboring the TgOAT(17-441)-pMCSG28 plasmid were grown in the Terrific Broth (TB) medium to OD600=0.6 at 37° C. followed by 1 mM IPTG induction at 25° C. overnight. Incubated cells were collected by centrifugation (6,000 rpm, 4° C., 10 min) and lysed by sonication in 10 mM Tris-HCl pH 8.3 buffer containing 500 mM NaCl and 5 mM β-mercaptoethanol (BME) (buffer A) on ice. Soluble fraction and cell debris were separated by centrifugation at 19,000 rpm, 4° C. for 40 min. Supernatant was applied onto a 5-ml Ni-NTA column (GE Healthcare, Piscataway, N.J.) and impurities were washed out using buffer A plus 25 mM imidazole. TgOAT (17-441) was eluted with 500 mM imidazole in buffer A and further purified by size exclusion chromatography on a HiLoad™ 26/60 Superdex™ 200 column (GE Healthcare, Piscataway, N.J.). All purification steps were carried out on the AKTAxpress™ (GE Healthcare Life Sciences, Piscataway, N.J.) high-throughput purification system at 4° C. Final purity of the protein was assayed by SDS-PAGE.

TgOAT Antibody Production.

Mice were injected with 50 μg of recombinant TgOAT, subcutaneously in the rump. The protein was formulated with an NISV (non-ionic surfactant vesicle) preparation to act as an adjuvant. The vesicles were made by melting mono-palmitoyl glycerol, cholesterol and dicetyl-phosphate (All from Sigma, UK) in a molar ratio of 5:4:1. Vesicles formed following the addition of warmed PBS pH 7.4 and vigorously vortexed for 2 minutes. Vesicle preparations were lyophilized and subsequently rehydrated with the appropriate protein dilutions. Vaccine preparations were stored at −20° C. until use and heated to 37° C. just prior to injection. Mice were given 2 injections of the vaccine, 2 weeks apart. 10 days after the final injection, the mice were sacrificed by $CO_2$ inhalation the blood immediately harvested by cardiac puncture. Blood samples were then centrifuged at 13,000 rpm for 10 minutes at 4° C. Serum was then transferred to a fresh tube and stored at −20° C. prior to shipping.

Enzyme Activity Assays.

L-Ornithine, PLP, NADH, and all other reagents were purchased from Sigma-Aldrich. Human recombinant pyrroline 5-carboxylate reductase 1 (PYCR1) was purchased from CD Biosciences. Ultraviolet (UV) absorption was measured using a Synergy H1 hybrid multimode microplate reader (BioTek, USA) with transparent 96-well plates (Greiner Bio-One, USA).

Assay at Various Concentrations of TgOAT.

Microplate wells were loaded with 90 μL of an assay mixture containing 100 mM potassium pyrophosphate at pH 8.0, 11.1 mM α-ketoglutarate, 1.11 mM NADH, 0.028 mM PLP, 11.1 mM L-ornithine, and 2.5 ng of PYCR1. After incubating the mixture at 37° C. for 10 min, 10 μL of various concentrations of TgOAT in 100 mM potassium pyrophosphate at pH 8.0 were added. The plate was shaken at 37° C. for 1 min, and the absorbance was measured at 340 nm every 10 s for 90 min. All assays were performed in duplicate.

Determination the $K_m$ of Ornithine Against TgOAT.

Microplate wells were loaded with 90 μL of an assay mixture containing 100 mM potassium pyrophosphate at pH 8.0, 11.1 mM α-ketoglutarate, 1.11 mM NADH, 0.028 mM PLP, 2.5 ng of PYCR1, and various concentrations of L-ornithine. After incubating the mixture at 37° C. for 10 min, 10 μL of TgOAT (1.0 mg/ml in 100 mM potassium pyrophosphate at pH 8.0) were added. The plate was shaken at 37° C. for 1 min, and the absorbance was measured at 340 nm every 10 s for 90 min. All assays were performed in duplicate.

Measurement of Kinetic Constants of an Inhibitor or Inactivator of TgOAT.

Microplate wells were loaded with 90 μL of an assay mixture containing 100 mM potassium pyrophosphate at pH 8.0, 11.1 mM α-ketoglutarate, 1.11 mM NADH, 0.028 mM PLP, 11.1 mM L-ornithine, 2.5 ng of PYCR1, and various concentrations of a compound. After incubating the mixture at 37° C. for 10 min, 10 μL of TgOAT (1.0 mg/ml in 100 mM potassium pyrophosphate at pH 8.0) were added. The plate was shaken at 37° C. for 1 min, and the absorbance was measured at 340 nm every 10 s for 90 min. All assays were performed in duplicate.

Crystallization, X-Ray Data Collection and Structure Determination.

The TgOAT protein with concentration of 7 mg/mL was crystallized in absence and presence of gabaculine and TgOAT-specific inactivators (compounds 1, 2, 5, 11 and 18, FIG. 3) by the sitting-drop vapor-diffusion technique at 295° K. The crystals of native TgOAT (PLP not bound to lysine 286) were grown in the conditions containing 200 mM ammonium acetate, 100 mM Bis-Tris pH 6.5 and 25% (w/v) PEG 3350. The structure of TgOAT with PLP bound to lysine 286 was obtained from co-crystallization of TgOAT with 5 mM compound 11 and 2 mM PLP followed by overnight incubation period at 4° C.; these crystals were grown in the conditions containing 0.2 M ammonium sulfate, 0.1 M Bis-Tris pH 5.5 and 25% (w/v) PEG3350. The crystals of TgOAT in complex with gabaculine were obtained by co-crystallization with 5 mM gabaculine and 2 mM pyrodoxil-5'-phosphate (PLP). The good diffraction quality crystals with gabaculine were grown in the conditions containing 0.2 M ammonium sulfate, 0.1 M Bis-Tris pH 5.5 and 25% (w/v) PEG3350. The crystals of TgOAT in complex with compound 18 in intermediate state and final inactivated state were obtained by co-crystallization with 5 mM compound 18 and 2 mM PLP followed by incubation period at 4° C. for 4 hours and overnight, respectively. The crystals of TgOAT in complex with compound 18 determined in intermediate and final states in the structure were grown in similar conditions containing 0.2 M ammonium sulfate, 0.1 M Bis-Tris pH 6.5 and 25% (w/v) PEG3350.

Prior to data collection, all crystals were soaked in well solution for cryoprotection and then flash frozen in liquid nitrogen. Monochromatic X-ray diffraction oscillation data from these crystals were collected at the Life Sciences Collaborative Access Team (LS-CAT) beamlines 21-ID-F (at 100° K.; λ=0.97872 Å), 21-ID-G (at 100° K.; λ=0.97856 Å), 21-ID-D (at 100° K.; λ (Å)—fully tunable) at Argonne National Laboratory (ANL), Advanced Photon Source (APS). Data were processed with HKL-3000.[29] The structures were determined by molecular replacement method using Phaser[30] from the CCP4 suite[31]. The crystal structure of the related *P. falciparum* OAT (Protein Data Bank (PDB) code 3lg0;[23] was used as a search model for native TgOAT structure that were later used to solve the structures of native TgOAT (with PLP in a bound state and an unbound state to lysine 286), and gabaculine-inactivated and 18-inactivated TgOAT. The initial structure solution for all determined structures was rebuilt using ARP/wARP.[32] Water molecules, manual structure inspection and alteration of the rebuilt structural models were done in Coot[33,34] and REFMAC v.5.8[35], respectively. The Translation-Libration-Screw (TLS) refinement (TLS groups were identified on TLSMD server http://skuld.bmsc.washington.edu/~tlsmd/;[36,37] was introduced at the final stages of refinement. Final model of structures was validated with the PDB validation server (ADIT validation server; http://deposit.pdb.org/validate/) and MolProbity;[38,39] http://molprobity.biochem.duke.edu/).

The structures were deposited to PDB under the accession code 4nog (native TgOAT with PLP not bound to lysine 286), 4zlv (TgOAT with PLP bound to lysine 286), XXXX (gabaculine-inactivated TgOAT), and YYYY (18-inactivated TgOAT). Table 2 contains detailed crystallographic data of deposited structures. Diffraction images for TgOAT (IDP92102 target) and its liganded structures are available at the Center for Structural Genomics of Infectious Diseases (CSGID) website (http://www.csgid.org/csgid/pages/home). The structural comparison between TgOAT and its homologues was done using web servers DALI, VAST and ProFunc.[40-42] All figures presenting TgOAT structure were prepared in graphical program CCP4MG.[43]

Knockdown of TgOAT in Type I Parasites.

Peptide phosphorodiamidate morpholino oligomer (PPMO) targeted against the third splice site of mRNA coding for TgOAT was designed and purchased from Gene Tools, LLC. PPMOs are chains of nucleotide analogues complementary to, but structurally distinct from, RNA, and can prevent access of the spliceosome to specific splice sites, or prevent ribosomal binding and, thereby, protein translation.[44-46] The sequence against which the PPMO was targeted is presented as SEQ ID NO:7. PPMOs have been used for molecular target validation in previous work.[47] To test the efficacy of this targeted PPMO against *T. gondii* tachyzoites, human foreskin fibroblasts (HFF) were grown in black, flat-bottomed 96-well microplates. HFFs were infected with 2000 Type I RH parasites expressing yellow fluorescent protein (YFP). This allowed quantification of parasites in vitro post-treatment with TgOAT-targeted PPMO. A concentration gradient of the YFP parasites was also established, allowing for quantification of knockdown. The parasites were incubated with the cells for one hour, to allow sufficient time for invasion of HFFs, and were then treated with PPMO. Control triplicates with only fibroblasts and with pyrimethamine and sulfadiazine (the current standard of treatment of *T. gondii* infection) were also conducted. Several runs of this efficacy assay were completed applying different concentrations of PPMO (2.5 µM, 5 µM, 10 µM, and 20 µM). The cells and parasites were then incubated at 37° C. for 72 hours, this timing having been previously established in other work.[48] Fluorescence was measured using a Bio-Tek Synergy™ H4 Hybrid Multi-Mode Microplate Reader.

In order to determine whether there was host cell toxicity from the PPMO, a WST-1 viability assay was conducted. HFFs were grown in black, flat-bottomed 96-well microplates. A gradient of dimethyl sulfoxide (DMSO) was used to quantify the amount of cell death caused by the PPMO in vitro, as some toxicity has been reported in the literature.[44] Different concentrations of PPMO (3.5, 5, 10, and 20 µM) were used to identify the level at which toxicity occurred. Following 72 hours of incubation at 37° C., each well was treated with 10 µL WST-1,water soluble tetrazolium 1, which reacts in metabolically active, viable cells through a complex set of chemical reactions dependent upon glycolytic NADPH production to form formazan dyes, which can be detected via a colorimeter.

Effect of TgOAT Inactivators on *T. gondii* In Vitro.

HFFs were grown to confluence in black, flat-bottomed 96-well microplates. HFFs were infected with 2000 Type I RH parasites expressing yellow fluorescent protein (YFP). The parasites were incubated with the cells for one hour, to allow sufficient time for invasion of HFFs, and were then treated with the TgOAT-specific GABA analogues (compounds 1, 2, 5, 11, and 18, FIG. 3) with the highest activity in inactivating TgOAT. Control triplicates with only fibroblasts and with pyrimethamine and sulfadiazine (the current standard of treatment of *T. gondii* infection) were also conducted. The cells and parasites were then incubated at 37° C. for 72 hours. Fluorescence was measured using a Bio-Tek Synergy™ H₄ Hybrid Multi-Mode Microplate Reader.

Measuring Effect of TgOAT Inactivators *P. falciparum* In Vitro.

The Malaria SYBR Green I—Based Fluorescence (MSF) Assay is a microtiter plate drug sensitivity assay that uses the presence of malarial DNA as a measure of parasitic proliferation in the presence of antimalarial drugs or experimental compounds. As the intercalation of SYBR Green I dye and its resulting fluorescence is relative to parasite growth, a test compound that inhibits the growth of the parasite will result in a lower fluorescence. D6 (CDC/Sierra Leone), TM91C235 (WRAIR, Thailand), and W2 (CDC/Indochina III) laboratory strains of *P. falciparum* were used for each drug sensitivity assessment. The parasite strains were maintained continuously in long-term cultures as previously described in Johnson et al.[49] Pre-dosed microtiter drug plates for use in the MSF assay were produced using sterile 384-well black optical bottom tissue culture plates containing quadruplicate 12 two-fold serial dilutions of each test compound or mefloquine hydrochloride (Sigma-Aldrich Co., Catalog #M2319) suspended in dimethyl sulfoxide. The final concentration range tested was 0.5-10000 ng/mL for all assays. Predosed plates were stored at 4° C. until used, not to exceed five days. No difference was seen in drug sensitivity determination between stored or fresh drug assay plates (data not shown). A batch control plate using Chloroquine (Sigma-Aldrich Co., Catalog #C6628) at a final concentration of 2000 ng/ml was used to validate each assay run. The Tecan Freedom Evo liquid handling system (Tecan US, Inc., Durham, N.C.) was used to produce all drug assay plates. Based on modifications of previously described methods by Plouffe et al and Johnson et al, *P. falciparum* strains in late-ring or early-trophozoite stages were cultured in the predosed 384-well microtiter drug assay plates in 38 µL culture volume per well at a starting parasitemia of 0.3% and a hematocrit of 2%.[49,50] The cultures were then incubated at 37° C. within a humidified atmosphere of 5% $CO_2$, 5% $O_2$ and 90% $N_2$, for 72 hours. Lysis buffer (38 aL per well), consisting of 20 mM Tris HCl, 5 mM EDTA, 1.6% Triton X, 0.016% saponin, and SYBR green I dye at a 20x concentration (Invitrogen, Catalog #S-7567) was then added to the assay plates for a final SYBR Green concentration of 10×. The Tecan Freedom Evo liquid handling system was used to dispense malaria cell culture and lysis buffer. The plates were then incubated in the dark at room temperature for 24 hours and examined for the relative fluorescence units (RFU) per well using the Tecan Genios Plus (Tecan US, Inc., Durham, N.C.). Each drug concentration was transformed into Log[X] and plotted against the RFU values. The 50% and 90% inhibitory concentrations (IC50s and IC90s, respectively) were then generated with GraphPad Prism (GraphPad Software Inc., SanDiego, Calif.) using the non-linear regression (sigmoidal dose-response/variable slope) equation.

Results

Multi-Sequence Alignments and Phylogeny.

In the alignment of amino acid sequences of known OATs, there is a high degree of conservation among *T. gondii*'s close relatives, *H. hammondi* and *Neospora caninum*, with 96% and 89% sequence identity, respectively. There is markedly less conservation between *T. gondii* and the other organisms analyzed. Alignment of TgOAT and other organisms' OATs demonstrates approximately 49% sequence identity. There is 49% sequence identity between Tg, Pf, Fc, and Hs OAT, but the shared amino acids are not the same. Analysis of OAT genetic variability in 53 *T. gondii* isolated by parsimony reveals six distinct clusters of strains based on haplotype, consistent with major clades previously established on the basis of multilocus SNP analysis.[51] Notable distinct isolate clusters in the OAT consensus tree include haplogroup 1, haplogroup 3, haplogroup 4, haplogroup 11, and haplogroup 14. Haplogroups 2 and 12, related clonal groups common in North America, comprise a single major branch. The isolated hyper-virulent Guiana appears to have diverse individual patterns for their OAT sequences.

TgOAT Activity Assays.

Figure 7:
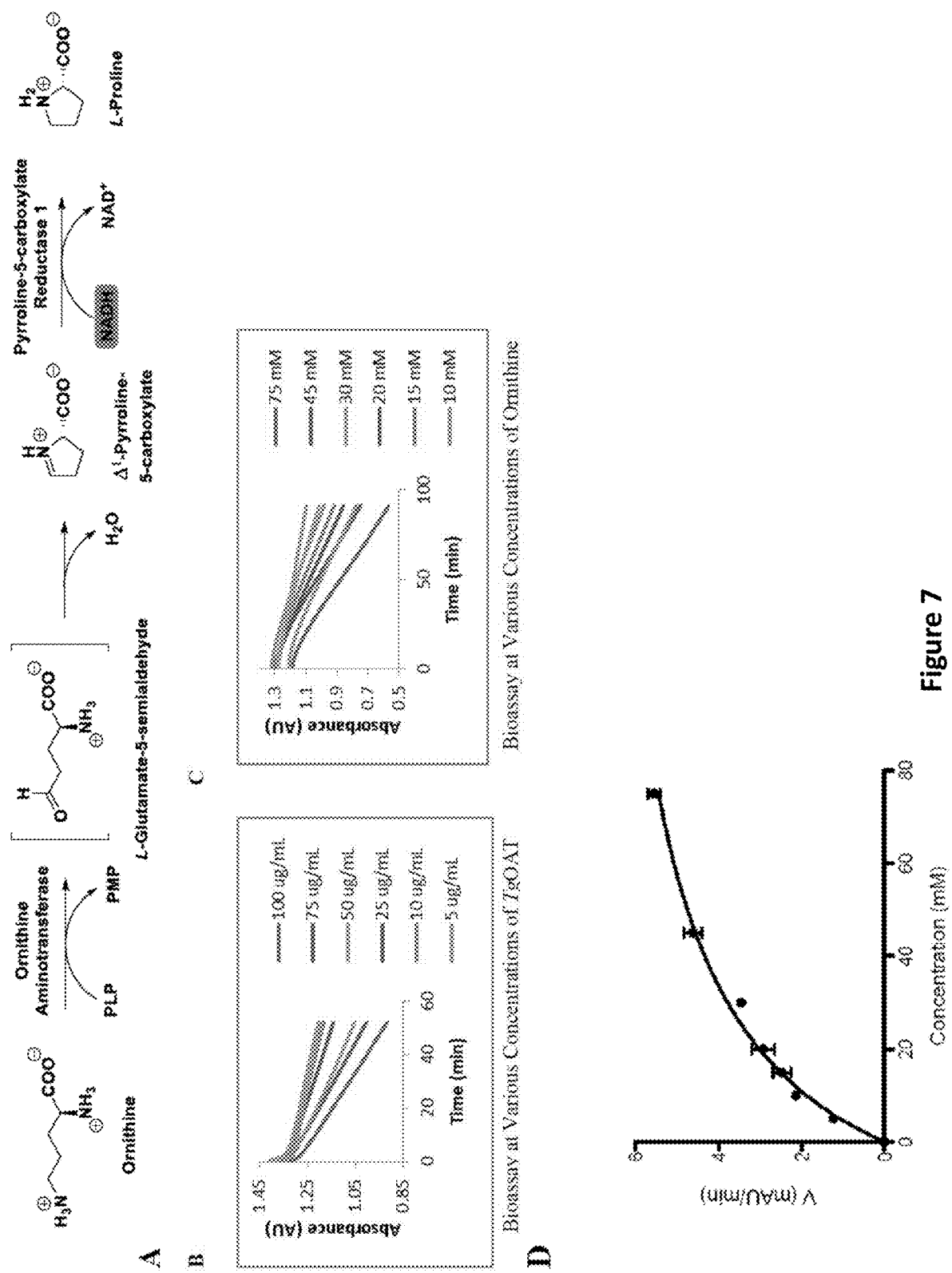
FIG. 7. (A) Pyrroline-5-carboxylate Reductase 1 (PYCR1)-Coupled Assay. (B) Bioassay at Various Concentrations of TgOAT. (C) Bioassay at Various Concentrations of Ornithine. (D) Reaction Rate V (mAU/min) of TgOAT vs Concentration of Ornithine (mM)

We have recently developed and optimized two coupled assays for the continuous measurement of OAT activity.[52] The more convenient assay employs human pyrroline-5-carboxylate reductase 1 (PYCR1) to monitor the activity of OAT in converting ornithine to L-glutamate-5-semialdehyde, which spontaneously cyclizes to form $\Delta^1$-pyrroline-5-carboxylate (P5C) (FIG. 7A). PYCR1, an NADH (nicotinamide adenine dinucleotide, reduced form)-dependent enzyme, reduces the newly formed P5C to L-proline. With excess of PYCR1 used, the activity of OAT is directly proportional to the decrease in absorbance at 340 nm, indicating the oxidation of NADH to NAD$^+$. This bioassay was chosen to test the inhibition/inactivation activity of GABA analogues against TgOAT. The assay condition used for human OAT was first carried out for TgOAT, but the difference in the reaction rates between the positive control (no inhibitor/inactivator) and negative control (no enzyme) was barely distinguishable. This result suggests that the activity of TgOAT in converting ornithine to L-glutamate-5-semialdehyde is much less than that of human OAT. An experiment to determine an applicable condition of TgOAT for the bioassay was executed at various concentrations of TgOAT (FIG. 7B). The NADH was observed to be slowly decomposed over time, which has been known to occur in phosphate buffer and by UV radiation.[53,54] When the concentration of TgOAT in the assay increased, the catalytic reaction rate increased, which led to a faster decomposition rate of NADH. At 100 μg/mL of TgOAT, the reaction rate had a clear difference from the negative control (no enzyme), so the concentration of 100 μg/mL of TgOAT was chosen for subsequent testing. To determine the $K_m$ of ornithine against TgOAT, an assay at various concentrations of ornithine was performed (FIG. 7C). The reaction rate at each concentration was estimated by linear regression analysis in the 30-60 minute range and then subtracted from the negative control (no ornithine). These reaction rates were then plotted against the concentrations of ornithine (FIG. 7D). The best fit curve was fitted to the Michaelis-Menten equation[55] to afford a $K_m$ value of 31.0±4.0 mM.

Time-Dependent and Concentration-Dependent Inhibition of TgOAT by Gaba Analogues.

Figure 3:
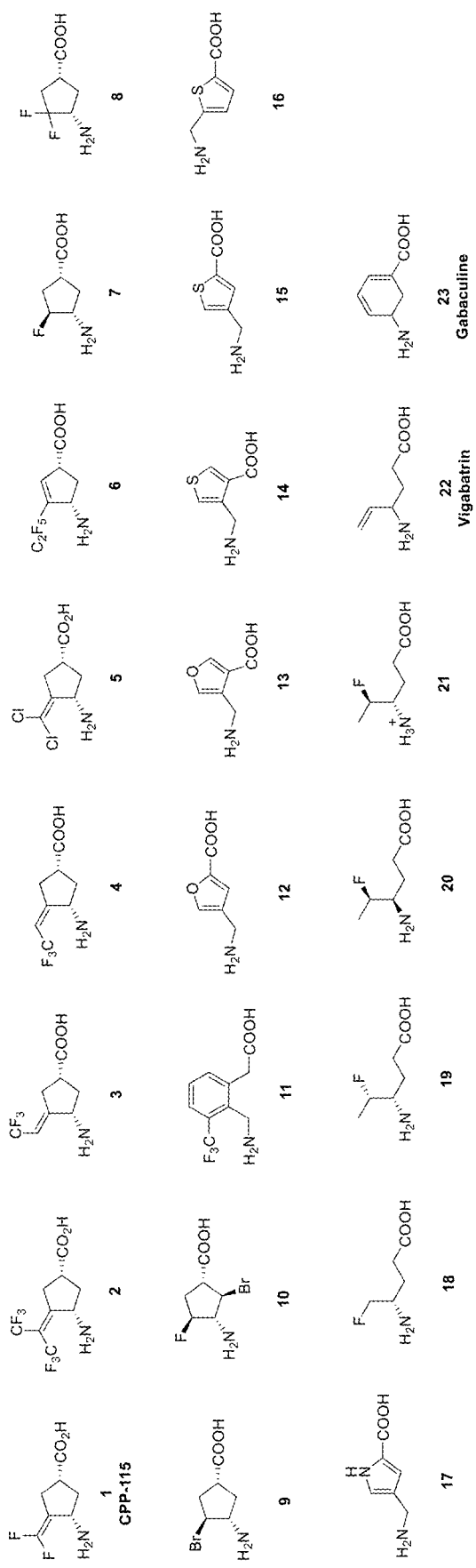
FIG. 3. GABA Analogues Screened Against TgOAT.
Figure 8:
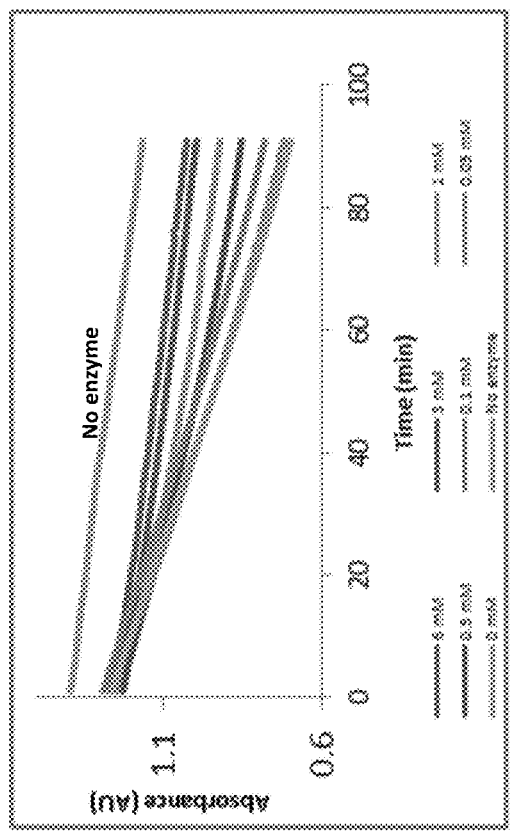
FIG. 8. Bioassays at Various Concentrations of 12 (A) and 2 (B).
Figure 8:
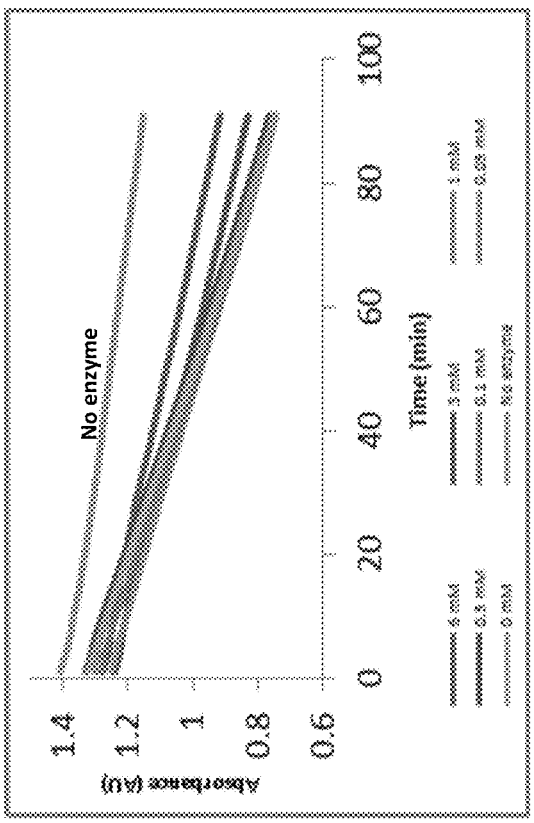

The compounds screened against TgOAT are shown in FIG. 3. For each compound, an assay at various concentrations was carried out and observed over a period of 90 minutes. When a compound acted as a reversible inhibitor of TgOAT, such as 12, the reaction rate at each concentration stayed constant during the run due to dependence on compound concentration, and not time (FIG. 8A). The percentage of enzyme activity at each concentration was estimated based on the reaction rate. IC$_{50}$ was estimated from the plot of log ([inhibitor]) versus percentage of enzyme activity, and $K_i$ value was calculated from the IC$_{50}$ value.

When a compound acted as an inactivator of TgOAT, such as 2, the reaction rate at each concentration changed during the run because it would depend on both the concentration of the compound and time (FIG. 8B). Eventually, when given enough time, all enzymes would become inactivated, and the reaction rate would have the same value as the rate of the negative control. The inhibition constant ($K_I$) and the rate constant of enzyme inactivation ($k_{inact}$) were calculated using a modification from a recent published method, where each curve was fitted into equation 1 to obtain $k_{obs}$ value at each concentration.[56] The $k_{obs}$ values were plotted against concentrations of the compound, and the best fit curve was then fitted into equation 2 to afford $K_I$ and $k_{inact}$ values.

$$\text{Absorbance} = \frac{v_i - v_s}{k_{obs}}[1 - \exp(-k_{obs}t)] + v_s t + a_0 \quad \text{Equation 1}$$

with $v_i$ is the initial velocity, $v_s$ is the steady state velocity, t is time, and $a_0$ is the initial absorbance.

$$k_{obs} = \frac{k_{inact}[I]}{K_I\left(1 + \frac{S}{K_m}\right) + [I]} \quad \text{Equation 2}$$

where [I] is the inactivator concentration and S is substrate (ornithine) concentration.

The kinetic constants for each compound are shown in Table 1.

Structure of Native TgOAT.

The crystal structure of native TgOAT from an ME49 parasite, with PLP not bound to lysine 286 was determined. The asymmetric unit in the TgOAT structure in its native form contains homodimer, a known protein functional unit.[23,24,26,57,58] Each monomer consists of 3 domains: the large PLP-binding domain and two small domains in the N- and C terminus. The N-terminal domain comprises amino-acid residues 17-86 (αI (21-31), αII (35-43), βA (53-61), βB (62-66), βC (71-74), and αIII (76-81); it adopts small β-sheet with three antiparallel β-strands surrounded by three α-helices. The large PLP-binding domain comprises amino-acid residues 87-336 (αIV (87-101), βa (109-111), αV (113-125), βb (128-133), αVI (135-155), βc (162-167), αVII (176-181), αVIII (184-189), βd (197-202), αIX (205-214), βe (219-224), αX (238-250), βf (253-257), αXI (270-275), βg (281-285), βj (294-301), αXII (302-306), and αXIII (321-336); it adopts central eight-stranded β-sheet surrounded by ten α-helices including four short helical segments. The β-strands within the central β-sheet are parallel except of the strand (3j, which runs in opposite direction to all other strands inside the β-sheet. The C-terminal domain is composed from amino-acid residues 337-441 (αXIV (339-359), βA' (366-371), βB' (374-379), αXV (385-396), βC' (397-402), βD' (407-413), and αXVI (418-439); it comprises four-stranded antiparallel β-sheet surrounded by three α-helices. Both monomers of native TgOAT dimer have a similar fold. The root mean square deviation (RMSD) calculations using program LSQKAB[59] between the 422 aligned Cu atoms show the value of 0.28 Å. The dimer interface of TgOAT structure is formed by PLP-binding and N-terminal domains with the total buried surface area of 5748 Å$^2$. There are 64 hydrogen bonds and 9 salt bridges that contribute to the dimer formation. The dimer interface mostly consists of residues located on αI, αII, βA, αIV, βa, αV, βb, αVI, αVII, and αVIII.

The TgOAT structure resembles similar structural fold to other enzymes from subgroup II of aminotransferase protein family.[60,61] The structural comparison shows that hOAT[58,62] with 51% homology and average RMSD value of 0.9 Å shares the closest secondary structural fold with TgOAT. The list of known OAT enzymes with determined structures that have similar structural fold also includes the OAT from *P. falciparum* (RMSD 1.46 Å, homology 49%),[23,24] OAT from *P. yoelii* (RMSD 1.36 Å, homology 49%)[24] and GABA-OAT from *E. coli* (RMSD 1.88 Å, homology 31%)[63]. There are also structures of uncharacterized OAT enzymes in the Protein Data Bank (www.rscb.orq)[64] with RMSD value <2 Å and homology >30% that share similar structural fold to TgOAT. Among them is OAT from *Bacillus anthracis* (PDBID 3RUY) and GABA-OAT from, *Mycobacterium smegmatis*.[65]

We made a structural comparison of TgOAT with its homologs from *H. sapiens*, *P. falciparum*, *P. yoelii* and *E.* coli.[23,26,66] The differences between TgOAT, hOAT, PJOAT and PyOAT are found mainly in the region comprises residues from C-terminal domain. The structures of PJOAT and PyOAT contain a large disordered region (171-196 residues long in TgOAT structure) in the PLP-binding domain that was omitted from the structural comparison. As mentioned earlier, the structure of GABA-OAT has a highest RMSD value and the largest displacements compare to TgOAT structure. The major differences between these structures were found in the loop between αII-βA of the TgOAT N-terminal domain; in βa, αV, βb and their connected loops, in the loop between αVI-βc, in the region comprises αVII, αVIII, βd, and αIX of the large PLP-binding domain; in the loop between βC'-βD' of the TgOAT C-terminal domain. Despite of structural dissimilarities between homologous structures, the PLP-binding pocket located on the interface of the two monomers of OAT dimer remains untouched.

Figure 4:
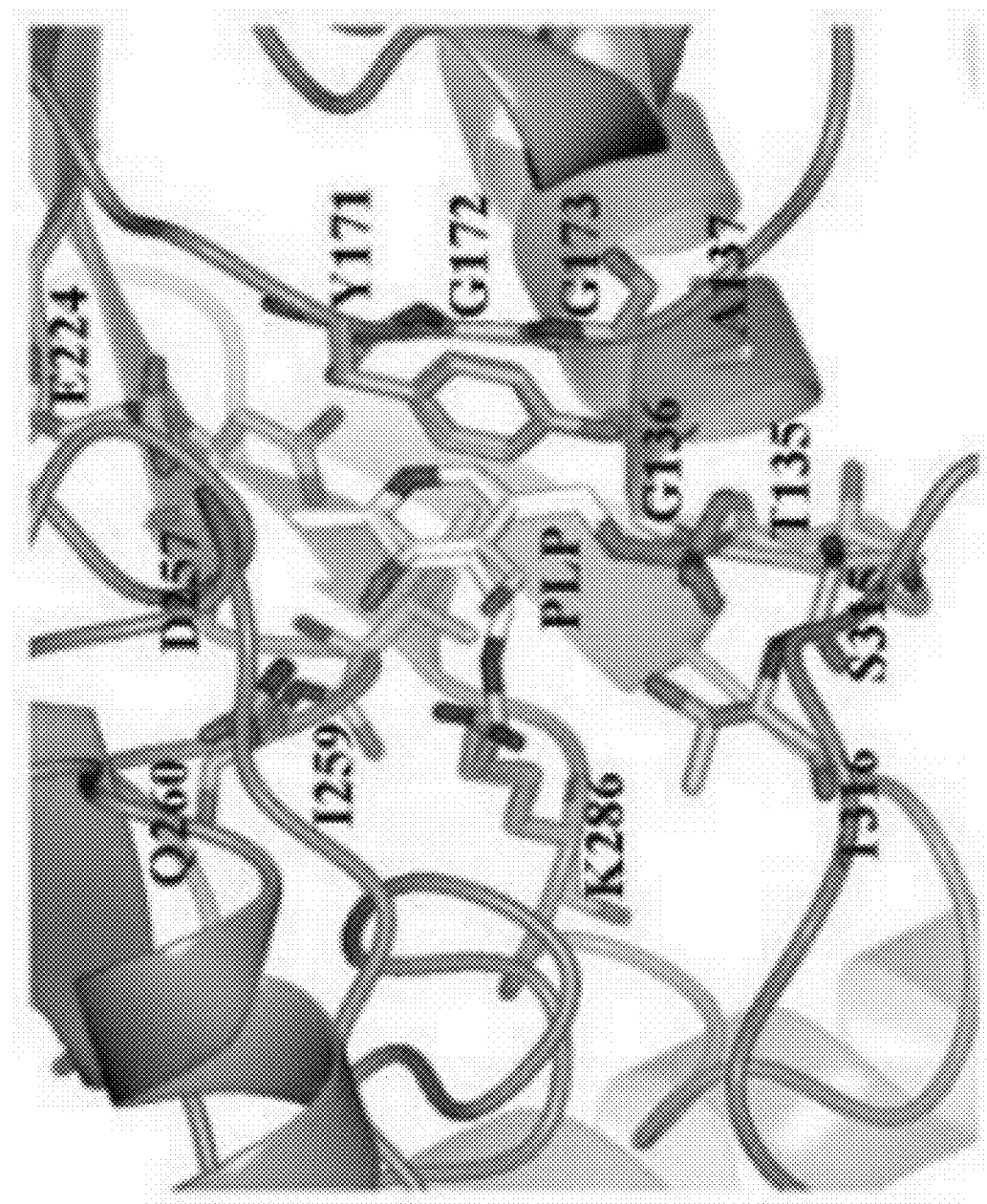
FIG. 4. Superposition of the PLP-binding site with PLP (cylinder model) in a bound state and an unbound state to lysine 286.

There are two PLP-binding sites per TgOAT dimer that position 15 Å apart from each other. Inside the cavity, the PLP molecule binds in a similar binding mode observed in structures of hOAT, PfOAT, and GABA-OAT from *E. coli*.[23,24,26,58,62] Residues from both monomers of the TgOAT dimer form the PLP-binding site. In the cavity the PLP molecule makes hydrogen bonds with T135, G136, A137, Y171, G172, E230, I256, D257, Q260, K286, S315, and T316 (FIG. 4). All of these residues are highly conserved in TgOAT and PJOAT structures. Exceptions were found between V75, A137, and Y171 residues, which in hOAT are substituted on phenylalanine, tyrosine and valine, respectively. Based on the electron density maps in the native TgOAT structure, the PLP doesn't form a Schiff base to the ε-amino group of the K286 in TgOAT monomers.

The structure of TgOAT with PLP bound to lysine 286 was obtained by co-crystallization with compound 11 (FIG. 3), but 11 was not observed at the active site of the enzyme. Comparison between TgOAT structures with PLP in a bound state and an unbound state to lysine 286 shows similar interactions between PLP and the protein residues (FIG. 4). There is a conformation change of the loop (50-54 residues) comprising the substrate-binding pocket in one of the monomers of TgOAT structure obtained in complex with the aldimine. In the TgOAT structure in presence of aldimine the pyridine ring of the PLP undergoes a rotation around C5 Å-O4P bond on 15° relatively to PLP in unbound state (FIG. 4). The overall position of the PLP in compared structures remains untouched with the small shift on 0.2 Å. The formation of the C4A=N bond at the right angle between the cofactor and K286 is an important feature of the OAT enzyme mechanism as it essential for proton transfer between PLP and the recognized substrate.

Structure of 18-Inactivated TgOAT.

Figure 5A:
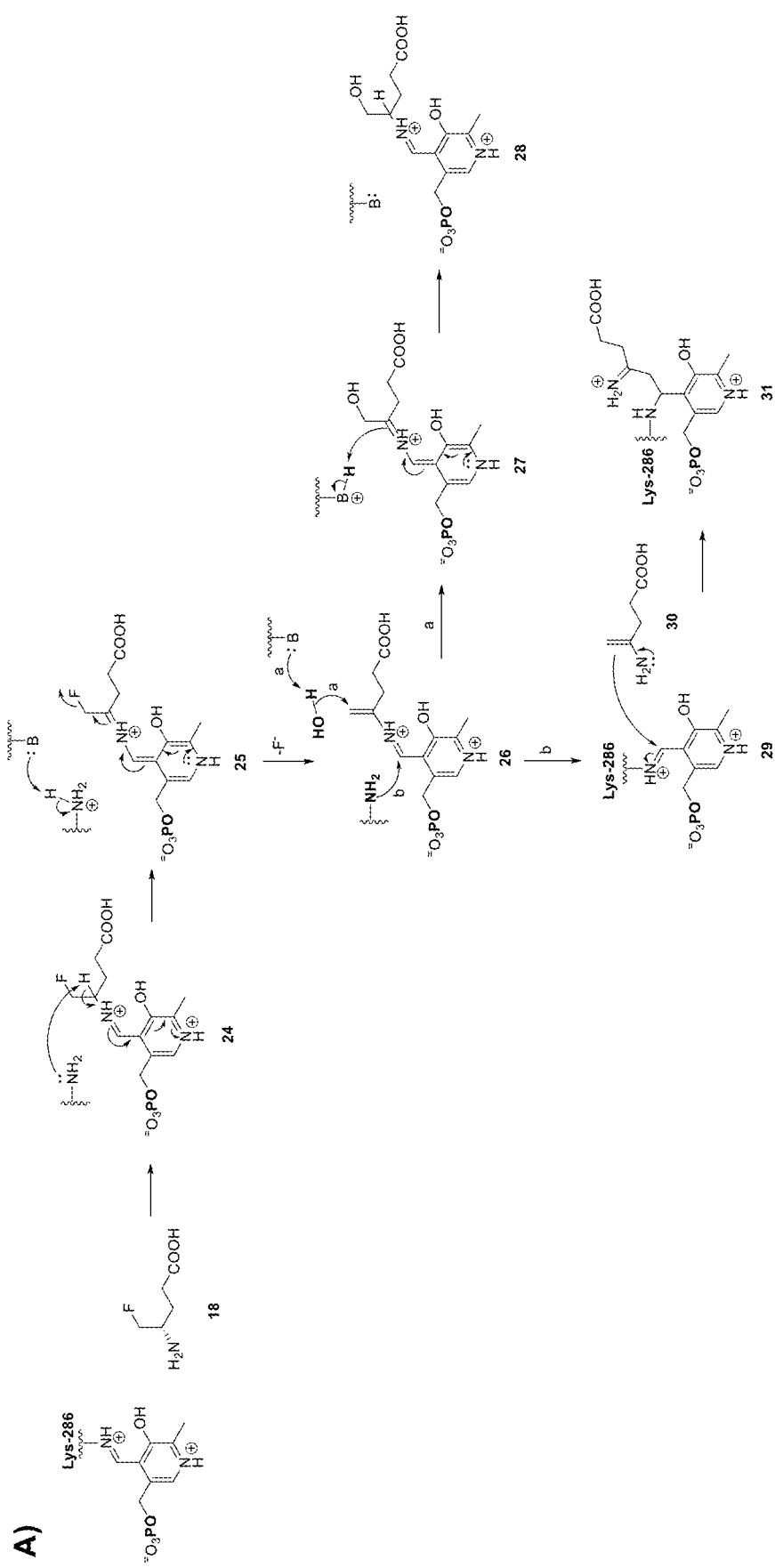
FIG. 5A. Inactivation mechanism of TgOAT by 18.
Figure 5B:
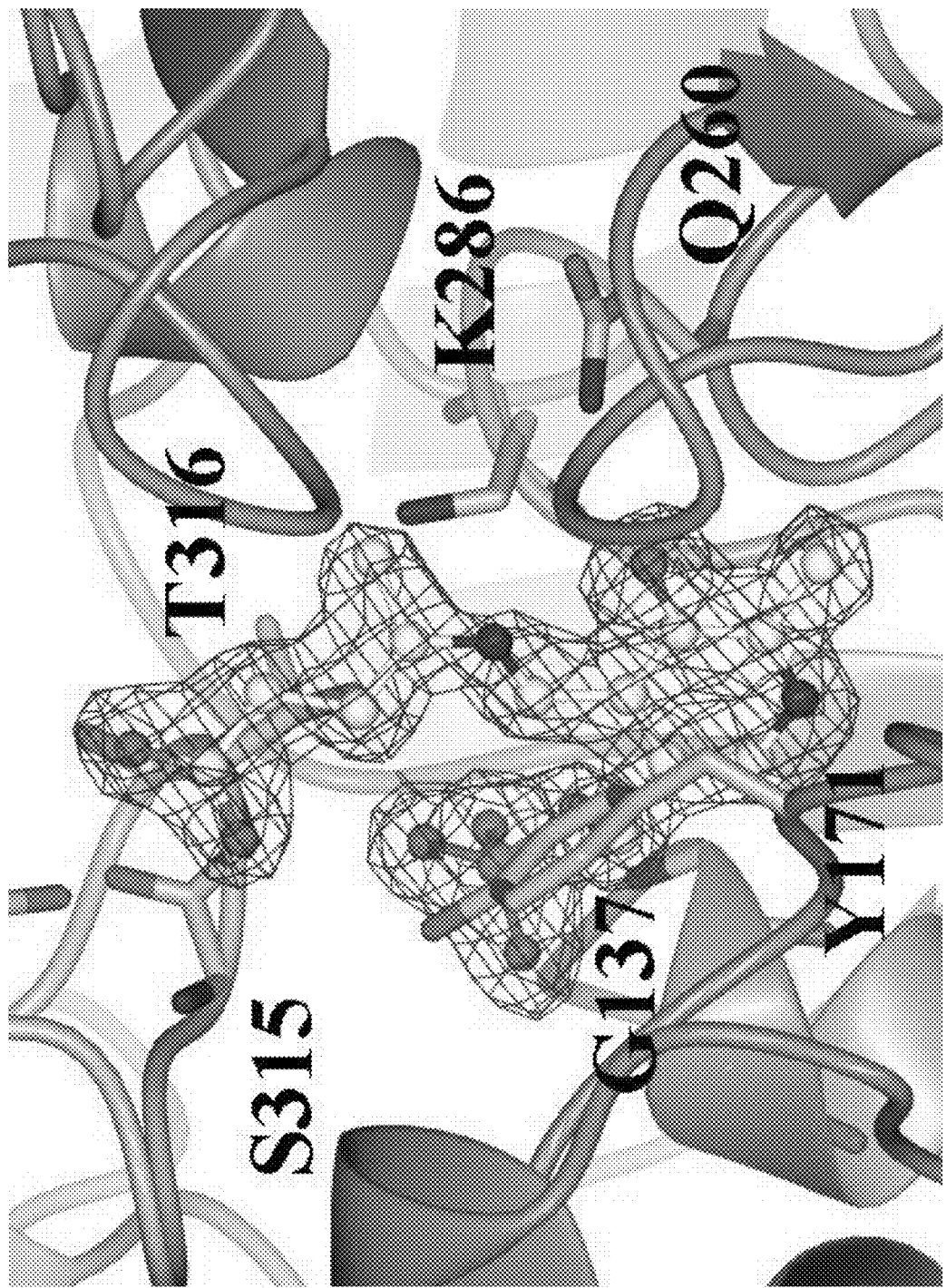
FIG. 5B. Omit map for 26 (ball-and-stick model).
Figure 5C:
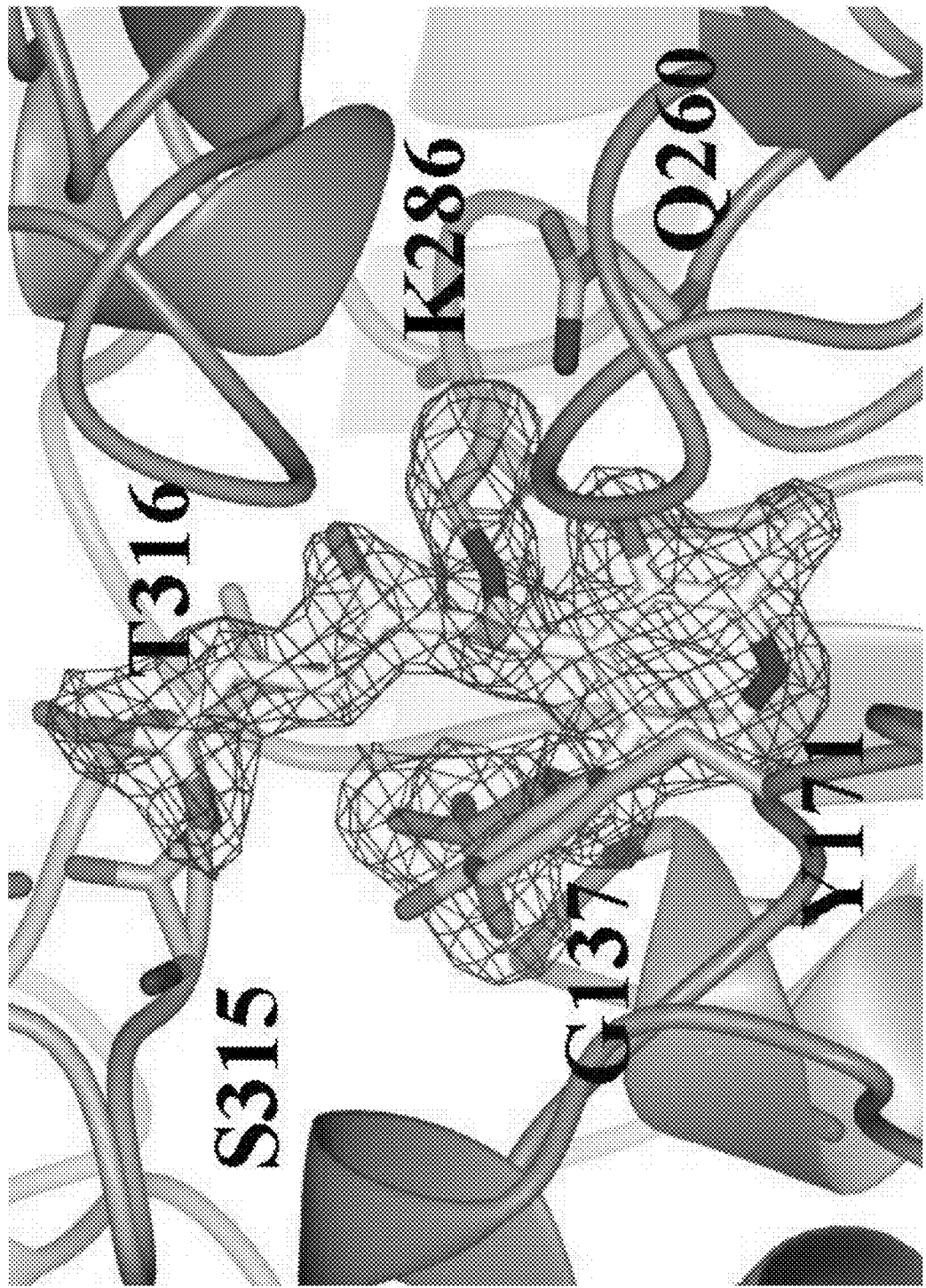
FIG. 5C. Omit map for 31 (cylinder model).
Figure 5D:
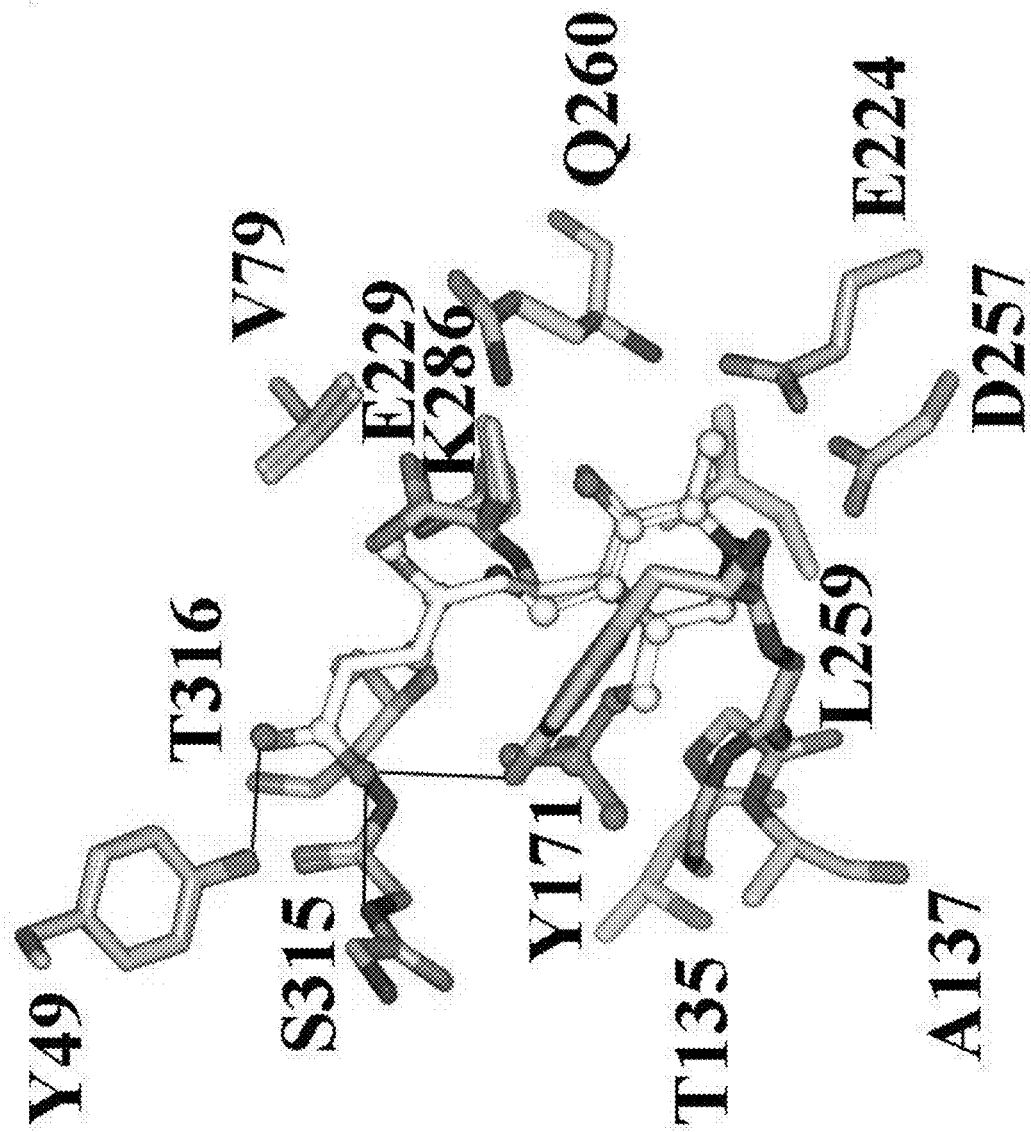
FIG. 5D. Superposition of 26 and 31 in the binding site. H-bonds are shown as bold lines.

The complex structures of TgOAT with intermediate metabolite 26 (FIG. 5A) and covalent adduct 31 (FIG. 5A) were determined by co-crystallization followed by 4 hours and 12 hours pre-incubation period with the compound 18, respectively. In the structures the amino group of the compound binds to the aldehyde position of the PLP via Schiff base. The final covalent adduct formed via Schiff base to K286 was identified in one of the protein monomers. The second monomer in the TgOAT structure in complex with the covalent adduct contains the compound in its intermediate state. In the structures, the compound occupies the TgOAT substrate-binding pocket that is formed by residues L76, G78, V79, N48, Y49, L106, R107, A108, Y171, R174, E229, K401, R409 and by H313, G314, S315, and T316 from the opposite monomer. In the pocket, the inactivator's carboxyl group makes strong interactions with OH atom of Y49 and N atom of the main chain of S315 from the opposite monomer. Additionally, the carboxyl group of the compound in TgOAT structures is mediated through water molecules with the side chain of atoms NH2 and OH of R174 and Y171, with main chain oxygen of S315, nitrogen of R107 and with O3P atom of the phosphate group of the cofactor (FIG. 5D). We have not observed conformational changes of the residues surrounding the substrate-binding site between compound-bound and compound-free state when TgOAT structures were compared.

Structure of Gabaculine-Inactivated TgOAT.

Figure 6:
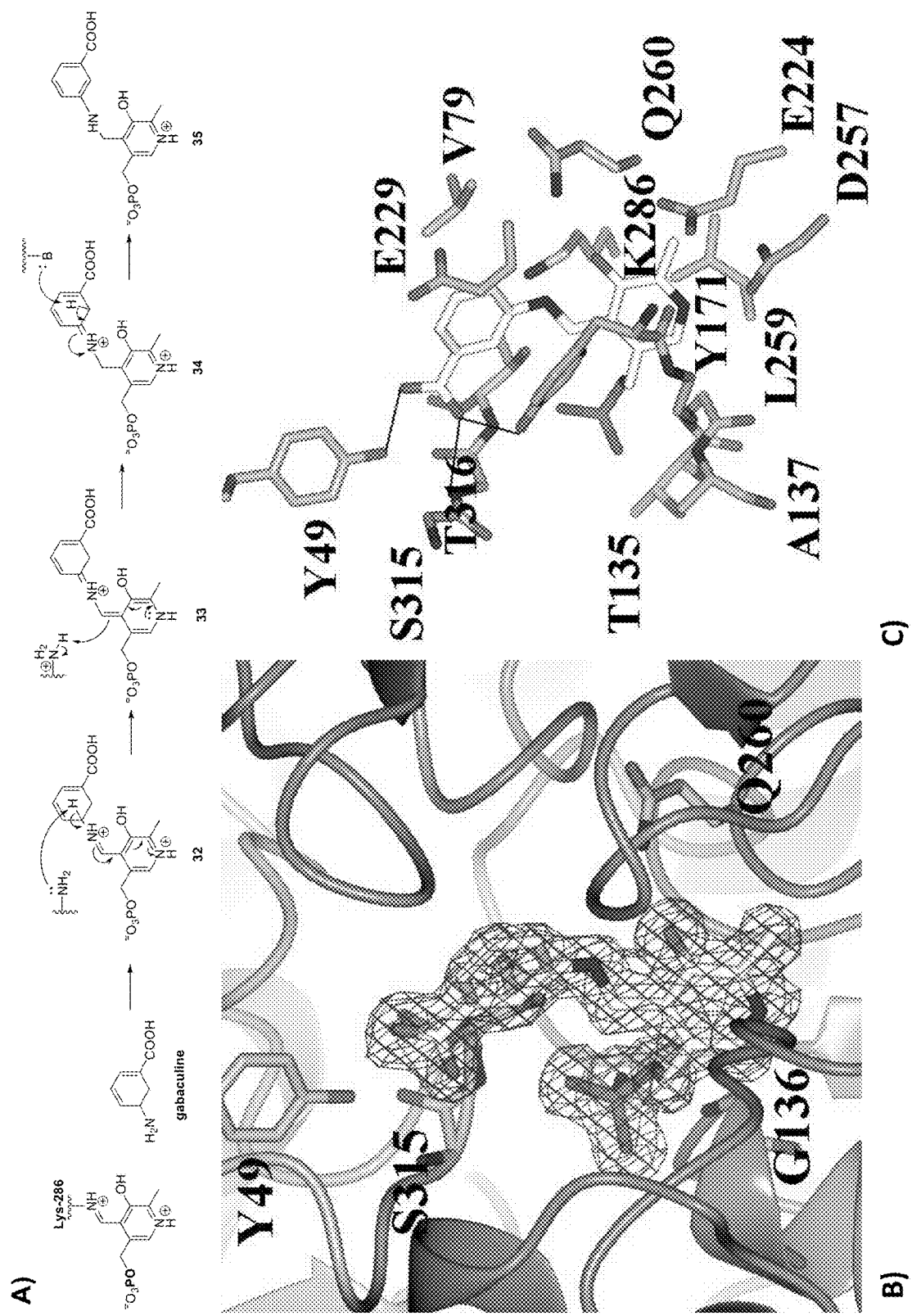
FIG. 6. (A) Inactivation mechanism of TgOAT by gabaculine. (B) Omit map for 35 (cylinder model). The electron density $2F_o$-$F_c$ omit map is shown at the 1σ contour level. (C) Compound 35 binding site. H-bonds are shown as bold lines.

To identify the specificity of TgOAT to gabaculine, which is an equally potent irreversible inhibitor of both human OAT and GABA-AT, we performed co-crystallization experiments with 5 mM gabaculine and obtained the TgOAT structure with gabaculine covalently bound to cofactor (FIG. 6B, 6C). Similarly to compound 18, the carboxylate group of the gabaculine interacts with OH atom of Y49 and N atom of the main chain of S315. The position of the gabaculine at the TgOAT active site is similar to its position observed in the structure of human OAT.[58] It has been shown that the interaction between aromatic ring of the gabaculine and protein's residues modulates binding affinity and keeps the product in a specific pose in the active site. The stacking favorable interaction between Y85 and F177 observed in the structure of human OAT.[58] It has been shown that mutation of these two residues greatly reduces activity of the human OAT enzyme.[57] Interestingly, that in the TgOAT structure, the Y85 (in hOAT) is substituted to V79. Therefore, the interaction between Y171 and the aromatic ring is sufficient to keep the product in that similar pose.

Inhibition on Tachyzoite Replication In Vitro.

None of the inactivators 1, 2, 5, 11, and 18 tested against Type I *T. gondii* tachyzoites showed statistically significant perturbation in vitro, even when the compounds were tested into the millimolar range. This indicates that these TgOAT inactivators have no effects on active *T. gondii* infection of human hosts.

Inhibition on *P. falciparum* In Vitro.

Compounds 1, 2, 5, and 11 were tested in the malaria SYBR Green fluorescence assay for drug potency against a drug sensitive *P. falciparum* parasite, D6 (Sierra Leone). All of the drugs tested showed IC50 values >10,000 ng/ml, and therefore were evaluated to have no detectable activity against *P. falciparum*.

Discussion

Figure 2:
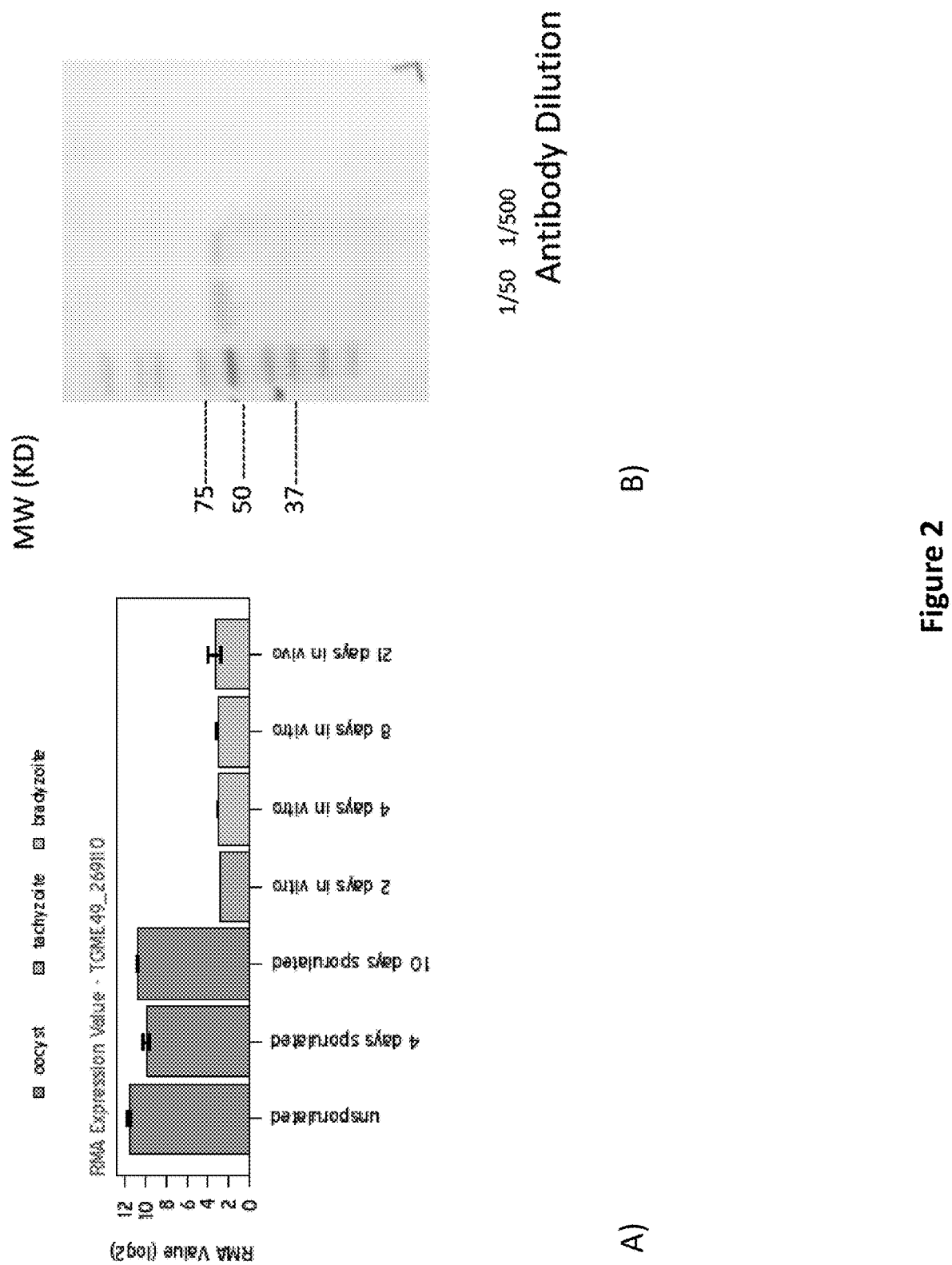
FIG. 2. Transcriptional and Protein Expression of TgOAT in the *T. gondii* Life Cycle Stages: (A) TgOAT mRNA is 256 times greater in sporozoites than in tachyzoites and bradyzoites. (B) Antibody to TgOAT reacts with recombinant protein in tachyzoite, bradyzoite, and sporozoite lysates.

After TgOAT was successfully expressed and purified from *E. coli*, its multi-sequence and phylogeny were analyzed. Multi-sequence alignment revealed substantial variation between the species, with the following percentage homologies with TgOAT: *H. hammondi*—96%, *N. caninum*—89%, *P. falciparum*—49%, *F. catus*—49%, *H. sapiens*—49%. This means OAT is markedly less conserved in *T. gondii* across evolution time. Parsimony analysis of the OAT sequence in 53 *T. gondii* isolates is consistent with established multi-gene phylogentic trees for isolates of *T. gondii*. The consensus tree consists of branches with clusters of several major haplotype groups: 1, 2, 3, 4, 11, 12, and 14. In ToxoDB and work of Boothroyd et al, expression of TgOAT was ~256 times higher in sporozoites than in tachyzoites and bradyzoites. This was confirmed using RT-PCR (FIG. 2).

For the past decades, we have developed many inhibitors and inactivators of γ-aminobutyric acid aminotransferase (GABA-AT), a PLP-dependent enzyme that degrades γ-aminobutyric acid (GABA), which is the major inhibitory neurotransmitter, for the treatment of epilepsy and many other neurological disorders.[67-70] It has been reported that some inactivators of GABA-AT, such as gabaculine and 4-amino-5-hexynoic acid, also inactivate human OAT in vitro and in vivo,[22,71] because the two enzymes share high structural similarities of their active sites.[21] Therefore, a library of 23 GABA analogues (FIG. 3) was screened against TgOAT for selective inactivators or inhibitors. Inactivators are unreactive compounds that require catalytic activity from the enzyme to convert them into reactive species that then inactivate the enzyme. Because these molecules are not initially reactive, indiscriminate reactions with off-target proteins should be greatly reduced. Usually, inactivators can achieve greater selectivity and potency than conventional inhibitors.[72] Compounds were chosen in the screened library because of their diversity in structures, including conformationally-rigid structures, aromatic structures, and flexible structures, in an attempt to identify different binding modes of the compounds to the active site of TgOAT. The kinetic constants for each compound are shown in Table 1. Of these compounds, 1, 2, 5, 11, and 18 have high activity in inactivating TgOAT. Results from other bioassays in our lab show that compound 1, also known as CPP-115 and recently finished a Phase I clinical trial for the treatment of epilepsy, is an extremely potent inactivator of GABA-AT[73] and a potent inactivator of human OAT[22]. Compound 2 is a weak reversible inhibitor of GABA-AT[74], but a highly potent inactivator of human OAT[22]. Compound 5 is a very weak reversible inhibitor of both GABA-AT[68] and human OAT[22]. Compound 11 is a weak reversible inhibitor of GABA-AT[v5] and a weak inactivator of human OAT[22]. Compound 18 is a moderate inactivator of both GABA-AT[76] and human OAT[22]. The screening has showed that while some strong inactivators of GABA-AT or human OAT, like 1 or 2, respectively, are also strong inactivators of TgOAT, other compounds, like 5, 11, and 18, have high specific inactivation towards TgOAT but not GABA-AT or human OAT. Thus, 5, 11, and 18 would offer a good starting point for the development of selective TgOAT inactivators.

Recombinant protein was also used to solve the crystal structures of native and inactivated TgOAT. The co-crystallization with the five identified inactivators (1, 2, 5, 11, and 18) and gabaculine, a potent inactivator of GABA-AT, yielded crystal structures of 18-inactivated and gabaculine-inactivated TgOAT. A proposed inactivation mechanism of TgOAT by 18 is shown in FIG. 5A. The inactivation is initiated by a Schiff base formation of 18 with the active site PLP, followed by γ-proton removal and release of fluoride, resulting in intermediate 26, which could either undergo catalytic hydrolysis to give aldimine 28 or return the PLP to lysine 286 and release enamine 30. Subsequent nucleophilic addition of 30 to the lysine-bound PLP gives rise to covalent adduct 31. Crystal structure of 18-inactivated TgOAT captured both intermediate 26 (FIG. 5B) and covalent adduct 31 (FIG. 5C). 18 was previously reported to inactivate GABA-AT by forming a corresponding covalent adduct in a similar fashion.[76] A proposed inactivation mechanism of TgOAT by gabaculine is shown in FIG. 6A. The inactivation is initiated by a Schiff base formation of gabaculine with the active site PLP, followed by γ-proton removal and tautomerization, resulting in intermediate 34, which then undergoes another proton removal to give the final aromatic product 35. Crystal structure of gabaculine-inactivated TgOAT confirmed the structure of 35 (FIG. 6B). Gabaculine was previously reported to inactivate GABA-AT and human OAT by forming corresponding aromatic products in a similar fashion.[58,77] The aromatic stabilization energy of the resulting benzene ring creates a large energy barrier to reversal and puts the product in a deep thermodynamic well, preventing the complex from further reaction.[78] The crystal structures of the inactivated TgOAT indicated that both 18 and gabaculine interacted with Y49 and S315 at the protein active site. No interaction between 18 and the conserved R174, which plays an essential role in recognition of specific inhibitors of human OAT, was observed.

There is conservation of a pair of cysteines in the apicomplexan OATs, but not in other species' OATs. In *P. falciparum*, C154 and C168 have been demonstrated to bind an activator, thioredoxin, which reduces protein disulfides via a disulfide-exchange mechanism.[23] One cysteine residue of the Cys-X-X-Cys motif on thioredoxin would perform a nucleophilic attack towards the disulfide of the target protein, resulting an intermolecular disulfide bond. The mixed-disulfide intermediate is subsequently cleaved, giving rise to a reduced protein and an oxidized thioredoxin.[23] Unlike PfOAT, the TgOAT sequence between two conserved cysteines (C154 and C179) is one residue shorter, which might affect the formation of the disulfide bond in the TgOAT structure. An attempt to oxidize the recombinant TgOAT using oxidized glutathione did not lead to the formation of disulfide bond between C179 and C187; crystal structure of the treated TgOAT showed that the two cysteines remained in the reduced state, suggesting C179 and C187 might not be activated by thioredoxin like the corresponding cysteines in PJOAT.

To determine the biologic phenotype of *T. gondii* in the presence, absence, or reduction of TgOAT, two approaches were utilized. For Type I parasites, morpholino linked to a molecular transporter (PPMO) was utilized to alternatively splice the TgOAT gene. In the Type I strain, in vitro analysis demonstrated modest inhibition of replication (data not shown). The slower replicating Type II parasites were studied by making a knockout of the TgOAT gene. However, this knockout had no virulence phenotype, either in vitro or in vivo, and neither survival nor cyst number were altered significantly (data not shown). This left us with a modest phenotype in rapidly replicating parasites, and no obvious phenotype in the slower-growing Type IIs. Thus, inhibition of TgOAT was not likely to significantly modify outcomes due to active or dormant infection in humans. This finding, in conjunction with the observations of the 256-fold increase in expression of TgOAT in sporozoites, led to our hypothesis that inhibition of the enzyme in the cat form might be useful in blocking transmission of the parasite. Further studies are being conducted in this direction; if inhibition of TgOAT eliminates shedding of infectious oocysts into the environment, this would have the potential to prevent diseases caused by *T. gondii* and consequent infection present in the human population and in livestock animals. The compounds 1, 2, 5, 11, and 18 were also tested against the growth of *P. falciparum*. However, a live-cell parasite assay revealed the compounds had no antimalarial activity at concentrations up to 10000 ng/mL (data not shown).

Conclusion

Ornithine aminotransferase is an important enzyme that plays a crucial role in preventing toxic accumulation of ornithine in the cell. A selective inhibition of OAT in *T. gondii* over human OAT might render a solution in the fight against this parasite. We have characterized a number of features of TgOAT: the gene, protein, abundance in different life cycle stages, and enzyme activity. A screening of our library of 23 GABA analogues resulted in several selective inactivators of TgOAT. Crystal structures of the native and inactivated enzymes were obtained. Two different inactivation mechanisms of two different inactivators were identified: one by gabaculine, which inactivated the enzyme by forming an aromatic ring inside the active site, and the other by (S)-4-amino-5-fluoropentanoic acid, 18, which inactivated the enzyme by forming a covalent adduct to the enzyme. These newly identified TgOAT inactivators and insights of the enzyme binding pocket from crystal structures lay a foundation of further studies of selective inactivation of TgOAT and drug development.

TABLE 1

Kinetic Constants for GABA Analogues Against TgOAT

| Compound | $K_I$ (mM) | $k_{inact}$ (min$^{-1}$) | $k_{inact}/K_I$ (mM$^{-1}$ min$^{-1}$) | $K_i$ (mM) |
|---|---|---|---|---|
| 1 (CPP-115) | 0.0044 | 11 | 2500 | — |
| 2 | 0.0048 | 4.4 | 920 | — |
| 3 | 0.030 | 0.15 | 5.0 | — |
| 4 | 0.021 | 0.23 | 11 | — |
| 5 | 0.015 | 4.4 | 290 | — |
| 6 | 0.021 | 0.21 | 10 | — |
| 7 | 2.1 | 11 | 5.2 | — |
| 8 | 0.13 | 7.8 | 60 | — |
| 9 | 2.6 | 5.0 | 1.9 | — |
| 10 | 0.11 | 3.9 | 35 | — |
| 11 | 0.015 | 5.4 | 360 | — |
| 12 | — | — | — | 2.9 |
| 13 | — | — | — | >5 |
| 14 | — | — | — | 4.2 |
| 15 | — | — | — | 4.9 |
| 16 | — | — | — | >5 |
| 17 | — | — | — | >5 |
| 18 | 0.0046 | 10 | 2200 | — |
| 19 | 0.048 | 0.22 | 4.6 | — |
| 20 | — | — | — | >5 |
| 21 | — | — | — | >5 |
| 22 (vigabatrin) | 0.44 | 9.9 | 23 | — |
| 23 (gabaculine) | 0.00082 | 8.7 | 11000 | — |

TABLE 2

Collection and Refinement Statistics for
Crystallographic Data for TgOAT$^a$
A. Data Collection

| Space group | P1 |
|---|---|
| Unit cell parameters (Å; °) | a = 56.2, b = 61.3, c = 63.7; α = 100.6, β = 93.2, γ = 107.7 |
| Resolution range (Å) | 62.1-1.2 (1.22-1.20) |
| No. of reflections | 224,574 (11,241) |
| $R_{merge}$ (%) | 4.3 (37.0) |
| Completeness (%) | 91.0 (91.0) |
| <I/σ(I)> | 11.2 (2.0) |
| Multiplicity | 2.0 (2.0) |
| Wilson B factor | 14.4 |
| Refinement | |
| Resolution range (Å) | 62.1-1.2 (1.23-1.20) |
| Completeness (%) | 90.8 (90.0) |
| No. of reflections | 213,305 (15,538) |
| $R_{work}/R_{free}$, (%) | 13.3/16.5 (20.9/23.8) |
| Protein molecules/atoms | 2/6,560 |
| Solvent atoms | 1,041 |
| Mean temperature factor (Å) | 18.4 |
| Coordinate deviation | |
| R.m.s.d. bonds (Å) | 0.021 |
| R.m.s.d. angles (°) | 1.927 |
| Ramachandran plot† | |
| Most favored (%) | 90.2 |
| Allowed (%) | 9.0 |

TABLE 2-continued

Collection and Refinement Statistics for
Crystallographic Data for TgOAT$^a$
A. Data Collection

| Generously allowed (%) | 0.3 |
|---|---|
| Outside allowed (%) | 0.5 |

$^a$Statistics are based on PROCHECK.
[79] Values in parentheses are for the highest resolution shell.

REFERENCES (1) CDC—Toxoplasmosis.
(2) Montoya, J. G.; Liesenfeld, O. Lancet 2004, 363 (9425), 1965-1976.
(3) Hill, D.; Dubey, J. P. Clin. Microbiol. Infect. 2002, 8 (10), 634-640.
(4) Dabritz, H. A.; Miller, M. A.; Atwill, E. R.; Gardner, I. A.; Leutenegger, C. M.; Melli, A. C.; Conrad, P. A. J. Am. Vet. Med. Assoc. 2007, 231 (11), 1676-1684.
(5) Yilmaz, S. M.; Hopkins, S. H. J. Parasitol. 1972, 58 (5), 938-939.
(6) Jk, F.; A, R.; M, C. Am. J. Trop. Med. Hyg. 1975, 24 (3), 439-443.
(7) Dubey, J. P. J. Parasitol. 1998, 84 (4), 862-865.
(8) Sj, A.; Mc, K.; Ms, M.; S, D.; Ma, S. Arch. Pathol. Lab. Med. 1997, 121 (8), 869-873.
(9) Petersen, E.; Liesenfeld, O. In *Toxoplasma Gondii*; Weiss, L. M., Kim, K., Eds.; Academic Press: London, 2007; pp 81-100.
(10) Burrowes, D.; Boyer, K.; Swisher, C. N.; Noble, A. G.; Sautter, M.; Heydemann, P.; Rabiah, P.; Lee, D.; McLeod, R.; the Toxoplasmosis Study Group. J. Neuroparasitology 2012, 3 (2012).
(11) McLeod, R.; Lykins, J.; Noble, A. G.; Rabiah, P.; Swisher, C. N.; Heydemann, P. T.; McLone, D.; Frim, D.; Withers, S.; Clouser, F.; Boyer, K. Curr. Pediatr. Rep. 2014, 2 (3), 166-194.
(12) World Malaria Report, 2014; World Health Organization: Geneva, Switzerland, 2014.
(13) Waxman, S.; Herbert, V. N. Engl. J. Med. 1969, 280 (24), 1316-1319.
(14) Caumes, E.; Bocquet, H.; Guermonprez, G.; Rogeaux, O.; Bricaire, F.; Katlama, C.; Gentilini, M. Clin. Infect. Dis. 1995, 21 (3), 656-658.
(15) McLeod, R.; Khan, A. R.; Noble, G. A.; Latkany, P.; Jalbrzikowski, J.; Boyer, K. Pediatr. Infect. Dis. J. 2006, 25 (3), 270-272.
(16) Neafsey, D. E. Nat. Genet. 2013, 45 (6), 589-590.
(17) Rosenthal, P. J. Mol. Microbiol. 2013, 89 (6), 1025-1038.
(18) Aguero, F.; Al-Lazikani, B.; Aslett, M.; Berriman, M.; Buckner, F. S.; Campbell, R. K.; Carmona, S.; Carruthers, I. M.; Chan, A. W. E.; Chen, F.; Crowther, G. J.; Doyle, M. A.; Hertz-Fowler, C.; Hopkins, A. L.; McAllister, G.; Nwaka, S.; Overington, J. P.; Pain, A.; Paolini, G. V.; Pieper, U.; Ralph, S. A.; Riechers, A.; Roos, D. S.; Sali, A.; Shanmugam, D.; Suzuki, T.; Van Voorhis, W. C.; Verlinde, C. L. M. J. Nat. Rev. Drug Discov. 2008, 7 (11), 900-907.
(19) Magarifios, M. P.; Carmona, S. J.; Crowther, G. J.; Ralph, S. A.; Roos, D. S.; Shanmugam, D.; Voorhis, W. C. Van; Agilero, F. Nucleic Acids Res. 2012, 40 (D1), D1118-D1127.
(20) Seiler, N. Curr. Drug Targets 2000, 1 (2), 119-153.
(21) Lee, H.; Juncosa, J. I.; Silverman, R. B. Med. Res. Rev. 2015, 35 (2), 286-305.

(22) Zigmond, E.; Ya'acov, A. Ben; Lee, H.; Lichtenstein, Y.; Shalev, Z.; Smith, Y.; Zolotarov, L.; Ziv, E.; Kalman, R.; Le, H. V.; Lu, H.; Silverman, R. B.; Ilan, Y. ACS Med. Chem. Lett. 2015, 150708125556004.

(23) Jortzik, E.; Fritz-Wolf, K.; Sturm, N.; Hipp, M.; Rahlfs, S.; Becker, K. J. Mol. Biol. 2010, 402 (2), 445-459.

(24) Vedadi, M.; Lew, J.; Artz, J.; Amani, M.; Zhao, Y.; Dong, A.; Wasney, G. A.; Gao, M.; Hills, T.; Brokx, S.; Qiu, W.; Sharma, S.; Diassiti, A.; Alam, Z.; Melone, M.; Mulichak, A.; Wernimont, A.; Bray, J.; Loppnau, P.; Plotnikova, O.; Newberry, K.; Sundararajan, E.; Houston, S.; Walker, J.; Tempel, W.; Bochkarev, A.; Kozieradzki, I.; Edwards, A.; Arrowsmith, C.; Roos, D.; Kain, K.; Hui, R. Mol. Biochem. Parasitol. 2007, 151 (1), 100-110.

(25) Sievers, F.; Wilm, A.; Dineen, D.; Gibson, T. J.; Karplus, K.; Li, W.; Lopez, R.; McWilliam, H.; Remmert, M.; Soding, J.; Thompson, J. D.; Higgins, D. G. Mol. Syst. Biol. 2011, 7 (1), 539.

(26) Shen, B. W.; Hennig, M.; Hohenester, E.; Jansonius, J. N.; Schirmer, T. J. Mol. Biol. 1998, 277 (1), 81-102.

(27) Gafan, C.; Wilson, J.; Berger, L. C.; Berger, B. J. Mol. Biochem. Parasitol. 2001, 118 (1), 1-10.

(28) Aslanidis, C.; de Jong, P. J. Nucleic Acids Res. 1990, 18 (20), 6069-6074.

(29) Minor, W.; Cymborowski, M.; Otwinowski, Z.; Chruszcz, M. Acta Crystallogr. Sect. D Biol. Crystallogr. 2006, 62 (8), 859-866.

(30) McCoy, A. J.; Grosse-Kunstleve, R. W.; Adams, P. D.; Winn, M. D.; Storoni, L. C.; Read, R. J. J. Appl. Crystallogr. 2007, 40 (4), 658-674.

(31) Winn, M. D.; Ballard, C. C.; Cowtan, K. D.; Dodson, E. J.; Emsley, P.; Evans, P. R.; Keegan, R. M.; Krissinel, E. B.; Leslie, A. G. W.; McCoy, A.; McNicholas, S. J.; Murshudov, G. N.; Pannu, N. S.; Potterton, E. A.; Powell, H. R.; Read, R. J.; Vagin, A.; Wilson, K. S. Acta Crystallogr. D. Biol. Crystallogr. 2011, 67 (Pt 4), 235-242.

(32) Morris, R. J.; Perrakis, A.; Lamzin, V. S. In Methods in Enzymology; Elsevier, 2003; Vol. 374, pp 229-244.

(33) Emsley, P.; Cowtan, K. Acta Crystallogr. Sect. D Biol. Crystallogr. 2004, 60 (12), 2126-2132.

(34) Emsley, P.; Lohkamp, B.; Scott, W. G.; Cowtan, K. Acta Crystallogr. Sect. D Biol. Crystallogr. 2010, 66 (4), 486-501.

(35) Murshudov, G. N.; Skubk, P.; Lebedev, A. A.; Pannu, N. S.; Steiner, R. A.; Nicholls, R. A.; Winn, M. D.; Long, F.; Vagin, A. A. Acta Crystallogr. Sect. D Biol. Crystallogr. 2011, 67 (4), 355-367.

(36) Painter, J.; Merritt, E. A. Acta Crystallogr. Sect. D Biol. Crystallogr. 2006, 62 (4), 439-450.

(37) Painter, J.; Merritt, E. A. J. Appl. Crystallogr. 2006, 39 (1), 109-111.

(38) Davis, I. W.; Leaver-Fay, A.; Chen, V. B.; Block, J. N.; Kapral, G. J.; Wang, X.; Murray, L. W.; Arendall, W. B.; Snoeyink, J.; Richardson, J. S.; Richardson, D. C. Nucleic Acids Res. 2007, 35 (suppl 2), W375-W383.

(39) Chen, V. B.; Arendall, W. B.; Headd, J. J.; Keedy, D. A.; Immormino, R. M.; Kapral, G. J.; Murray, L. W.; Richardson, J. S.; Richardson, D. C. Acta Crystallogr. Sect. D Biol. Crystallogr. 2010, 66 (1), 12-21.

(40) Holm, L.; Rosenstrim, P. Nucleic Acids Res. 2010, 38, W545-W549.

(41) Madej, T.; Lanczycki, C. J.; Zhang, D.; Thiessen, P. A.; Geer, R. C.; Marchler-Bauer, A.; Bryant, S. H. Nucleic Acids Res. 2014, 42 (D1), D297-D303.

(42) Laskowski, R. A.; Watson, J. D.; Thornton, J. M. Nucleic Acids Res. 2005, 33 (Web Server), W89-W93.

(43) McNicholas, S.; Potterton, E.; Wilson, K. S.; Noble, M. E. M. Acta Crystallogr. D. Biol. Crystallogr. 2011, 67 (Pt 4), 386-394.

(44) Moulton, H. M.; Moulton, J. D. Biochim. Biophys. Acta—Biomembr. 2010, 1798 (12), 2296-2303.

(45) Bedell, V. M.; Westcot, S. E.; Ekker, S. C. Brief. Funct. Genomics 2011, 10 (4), 181-188.

(46) Cirak, S.; Arechavala-Gomeza, V.; Guglieri, M.; Feng, L.; Torelli, S.; Anthony, K.; Abbs, S.; Garralda, M. E.; Bourke, J.; Wells, D. J.; Dickson, G.; Wood, M. J.; Wilton, S. D.; Straub, V.; Kole, R.; Shrewsbury, S. B.; Sewry, C.; Morgan, J. E.; Bushby, K.; Muntoni, F. Lancet 2011, 378 (9791), 595-605.

(47) Lai, B.-S.; Witola, W. H.; Bissati, K. El; Zhou, Y.; Mui, E.; Fomovska, A.; McLeod, R. Proc. Natl. Acad. Sci. 2012, 201208775.

(48) Daune, G.; Seiler, N. Neurochem. Res. 1988, 13 (1), 69-75.

(49) Johnson, J. D.; Dennull, R. A.; Gerena, L.; Lopez-Sanchez, M.; Roncal, N. E.; Waters, N. C. Antimicrob. Agents Chemother. 2007, 51 (6), 1926-1933.

(50) Plouffe, D.; Brinker, A.; McNamara, C.; Henson, K.; Kato, N.; Kuhen, K.; Nagle, A.; Adrian, F.; Matzen, J. T.; Anderson, P.; Nam, T.; Gray, N. S.; Chatterjee, A.; Janes, J.; Yan, S. F.; Trager, R.; Caldwell, J. S.; Schultz, P. G.; Zhou, Y.; Winzeler, E. A. Proc. Natl. Acad. Sci. 2008, 105 (26), 9059-9064.

(51) Su, C.; Khan, A.; Zhou, P.; Majumdar, D.; Ajzenberg, D.; Darde, M.-L.; Zhu, X.-Q.; Ajioka, J. W.; Rosenthal, B. M.; Dubey, J. P.; Sibley, L. D. Proc. Natl. Acad. Sci. 2012, 109 (15), 5844-5849.

(52) Juncosa, J. I.; Lee, H.; Silverman, R. B. Anal. Biochem. 2013, 440 (2), 145-149.

(53) Rover Júnior, L.; Fernandes, J. C.; de Oliveira Neto, G.; Kubota, L. T.; Katekawa, E.; Serrano, S. H. Anal. Biochem. 1998, 260 (1), 50-55.

(54) Kiianitsa, K.; Solinger, J. A.; Heyer, W.-D. Anal. Biochem. 2003, 321 (2), 266-271.

(55) Michaelis, L.; Menten, M. L.; Johnson, K. A.; Goody, R. S. Biochemistry 2011, 50 (39), 8264-8269.

(56) Salminen, K. A.; Leppinen, J.; Venilinen, J. I.; Pasanen, M.; Auriola, S.; Juvonen, R. O.; Raunio, H. Drug Metab. Dispos. 2011, 39 (3), 412-418.

(57) Markova, M.; Peneff, C.; Hewlins, M. J. E.; Schirmer, T.; John, R. A. J. Biol. Chem. 2005, 280 (43), 36409-36416.

(58) Shah, S. A.; Shen, B. W.; Brunger, A. T. Structure 1997, 5 (8), 1067-1075.

(59) Kabsch, W. Acta Crystallogr. Sect. A 1976, 32 (5), 922-923.

(60) Christen, P.; Metzler, D. E. Transaminases; Wiley: New York, 1985.

(61) Mehta, P. K.; Hale, T. I.; Christen, P. Eur. J. Biochem. 1993, 214 (2), 549-561.

(62) Storici, P.; Capitani, G.; Müller, R.; Schirmer, T.; Jansonius, J. N. J. Mol. Biol. 1999, 285 (1), 297-309.

(63) Liu, W.; Peterson, P. E.; Carter, R. J.; Zhou, X.; Langston, J. A.; Fisher, A. J.; Toney, M. D. Biochemistry 2004, 43 (34), 10896-10905.

(64) Berman, H. M.; Westbrook, J.; Feng, Z.; Gilliland, G.; Bhat, T. N.; Weissig, H.; Shindyalov, I. N.; Bourne, P. E. Nucleic Acids Res. 2000, 28 (1), 235-242.

(65) Baugh, L.; Phan, I.; Begley, D. W.; Clifton, M. C.; Armour, B.; Dranow, D. M.; Taylor, B. M.; Muruthi, M. M.; Abendroth, J.; Fairman, J. W.; Fox, D.; Dieterich, S. H.; Staker, B. L.; Gardberg, A. S.; Choi, R.; Hewitt, S. N.; Napuli, A. J.; Myers, J.; Barrett, L. K.; Zhang, Y.; Ferrell, M.; Mundt, E.; Thompkins, K.; Tran, N.; Lyons-Abbott, S.; Abramov, A.; Sekar, A.; Serbzhinskiy, D.; Lorimer, D.; Buchko, G. W.; Stacy, R.; Stewart, L. J.; Edwards, T. E.; Van Voorhis, W. C.; Myler, P. J. Tuberculosis 2015, 95 (2), 142-148.
(66) Newman, J.; Seabrook, S.; Surjadi, R.; Williams, C. C.; Lucent, D.; Wilding, M.; Scott, C.; Peat, T. S. PLoS One 2013, 8 (3), e58298.
(67) Silverman, R. B. J. Med. Chem. 2012, 55 (2), 567-575.
(68) Yuan, H.; Silverman, R. B. Bioorganic Med. Chem. Lett. 2007, 17 (6), 1651-1654.
(69) Wang, Z.; Yuan, H.; Nikolic, D.; Van Breemen, R. B.; Silverman, R. B. Biochemistry 2006, 45 (48), 14513-14522.
(70) Yuan, H.; Silverman, R. B. Bioorganic Med. Chem. 2006, 14 (5), 1331-1338.
(71) Jung, M. J.; Seiler, N. J. Biol. Chem. 1978, 253 (20), 7431-7439.
(72) Singh, J.; Petter, R. C.; Baillie, T. A.; Whitty, A. Nat. Rev. Drug Discov. 2011, 10 (4), 307-317.
(73) Pan, Y.; Qiu, J.; Silverman, R. B. J. Med. Chem. 2003, 46 (25), 5292-5293.
(74) Lu, H.; Silverman, R. B. J. Med. Chem. 2006, 49 (25), 7404-7412.
(75) Hawker, D. D. Ph.D. Diss. Northwest. Univ. 2013.
(76) Silverman, R. B.; Invergo, B. J. Biochemistry 1986, 25 (22), 6817-6820.
(77) Rando, R. R.; Bangerter, F. W. J. Am. Chem. Soc. 1976, 98 (21), 6762-6764.
(78) Frey, P. A.; Ables, R. H. Enzymatic Reaction Mechanisms; Oxford University Press, USA, 2006.
(79) Laskowski, R. A.; MacArthur, M. W.; Moss, D. S.; Thornton, J. M. J. Appl. Crystallogr. 1993, 26 (2), 283-291.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound having a formula:

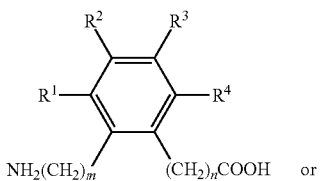

or

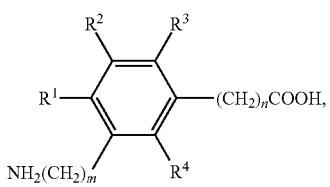

wherein:

m is 1-6;

n is 0-6; and

R², R³ and R⁴ may be the same or different and are selected from hydrogen, halo, and C1-C6 alkyl which may be straight chain or branched and may be substituted at one or more positions with halo.

2. A pharmaceutical composition comprising the compound of claim 1 together with a pharmaceutical carrier or excipient.

3. The compound of claim 1, wherein the compound has a formula:

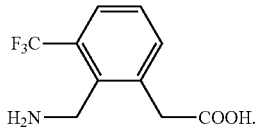

4. The compound of claim 1, wherein the compound has a formula:

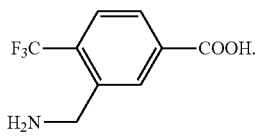

5. The compound of claim 1, wherein the compound has a formula:

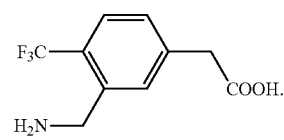

6. A compound having a formula:

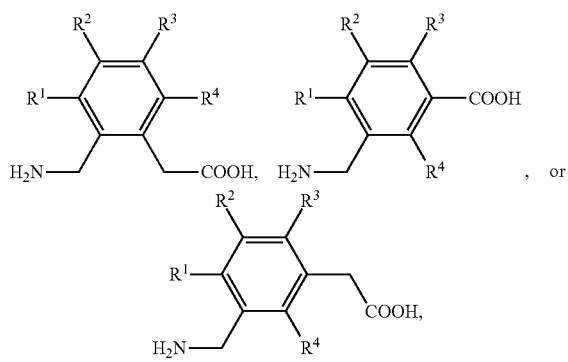

wherein:
$R^2$, $R^3$ and $R^4$ may be the same or different and are selected from hydrogen, halo, and C1-C6 alkyl which may be straight chain or branched and may be substituted at one or more positions with halo.

7. A pharmaceutical composition comprising the compound of claim 6 together with a pharmaceutical carrier or excipient.

8. A method for treating a subject infected with an Apicomplexan parasite, the method comprising administering to the subject an effective amount of the compound of claim 6 that selectively inactivates ornithine aminotransferase of the Apicomplexan parasite.

9. A compound having a formula:

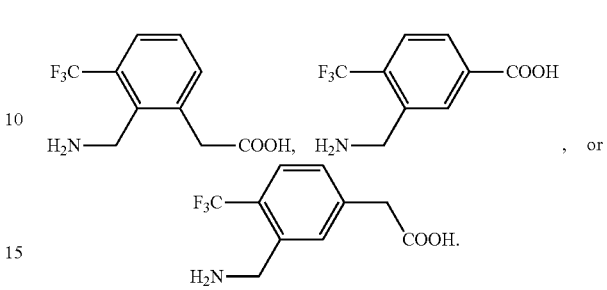

10. A pharmaceutical composition comprising the compound of claim 9 together with a pharmaceutical carrier or excipient.

11. A method for treating a subject infected with an Apicomplexan parasite, the method comprising administering to the subject an effective amount of the compound of claim 9 that selectively inactivates ornithine aminotransferase of the Apicomplexan parasite.

* * * * *

SEQUENCE LISTING

<160> NUMBER OF SEQ ID NOS: 7

<210> SEQ ID NO 1
<211> LENGTH: 409
<212> TYPE: PRT
<213> ORGANISM: Toxoplasma gondii

<400> SEQUENCE: 1

Met Ala Thr Lys Ser Asp Gly Ser Ala Ser Ala Ala Ala Glu Gly Gly
1               5                   10                  15

Ala Arg Lys Thr Asn Ile Glu Ala Tyr Arg Asp Gly Leu Lys Leu Lys
                20                  25                  30

Thr Glu Glu Asp Phe Phe Ala Cys Asp Arg Gln Tyr Val Cys Gln Asn
            35                  40                  45

Tyr Ala Pro Val Pro Val Val Ile Ser Lys Gly Lys Gly Ala Arg Val
        50                  55                  60

Trp Asp Ile Asn Gly Asn Glu Tyr Tyr Asp Phe Leu Ala Gly Val Ser
65                  70                  75                  80

Ser Leu Ser Gln Gly His Cys His Pro Arg Val Ile Ala Ala Leu Cys
                85                  90                  95

Arg Gln Ala Glu Arg Leu Thr Leu Thr Leu Arg Ala Phe Gly Asn Asp
            100                 105                 110

Val Thr Gly Pro Ala Cys Arg Phe Met Ala Glu Met Phe Gly Tyr Asp
        115                 120                 125

Arg Val Leu Leu Met Asn Thr Gly Ala Glu Ala Gly Glu Ser Ala Leu
    130                 135                 140

Lys Ile Ala Arg Lys Trp Ala Tyr Glu Val Lys Glu Ile Pro Pro Asp
145                 150                 155                 160

Ser Ala Lys Val Ile Leu Cys Asn Asn Asn Tyr Trp Gly Arg Thr Ile
            165                 170                 175

Thr Ala Cys Ser Ser Thr Thr Phe Asp Cys Tyr Asn Asn Phe Gly
        180                 185                 190

Pro Phe Thr Pro Gly Phe Glu Leu Ile Asp Tyr Asp Val Gly Ala
        195                 200                 205

Leu Glu Glu Ala Leu Lys Asp Pro Asn Val Ala Ala Phe Phe Val Glu
            210                 215                 220

Pro Ile Gln Gly Glu Gly Val Asn Val Pro Lys Pro Gly Tyr Leu
225                 230                 235                 240

Lys Arg Ala His Glu Leu Cys Arg Ser Lys Asn Val Leu Leu Ile Val
                245                 250                 255

Asp Glu Ile Gln Thr Gly Leu Cys Arg Thr Gly Arg Leu Leu Ala Ala
            260                 265                 270

Asp His Asp Glu Val His Pro Asp Ile Leu Leu Gly Lys Ser Leu
        275                 280                 285

Ser Ala Gly Val Val Pro Ile Ser Ala Val Met Gly Arg Ala Asp Val
            290                 295                 300

Met Asp Val Leu Lys Pro Gly Thr His Gly Ser Thr Phe Gly Gly Asn
305                 310                 315                 320

Pro Leu Ala Cys Ala Val Ala Val Glu Ala Leu Thr Val Leu Lys Asp
                325                 330                 335

Glu Lys Leu Ala Asp Arg Ala Glu Arg Leu Gly Ala Gln Phe Arg Asp
            340                 345                 350

Cys Leu Arg Arg Glu Leu Tyr Gly Lys Val Pro Trp Ile Lys Glu Ile
        355                 360                 365

Arg Gly Arg Gly Leu Leu Asn Ala Val Glu Val Asp Ser Asp Ala Ile
370                 375                 380

Asp Pro Asn Asp Val Val Met Lys Leu Lys Glu Asn Gly Ile Leu Ser
385                 390                 395                 400

Lys Pro Thr Arg Gly Arg Val Met Arg
                405

<210> SEQ ID NO 2
<211> LENGTH: 384
<212> TYPE: PRT
<213> ORGANISM: Plasmodium falciparum

<400> SEQUENCE: 2

Met Asp Phe Val Lys Glu Leu Lys Ser Ser Gln Asp Tyr Met Asn Asn
1               5                   10                  15

Glu Leu Thr Tyr Gly Ala His Asn Tyr Asp Pro Ile Pro Val Val Leu
            20                  25                  30

Lys Arg Gly Lys Gly Val Phe Val Tyr Asp Ile Glu Asp Arg Arg Tyr
        35                  40                  45

Tyr Asp Phe Leu Ser Ala Tyr Ser Ser Val Asn Gln Gly His Cys His
    50                  55                  60

Pro Asp Ile Leu Asn Ala Met Ile Asn Gln Ala Lys Lys Leu Thr Ile
65                  70                  75                  80

Cys Ser Arg Ala Phe Phe Ser Asp Ser Leu Gly Val Cys Glu Arg Tyr
                85                  90                  95

Leu Thr Asn Leu Phe Gly Tyr Asp Lys Val Leu Met Met Asn Thr Gly
            100                 105                 110

Ala Glu Ala Ser Glu Thr Ala Tyr Lys Leu Cys Arg Lys Trp Gly Tyr
        115                 120                 125

```
Glu Val Lys Lys Ile Pro Glu Asn Ser Ala Lys Ile Ile Val Cys Asn
        130                 135                 140

Asn Asn Phe Ser Gly Arg Thr Leu Gly Cys Val Ser Ala Ser Thr Asp
145                 150                 155                 160

Lys Lys Cys Lys Asn Asn Phe Gly Pro Phe Val Pro Asn Phe Leu Lys
                165                 170                 175

Val Pro Tyr Asp Asp Leu Glu Ala Leu Glu Lys Glu Leu Gln Asp Pro
            180                 185                 190

Asn Val Cys Ala Phe Ile Val Glu Pro Val Gln Gly Glu Ala Gly Val
                195                 200                 205

Ile Val Pro Ser Asp Ser Tyr Phe Pro Gly Val Ala Ser Leu Cys Lys
        210                 215                 220

Lys Tyr Asn Val Leu Phe Val Ala Asp Glu Val Gln Thr Gly Leu Gly
225                 230                 235                 240

Arg Thr Gly Lys Leu Leu Cys Thr His His Tyr Gly Val Lys Pro Asp
                245                 250                 255

Val Ile Leu Leu Gly Lys Ala Leu Ser Gly Gly His Tyr Pro Ile Ser
            260                 265                 270

Ala Ile Leu Ala Asn Asp Asp Val Met Leu Val Leu Lys Pro Gly Glu
                275                 280                 285

His Gly Ser Thr Tyr Gly Gly Asn Pro Leu Ala Ala Ile Cys Val
        290                 295                 300

Glu Ala Leu Lys Val Leu Ile Asn Glu Lys Leu Cys Glu Asn Ala Asp
305                 310                 315                 320

Lys Leu Gly Ala Pro Phe Leu Gln Asn Leu Lys Glu Gln Leu Lys Asp
                325                 330                 335

Ser Lys Val Val Arg Glu Val Arg Gly Lys Gly Leu Leu Cys Ala Ile
            340                 345                 350

Glu Phe Lys Asn Asp Leu Val Asn Val Trp Asp Ile Cys Leu Lys Phe
                355                 360                 365

Lys Glu Asn Gly Leu Ile Thr Arg Ser Val His Asp Lys Thr Val Arg
                370                 375                 380

<210> SEQ ID NO 3
<211> LENGTH: 409
<212> TYPE: PRT
<213> ORGANISM: Hammondia hammondi

<400> SEQUENCE: 3

Met Ala Thr Lys Ser Ser Ser Ala Ser Ala Ala Glu Ser Gly
1               5                   10                  15

Ala Arg Lys Thr Asn Ile Glu Ala Tyr Arg Asp Gly Leu Lys Leu Lys
                20                  25                  30

Thr Glu Glu Asp Phe Phe Ala Cys Asp Arg Gln Tyr Val Cys Arg Asn
            35                  40                  45

Tyr Ala Pro Val Pro Val Ile Ser Lys Gly Lys Gly Ala Arg Val
        50                  55                  60

Trp Asp Ile Asn Gly Asn Glu Tyr Tyr Asp Phe Leu Ala Gly Val Ser
65                  70                  75                  80

Ser Leu Ser Gln Gly His Cys His Pro Arg Val Ile Ala Ala Leu Cys
                85                  90                  95

Arg Gln Ala Glu Gln Leu Thr Leu Thr Leu Arg Ser Phe Gly Asn Asp
            100                 105                 110

Val Thr Gly Pro Ala Cys Arg Phe Met Ala Glu Met Phe Gly Tyr Asp
```

```
              115                 120                 125
Arg Val Leu Leu Met Asn Thr Gly Ala Glu Ala Gly Glu Ser Ala Leu
    130                 135                 140

Lys Ile Ala Arg Lys Trp Ala Tyr Glu Val Lys Glu Ile Pro Pro Asp
145                 150                 155                 160

Ser Ala Lys Val Ile Leu Cys Asn Asn Asn Tyr Trp Gly Arg Thr Ile
                165                 170                 175

Thr Ala Cys Ser Ser Ser Thr Thr Phe Asp Cys Tyr Asn Asn Phe Gly
            180                 185                 190

Pro Phe Thr Pro Gly Phe Glu Leu Ile Asp Tyr Asp Val Gly Ala
        195                 200                 205

Leu Glu Glu Ala Leu Lys Asp Pro Asn Val Ala Ala Phe Phe Val Glu
    210                 215                 220

Pro Ile Gln Gly Glu Gly Gly Val Asn Val Pro Lys Pro Gly Tyr Leu
225                 230                 235                 240

Lys Arg Ala His Glu Leu Cys Lys Ser Lys Asn Val Leu Leu Ile Val
                245                 250                 255

Asp Glu Ile Gln Thr Gly Leu Cys Arg Thr Gly Arg Met Leu Ala Val
            260                 265                 270

Asp His Asp Glu Val His Pro Asp Ile Leu Leu Gly Lys Ser Leu
        275                 280                 285

Ser Ala Gly Val Val Pro Ile Ser Ala Val Met Gly Arg Ala Asp Val
    290                 295                 300

Met Asp Val Leu Lys Pro Gly Thr His Gly Ser Thr Phe Gly Gly Asn
305                 310                 315                 320

Pro Leu Ala Cys Ala Val Ala Val Glu Ala Leu Thr Val Leu Lys Asp
                325                 330                 335

Glu Lys Leu Ala Asp Arg Ala Glu Arg Leu Gly Leu Gln Phe Arg Asp
            340                 345                 350

Cys Leu Arg Arg Glu Leu Cys Gly Lys Val Ser Trp Ile Lys Glu Ile
        355                 360                 365

Arg Gly Arg Gly Leu Leu Asn Ala Val Glu Val Asp Ser Asn Val Ile
    370                 375                 380

Asp Pro Asn Asp Val Val Met Lys Leu Lys Glu Asn Gly Ile Leu Ser
385                 390                 395                 400

Lys Pro Thr Arg Val Arg Val Met Arg
                405

<210> SEQ ID NO 4
<211> LENGTH: 409
<212> TYPE: PRT
<213> ORGANISM: Neospora caninum

<400> SEQUENCE: 4

Met Ser Thr Asp Cys Asp Ser Thr Ala Leu Ala Ala Gln Tyr Gly
1               5                   10                  15

Asp Glu Lys Met Ser Ile Cys Ile Tyr Arg Asp Ser Leu Lys Leu Lys
                20                  25                  30

Thr Glu Glu Asp Phe Phe Ala Cys Asp Arg Gln Tyr Val Cys Gly Asn
            35                  40                  45

Tyr Ala Pro Val Pro Val Val Ile Ser Lys Gly Lys Gly Ala Arg Val
        50                  55                  60

Trp Asp Ile Asn Gly Lys Glu Tyr Tyr Asp Phe Leu Ala Gly Val Ser
65                  70                  75                  80
```

```
Ser Leu Ser Gln Gly His Cys His Pro Arg Val Thr Ala Ala Leu Cys
                85                  90                  95

Arg Gln Ala Glu Gln Leu Thr Leu Thr Leu Arg Ser Phe Gly Asn Asp
            100                 105                 110

Val Thr Gly Pro Ala Cys Arg Phe Met Ala Glu Met Phe Gly Tyr Asp
        115                 120                 125

Arg Val Leu Leu Met Asn Thr Gly Ala Glu Ala Gly Glu Ser Ala Ile
    130                 135                 140

Lys Ile Ala Arg Lys Trp Ala Tyr Glu Val Lys Gly Val Pro Gln Glu
145                 150                 155                 160

Ser Ala Lys Ile Ile Leu Cys Asn Asn Asn Tyr Trp Gly Arg Thr Ile
                165                 170                 175

Thr Ala Cys Ser Ser Thr Thr Phe Asp Cys Tyr Asn Asn Phe Gly
            180                 185                 190

Pro Phe Thr Pro Gly Phe Glu Leu Ile Asn Tyr Asp Asp Ile Asp Ala
        195                 200                 205

Leu Glu Gly Ala Leu Lys Asp Pro Asn Val Ala Ala Phe Phe Val Glu
    210                 215                 220

Pro Ile Gln Gly Glu Gly Gly Val Asn Val Pro Lys Lys Gly Tyr Leu
225                 230                 235                 240

Lys Arg Ala His Glu Leu Cys Lys Ser Lys Asp Val Leu Leu Ile Val
                245                 250                 255

Asp Glu Ile Gln Thr Gly Leu Cys Arg Thr Gly Arg Leu Leu Ala Ala
            260                 265                 270

Asp His Asp Glu Val His Pro Asp Ile Leu Leu Gly Lys Ser Leu
        275                 280                 285

Ser Ala Gly Val Val Pro Ile Ser Ala Val Met Gly Arg Ala Asp Val
    290                 295                 300

Met Asp Val Leu Lys Pro Gly Thr His Gly Ser Thr Phe Gly Gly Asn
305                 310                 315                 320

Pro Leu Ala Cys Ala Val Ala Val Glu Ala Leu Thr Val Leu Lys Asp
                325                 330                 335

Glu Lys Leu Ala Asp Arg Ala Glu Arg Leu Gly Asn Glu Phe Arg Asp
            340                 345                 350

Cys Leu Thr Lys Gln Leu Asp Gly Lys Val Pro Trp Ile Lys Glu Ile
        355                 360                 365

Arg Gly Arg Gly Leu Leu Asn Ala Val Glu Val Asp Ser Asp Ile Ile
    370                 375                 380

Asp Pro Asn Asp Val Val Thr Lys Leu Lys Glu Asn Gly Ile Leu Thr
385                 390                 395                 400

Lys Pro Thr Arg Val Lys Val Leu Arg
                405

<210> SEQ ID NO 5
<211> LENGTH: 413
<212> TYPE: PRT
<213> ORGANISM: Felis catus

<400> SEQUENCE: 5

Met Phe Ser Lys Leu Ala His Leu Gln Thr Ile Ser Val Leu Arg Arg
1               5                   10                  15

Gly Val His Ser Ser Val Ala Ser Ala Thr Ser Val Ala Thr Lys Lys
            20                  25                  30

Thr Ile Gln Gly Pro Pro Ser Ser Asp Tyr Ile Phe Glu Arg Glu Ser
        35                  40                  45
```

```
Lys Tyr Gly Ala His Asn Tyr His Pro Leu Pro Val Ala Leu Glu Arg
 50                  55                  60
Gly Lys Gly Ile Tyr Val Trp Asp Val Glu Gly Arg Lys Tyr Phe Asp
 65                  70                  75                  80
Phe Leu Ser Ala Tyr Ser Ala Val Asn Gln Gly His Cys His Pro Lys
                 85                  90                  95
Ile Val Asn Ala Leu Lys Ser Gln Ala Asp Lys Leu Thr Leu Thr Ser
            100                 105                 110
Arg Ala Phe Tyr Asn Asn Val Leu Gly Glu Tyr Glu Tyr Val Thr
        115                 120                 125
Lys Leu Phe Asn Tyr His Lys Val Leu Pro Met Asn Thr Gly Val Glu
130                 135                 140
Ala Gly Glu Thr Ala Cys Lys Leu Ala Arg Arg Trp Gly Tyr Thr Val
145                 150                 155                 160
Lys Gly Ile Pro Lys Tyr Lys Ala Lys Val Val Phe Ala Ala Gly Asn
                165                 170                 175
Phe Trp Gly Arg Thr Leu Ser Ala Ile Ser Ser Ser Thr Asp Pro Thr
            180                 185                 190
Ser Tyr Glu Gly Phe Gly Pro Phe Met Pro Gly Phe Glu Ile Ile Pro
        195                 200                 205
Tyr Asn Asp Leu Pro Ala Leu Glu Arg Val Leu Gln Asp Pro Asn Val
210                 215                 220
Ala Ala Phe Met Val Glu Pro Ile Gln Gly Glu Ala Gly Val Val Val
225                 230                 235                 240
Pro Asp Pro Gly Tyr Met Met Gly Val Arg Glu Leu Cys Thr Arg His
                245                 250                 255
Gln Val Leu Phe Ile Ala Asp Glu Ile Gln Thr Gly Leu Ala Arg Thr
            260                 265                 270
Gly Arg Trp Leu Ala Val Asp His Asp Asn Val Arg Pro Asp Val Val
        275                 280                 285
Leu Leu Gly Lys Ala Leu Ser Gly Gly Leu Tyr Pro Val Ser Ala Val
290                 295                 300
Leu Cys Asp Asp Glu Val Met Leu Thr Ile Lys Pro Gly Glu His Gly
305                 310                 315                 320
Ser Thr Tyr Gly Gly Asn Pro Leu Gly Cys Arg Val Ala Ile Ala Ala
                325                 330                 335
Leu Glu Val Leu Glu Glu Glu Asn Leu Ala Glu Asn Ala Glu Lys Met
            340                 345                 350
Gly Ile Ile Leu Arg Asn Glu Leu Met Lys Leu Pro Ser Asp Ile Val
        355                 360                 365
Thr Ala Val Arg Gly Lys Gly Leu Leu Asn Ala Ile Val Ile Arg Glu
370                 375                 380
Thr Lys Asp Cys Asp Ala Trp Lys Val Cys Leu Arg Leu Arg Asp Asn
385                 390                 395                 400
Gly Leu Leu Ala Lys Pro Thr His Gly Asp Ile Ile Arg
                405                 410
```

<210> SEQ ID NO 6
<211> LENGTH: 413
<212> TYPE: PRT
<213> ORGANISM: Homo sapiens

<400> SEQUENCE: 6

Met Phe Ser Lys Leu Ala His Leu Gln Arg Phe Ala Val Leu Ser Arg

```
1               5                   10                  15
Gly Val His Ser Ser Val Ala Ser Ala Thr Ser Val Ala Thr Lys Lys
                20                  25                  30
Thr Val Gln Gly Pro Pro Thr Ser Asp Asp Ile Phe Glu Arg Glu Tyr
                35                  40                  45
Lys Tyr Gly Ala His Asn Tyr His Pro Leu Pro Val Ala Leu Glu Arg
                50                  55                  60
Gly Lys Gly Ile Tyr Leu Trp Asp Val Glu Gly Arg Lys Tyr Phe Asp
65                  70                  75                  80
Phe Leu Ser Ser Tyr Ser Ala Val Asn Gln Gly His Cys His Pro Lys
                85                  90                  95
Ile Val Asn Ala Leu Lys Ser Gln Val Asp Lys Leu Thr Leu Thr Ser
                100                 105                 110
Arg Ala Phe Tyr Asn Asn Val Leu Gly Glu Tyr Glu Glu Tyr Ile Thr
                115                 120                 125
Lys Leu Phe Asn Tyr His Lys Val Leu Pro Met Asn Thr Gly Val Glu
                130                 135                 140
Ala Gly Glu Thr Ala Cys Lys Leu Ala Arg Lys Trp Gly Tyr Thr Val
145                 150                 155                 160
Lys Gly Ile Gln Lys Tyr Lys Ala Lys Ile Val Phe Ala Ala Gly Asn
                165                 170                 175
Phe Trp Gly Arg Thr Leu Ser Ala Ile Ser Ser Ser Thr Asp Pro Thr
                180                 185                 190
Ser Tyr Asp Gly Phe Gly Pro Phe Met Pro Gly Phe Asp Ile Ile Pro
                195                 200                 205
Tyr Asn Asp Leu Pro Ala Leu Glu Arg Ala Leu Gln Asp Pro Asn Val
                210                 215                 220
Ala Ala Phe Met Val Glu Pro Ile Gln Gly Glu Ala Gly Val Val Val
225                 230                 235                 240
Pro Asp Pro Gly Tyr Leu Met Gly Val Arg Glu Leu Cys Thr Arg His
                245                 250                 255
Gln Val Leu Phe Ile Ala Asp Glu Ile Gln Thr Gly Leu Ala Arg Thr
                260                 265                 270
Gly Arg Trp Leu Ala Val Asp Tyr Glu Asn Val Arg Pro Asp Ile Val
                275                 280                 285
Leu Leu Gly Lys Ala Leu Ser Gly Gly Leu Tyr Pro Val Ser Ala Val
                290                 295                 300
Leu Cys Asp Asp Asp Ile Met Leu Thr Ile Lys Pro Gly Glu His Gly
305                 310                 315                 320
Ser Thr Tyr Gly Gly Asn Pro Leu Gly Cys Arg Val Ala Ile Ala Ala
                325                 330                 335
Leu Glu Val Leu Glu Glu Asn Leu Ala Glu Asn Ala Asp Lys Leu
                340                 345                 350
Gly Ile Ile Leu Arg Asn Glu Leu Met Lys Leu Pro Ser Asp Val Val
                355                 360                 365
Thr Ala Val Arg Gly Lys Gly Leu Leu Asn Ala Ile Val Ile Lys Glu
                370                 375                 380
Thr Lys Asp Trp Asp Ala Trp Lys Val Cys Leu Arg Leu Arg Asp Asn
385                 390                 395                 400
Gly Leu Leu Ala Lys Pro Thr His Gly Asp Ile Ile Arg
                405                 410

<210> SEQ ID NO 7
```

```
<211> LENGTH: 753
<212> TYPE: DNA
<213> ORGANISM: Toxoplasma gondii

<400> SEQUENCE: 7
ctggaaaggt gtttcaacac aatttgcgtg cacagaaaca tcaacactga acttcacact      60
ggcaactctc agacatacac tgtaaagggt gtgtttacac agatgtgaac tactgactttt    120
actcaagaaa gtgatgttgg cgtgaccatt ttgtcatata catgttttgc aatctctaga     180
gcctcagtca agggcattgt caccccgcg tcattgcagc actgtgccgc caggcggagc      240
ggttgactct caccctacgg gcttttggaa atgacgtcac aggaccagca tgcaggttca     300
tggcggaaat gtttgggtac gaccgtgttc tcctcatgaa taccggtgag cgcaaaggag     360
gttcagattc tcgtgatacg ctgcagtctg cattaaacgt tgacggttcc cttgtcctta    420
cgtgggattt gcccaacatt aacagccagt ccaggcttac tggtcgcgaa cgaacaatgt     480
ttttgcaggg gctttctacg aggacaaacg tatgtgcatg gactgggaca ggcgacgctt     540
tttgtggagt ataaatatta ggtttgtgtg cgcgttattg ctctcgtcag gtgccgaggc     600
tggtgaatct gctctcaaaa tcgcgcgcaa gtgggcgtac gaggtgaaag aaattccacc     660
agactctgcc aaagttattt tgtgcaacaa caactactgg gggaggacaa tcaccgcgtg     720
cagttcatct accacattcg attgctacaa taa                                  753
```